(12) United States Patent
Malecha et al.

(10) Patent No.: US 7,470,722 B2
(45) Date of Patent: Dec. 30, 2008

(54) MULTICYCLIC SULFONAMIDE COMPOUNDS AS INHIBITORS OF HISTONE DEACETYLASE FOR THE TREATMENT OF DISEASE

(75) Inventors: James William Malecha, San Diego, CA (US); Stewart Alwyn Noble, San Diego, CA (US); Christian Andreus Hassig, Mira Mesa, CA (US); Paul L. Wash, San Diego, CA (US); Brandon M. Wiley, Philadelphia, PA (US); Charles Maxwell Lawrence, San Diego, CA (US); Timothy Z. Hoffman, San Diego, CA (US)

(73) Assignee: Kalypsys, Inc., San Diego, CA (US)

( * ) Notice: Subject to any disclaimer, the term of this patent is extended or adjusted under 35 U.S.C. 154(b) by 126 days.

(21) Appl. No.: 11/150,500

(22) Filed: Jun. 9, 2005

(65) Prior Publication Data

US 2006/0030543 A1    Feb. 9, 2006

Related U.S. Application Data

(60) Provisional application No. 60/635,020, filed on Dec. 9, 2004.

(30) Foreign Application Priority Data

Jun. 10, 2004    (WO) .............. PCT/US2004/018502

(51) Int. Cl.
*A61K 31/35* (2006.01)
*C07D 319/14* (2006.01)

(52) U.S. Cl. .................. 514/456; 549/362; 549/462; 548/484; 548/302.7; 546/139; 546/134; 546/246; 544/159; 544/339; 544/381; 514/464; 514/396; 514/252.2; 514/315

(58) Field of Classification Search .................. 544/159, 544/339, 381; 546/139, 134, 246; 548/484, 548/302.7; 549/362, 462; 514/237.8, 305, 514/396, 452, 252.12, 315, 307, 415, 464, 514/299, 456
See application file for complete search history.

(56) References Cited

U.S. PATENT DOCUMENTS

| 3,660,542 | A | | 5/1972 | Adachi | |
|---|---|---|---|---|---|
| 4,226,775 | A | * | 10/1980 | McEvoy et al. | ............. 548/533 |
| 4,866,091 | A | | 9/1989 | Matsuo et al. | |
| 5,034,417 | A | | 7/1991 | Matsuo et al. | |
| 2003/0229126 | A1 | | 12/2003 | Satoh et al. | |
| 2006/0030554 | A1 | | 2/2006 | Malecha | |

FOREIGN PATENT DOCUMENTS

| WO | 2006063294 A2 | 6/2006 |
|---|---|---|
| WO | 2007016354 A1 | 2/2007 |
| WO | 2007067994 A1 | 6/2007 |

OTHER PUBLICATIONS

Joseph E. Payne; Inhibitors of Histone Deacetylase for the Treatment of Disease; U.S. Appl. No. 11/608,736, filed Dec. 8, 2006 (not yet published); Kalypsys, Inc.

* cited by examiner

*Primary Examiner*—Rei-tsang Shiao
(74) *Attorney, Agent, or Firm*—Dennis A. Bennett; Cynthia Hathaway

(57) ABSTRACT

Disclosed herein are carbonyl compounds of Formula I as described herein.

(I)

Methods and compositions are disclosed for treating disease states including, but not limited to cancers, autoimmune diseases, tissue damage, central nervous system disorders, neurodegenerative disorders, fibrosis, bone disorders, polyglutamine-repeat disorders, anemias, thalassemias, inflammatory conditions, cardiovascular conditions, and disorders in which angiogenesis play a role in pathogenesis, using the compounds of the invention. In addition, methods of modulating the activity of histone deacetylase (HDAC) are also disclosed.

43 Claims, 5 Drawing Sheets

MULTICYCLIC SULFONAMIDE COMPOUNDS AS INHIBITORS OF HISTONE DEACETYLASE FOR THE TREATMENT OF DISEASE

RELATED DOCUMENTS

The present application claims priority to the following applications: U.S. Patent Application No. 60/635,020 filed Dec. 9, 2004; U.S. patent application Ser. No.: 10/865,743 filed Jun. 10, 2004 and PCT/US2004/018502 filed Jun. 10, 2004 which are incorporated herein by reference in their entirety.

FIELD OF THE INVENTION

The present invention is directed to carbonyl compounds as inhibitors of histone deacetylase (HDAC). These compounds are useful in treating disease states including cancers, autoimmune diseases, tissue damage, central nervous system disorders, neurodegenerative disorders, fibrosis, bone disorders, polyglutamine-repeat disorders, anemias, thalassemias, inflammatory conditions, cardiovascular conditions, and disorders in which angiogenesis plays a role in pathogenesis.

BACKGROUND OF THE INVENTION

Histone proteins organize DNA into nucleosomes, which are regular repeating structures of chromatin. The acetylation status of histones alters chromatin structure, which, in turn, is involved in gene expression. Two classes of enzymes can affect the acetylation of histones—histone acetyltransferases (HATs) and histone deacetylases (HDACs). A number of HDAC inhibitors have been characterized. However, to date no effective candidate for cancer therapy has been identified. Therefore, there is a need in the art to discover HDAC inhibitors that have effective anti-tumor activity.

SUMMARY OF THE INVENTION

1. Disclosed herein are carbonyl compounds of Formula I and related formulae as described herein, including their pharmaceutically acceptable salts, esters, and pro-drugs: A compound having structural formula I,

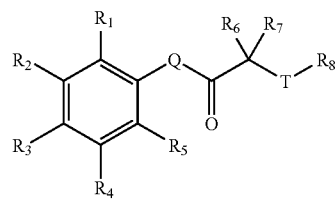

(I)

or a pharmaceutically acceptable salt, amide, ester, or pro-drug thereof, wherein a) $R_8$ is selected from the group consisting of
  i) hydrogen;

ii) 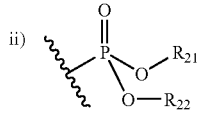

wherein $R_{21}$ and $R_{22}$ are independently selected from the group consisting of hydrogen, optionally substituted alkyl, optionally substituted aryl, and optionally substituted heteroaryl;

iii) cyano;

iv) 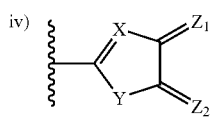

wherein
  X is selected from CH and nitrogen;
  Y is selected from the group consisting of $CH_2$, NH, oxygen and sulfur;
  $Z_1$ and $Z_2$ are each independently selected from the group consisting of null, oxygen, sulfur, and $CR_{11}R_{12}$,
    wherein $R_{11}$ and $R_{12}$ are each independently selected from the group consisting of hydrogen, lower alkyl, lower alkoxy, aryl, aryloxy, $NH_2$, halogen, perhaloalkyl, and hydroxy; and v) 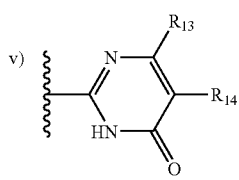

wherein $R_{13}$ and $R_{14}$ are each independently selected from the group consisting of hydrogen, lower alkyl, lower alkoxy, aryl, aryloxy, $NH_2$, halogen, perhaloalkyl, and hydroxy;

vi) optionally substituted acyl of the formula $-C(O)R_E$, wherein $R_E$ is defined such that the compound having structural formula I may be hydrolyzed to yield a pharmaceutically acceptable acid $HOC(O)R_E$;

vii) optionally substituted thiol, wherein T taken in combination with sulfur forms a disulfide;

viii) or $R_8$ is equivalent to the balance of Formula I to form a disulfide dimer;

b) T is selected from the group consisting of oxygen, sulfur, and $-NR_{17}$, wherein $R_{17}$ is selected from the group consisting of hydrogen, and optionally substituted lower alkyl;

c) $R_6$ and $R_7$ are each independently selected from the group consisting of hydrogen and lower alkyl or $R_6$ and $R_7$ taken together form an optionally substituted cycloalkyl;

d) Q is selected from the group consisting of a bond, $-(CH_2)_m-$, $-(CH_2)_nNH-$, $-(CH_2)_m(CO)-$, —(CH$_2$)$_m$NH(CO)—, and —(CH$_2$)$_m$C(O)NH—, wherein m is 0-2 and n is 1-2, wherein if Q is not symmetric, Q may be attached in either order; and e) each R$_1$-R$_5$ is each independently selected from the group consisting of
  i) hydrogen;
  ii) optionally substituted lower alkyl;
  iii) optionally substituted aryl, heteroaryl, alkaryl, cycloalkyl, heterocycloalkyl;
  iv) halogen or perhaloalkyl;
  v) an alkoxy of formula —(X$_1$)$_{n1}$—O—X$_2$, where
    X$_1$ is selected from the group consisting of lower alkylene, lower alkenylene, lower alkynylene, aryl, and heteroaryl;
    X$_2$ is selected from the group consisting of hydrogen, optionally substituted lower alkyl, lower perfluoroalkyl, optionally substituted aryl, optionally substituted heteroaryl, optionally substituted cycloalkyl, and optionally substituted heterocycloalkyl; and
    n1 is 0, 1, 2 or 3; and
  vi) an acyl of formula —(X$_3$)$_{n1}$—C(O)—X$_4$, where
    X$_3$ is selected from the group consisting of lower alkylene, lower alkenylene, lower alkynylene, aryl, and heteroaryl;
    X$_4$ is selected from the group consisting of optionally substituted lower alkyl, optionally substituted aryl, perfluoroalkyl, optionally substituted heteroaryl, optionally substituted heterocycloalkyl, hydroxy, optionally substituted alkoxy, amino, and —NH—X$_5$,
      where X$_5$ is selected from the group consisting of hydrogen, optionally substituted alkyl, optionally substituted aryl, optionally substituted heteroaryl, and optionally substituted heterocycloalkyl; and
    n1 is 0, 1, 2, or 3; and
  vii) cyano;
  viii) an amino of formula —(X$_{15}$)$_{n15}$—NX$_{16}$X$_{17}$, where
    X$_{15}$ is selected from the group consisting of lower alkylene, lower alkenylene, lower alkynylene, aryl, and heteroaryl;
    X$_{16}$ and X$_{17}$ are each independently selected from the group consisting of hydrogen, optionally substituted lower alkyl, optionally substituted aryl, optionally substituted heteroaryl, and —C(O)X$_6$,
      where X$_6$ is selected from the group consisting of hydrogen, optionally substituted alkyl, optionally substituted aryl, optionally substituted heteroaryl, and optionally substituted heterocycloalkyl;
    or X$_{16}$ and X$_{17}$, taken together with the nitrogen to which they are attached, form an optionally substituted five-membered or six-membered heteroaromatic or heteroaliphatic ring; and
    n$_{15}$ is 0 or 1;
  x) a thioether or thiol of formula —(X$_{22}$)$_{n22}$—S—X$_{23}$, where
    X$_{22}$ is selected from the group consisting of lower alkylene, lower alkenylene, lower alkynylene, aryl, and heteroaryl;
    X$_{23}$ is selected from the group consisting of hydrogen, optionally substituted lower alkyl, perflouralkyl, optionally substituted aryl, and optionally substituted heteroaryl; and
    n22 is 0, 1, 2, or 3;

xi) an N-sulfonamido of structure

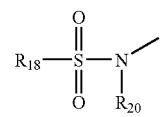

xii) an S-sulfonamido of formula

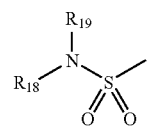

or
  R$_1$ and R$_2$, taken together along with the two ring carbons to which they are attached, or R$_2$ and R$_3$, taken together along with the two ring carbons to which they are attached, or R$_3$ and R$_4$, taken together along with the two ring carbons to which they are attached, or R$_4$ and R$_5$, taken together along with the two ring carbons to which they are attached, form a five-, six-, seven-, or eight-membered carbocyclic or heterocyclic aliphatic ring, or a six-membered aromatic or heteroaromatic, or a five- or six-membered heteroaromatic ring, each of which is optionally substituted with one or more substituents, R$_1$;
  wherein at least one of R$_1$, R$_2$, R$_3$, R$_4$, and R$_5$ is selected from the group of N-sulfonamido and S-sulfonamido;
  further wherein R$_{18}$ is G$_1$-G$_2$-,
    where G$_2$ is selected from the group consisting of a bond and optionally substituted lower alkylene; and G$_1$ comprises at least two rings and is selected from the group consisting of optionally substituted fused polycyclic aryl, optionally substituted fused polycyclic heteroaryl, optionally substituted fused polycyclic aryl and cycloalkyl, optionally substituted fused polycyclic aryl and heterocycloalkyl, optionally substituted linked biaryl, optionally substituted linked aryl-heteroaryl, optionally substituted linked heteroaryl-heteroaryl, and optionally substituted linked aryl-heterocycloalkyl;
  or R$_{18}$ taken together with R$_{19}$ and the nitrogen to which they are attached forms an optionally substituted heterocycloalkyl which is fused or linked with optionally substituted aryl or heteroaryl;
  R$_{19}$ is H, optionally substituted lower alkyl, optionally substituted aralkyl, or taken together with one of R$_1$, R$_2$, R$_3$, R$_4$, or R$_5$, said R$_{19}$ forms an optionally substituted five-, six-, seven-, or eight-membered heterocyclic ring, having the following structure:

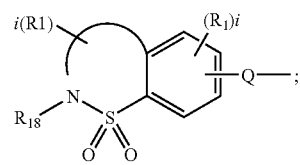

wherein each i is 0, 1, 2, 3, 4; and
  R$_{20}$ is H, optionally substituted lower alkyl, optionally substituted lower aralkyl, or R$_{20}$ taken together with R$_{18}$ forms an optionally substituted five-, six-, seven-, or eight-membered heterocyclic ring, having the following structure:

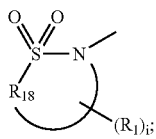

i is 0, 1, 2, 3, 4.

The invention provides pharmaceutical compositions comprising a compound having structural formula I or a related formula, which are capable of inhibiting the catalytic activity of histone deacetylase (HDAC).

The invention also provides methods and compositions for treating diseases in mammals using compounds of the invention, including but not limited to, treating cancers, autoimmune diseases, tissue damage, central nervous system disorders, neurodegenerative disorders, fibrosis, bone disorders, polyglutamine-repeat disorders, anemias, thalassemias, inflammatory conditions, cardiovascular conditions, and disorders in which angiogenesis plays a role in pathogenesis.

BRIEF DESCRIPTION OF FIGURES

FIG. 2 shows the effects of HDAC inhibitors on histone H3 and H4 hyperacetylation.

FIG. 3 shows a Western blot of 30 μg of peripheral blood mononuclear cell lysate probed for acetylated histone H3; lanes marked "Vehicle" are lysates from mice treated with vehicle only (control), lanes marked "25" are lysates from mice treated with 25 mg/kg/day of Compound 02, lanes marked "50" are lysates from mice treated with 50 mg/kg/day of Compound 02. and lanes marked "100" are lysates from mice treated with 25 mg/kg/day of Compound 02.

FIG. 5 shows thiol levels and test compound levels in plasma at various times after intraperitoneal injection of test compound.

DETAILED DESCRIPTION OF THE PREFERRED EMBODIMENT

Figure 1:
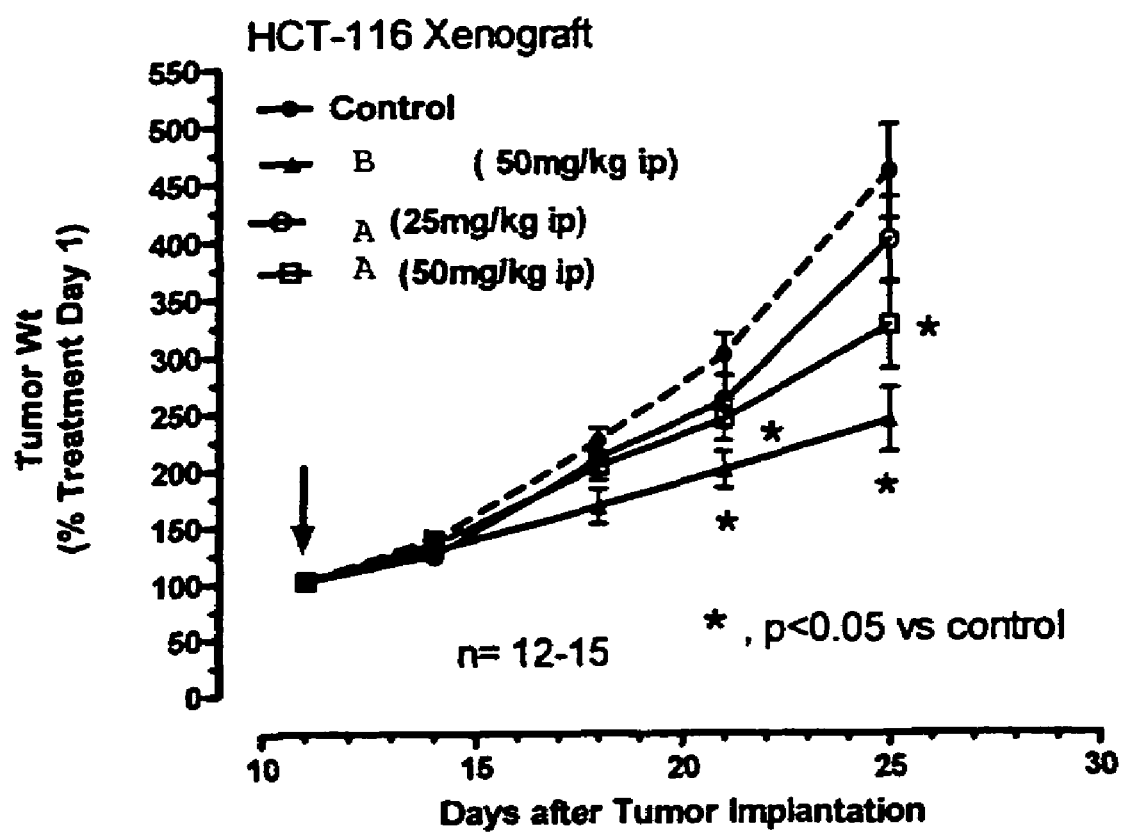
FIG. 1 shows the effects of HDAC inhibitors Compound A at 25 mg/kg and 50 mg/kg, and Compound B on the growth of a HCT-116 xenograft tumor in female athymic nude mice over a period of 25 days after tumor implanation; tumor weight was calculated as (tumor length (mm)×tumor width$^2$ (mm))/2; symbols represent mean±SEM for n=12-15 per treatment group.

Disclosed herein are carbonyl compounds of Formula II and related formulae as described herein, including their pharmaceutically acceptable salts, esters, and pro-drugs, having a structure of Formula II and the groups as defined above.

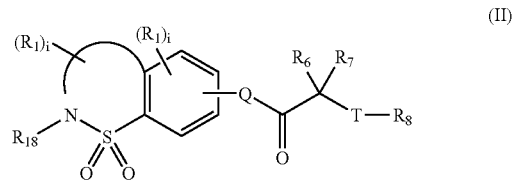

(II)

The formula above can have a structure selected from a group consisting of:

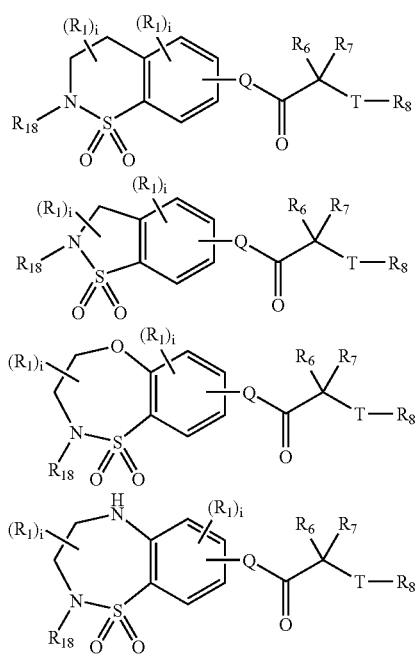

In another embodiment $R_1$ can be an endocyclic carbonyl.

The formula above can have a structure of formula III:

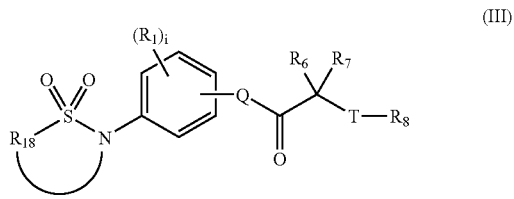

(III)

The formula above can have a structure wherein the compound has a structure selected from a group consisting of:

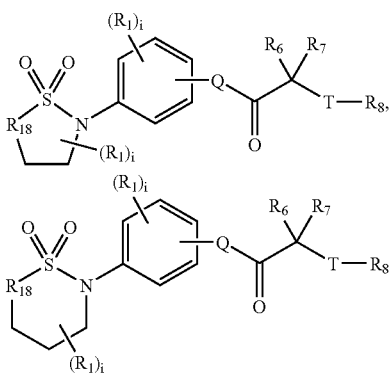

The formula above wherein the compound has the structure selected from a group consisting of:

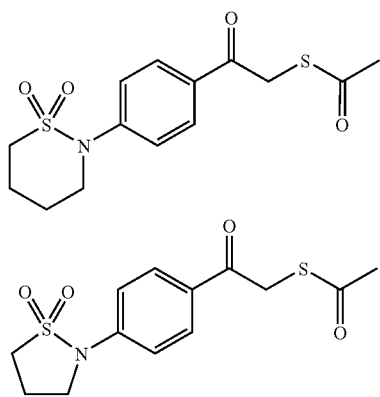

There is also disclosed a pharmaceutical composition comprising a compound of structural formula I,

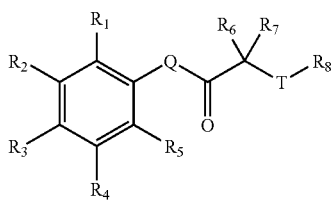

wherein
a) $R_8$ is selected from the group consisting of
  i) hydrogen;
  ii) optionally substituted $C_1$-$C_8$ straight-chain, branched, or cyclic saturated or unsaturated alkyl;
  iii) cyano;

iv) 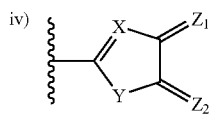

wherein
X is selected from CH and nitrogen;
Y is selected from the group consisting of $CH_2$, NH, oxygen and sulfur;
$Z_1$ and $Z_2$ are each independently selected from the group consisting of null, oxygen, sulfur, and $CR_{11}R_{12}$,
  wherein $R_{11}$ and $R_{12}$ are each independently selected from the group consisting of hydrogen, lower alkyl, lower alkoxy, aryl, aryloxy, $NH_2$, halogen, perhaloalkyl, and hydroxy; and v) 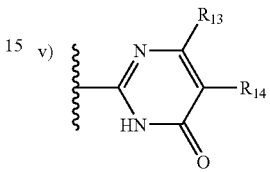

wherein $R_{13}$ and $R_{14}$ are each independently selected from the group consisting of hydrogen, lower alkyl, lower alkoxy, aryl, aryloxy, $NH_2$, halogen, perhaloalkyl, and hydroxy;
  vii) optionally substituted acyl of the formula —C(O)$R_E$, wherein $R_E$ is defined such that the compound having structural formula I may be hydrolyzed to yield a pharmaceutically acceptable acid HOC(O)$R_E$;
  viii) or $R_8$ is equivalent to the balance of Formula I to form a disulfide dimer;

ix) 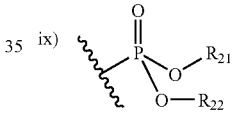

wherein $R_{21}$ and $R_{22}$ are independently selected from the group consisting of hydrogen, optionally substituted alkyl, optionally substituted aryl, and optionally substituted heteroaryl;
b) T is selected from the group consisting of oxygen, sulfur, and —NR$_{17}$, wherein R$_{17}$ is selected from the group consisting of hydrogen, and optionally substituted lower alkyl;
c) $R_6$ and $R_7$ are each independently selected from the group consisting of hydrogen and lower alkyl or $R_6$ and $R_7$ taken together form an optionally substituted cycloalkyl;
d) Q is selected from the group consisting of a bond, —(CH$_2$)$_m$—, —(CH$_2$)$_m$NH—, —(CH$_2$)$_m$(CO)—, —(CH$_2$)$_m$NH(CO)—, and —(CH$_2$)$_m$C(O)NH—, wherein m is 0-7, wherein if Q is not symmetric, Q may be attached in either order; and
e) each $R_1$-$R_5$ is each independently selected from the group consisting of
  i) hydrogen;
  ii) optionally substituted lower alkyl;
  iii) optionally substituted heteroaryl, alkaryl, cycloalkyl, heterocycloalkyl;
  iv) halogen or perhaloalkyl;
  v) an alkoxy of formula —(X$_1$)$_{n1}$—O—X$_2$, where
    X$_1$ is selected from the group consisting of lower alkylene, lower alkenylene, lower alkynylene, aryl, and heteroaryl;
    X$_2$ is selected from the group consisting of hydrogen, optionally substituted lower alkyl, lower perfluoroalkyl, optionally substituted aryl, optionally substituted heteroaryl, optionally substituted cycloalkyl, and optionally substituted heterocycloalkyl; and n1 is 0, 1, 2 or 3; and vi) an acyl of formula $-(X_3)_{n1}-C(O)-X_4$, where $X_3$ is selected from the group consisting of lower alkylene, lower alkenylene, lower alkynylene, aryl, and heteroaryl;

$X_4$ is selected from the group consisting of optionally substituted lower alkyl, optionally substituted aryl, perfluoroalkyl, optionally substituted heteroaryl, optionally substituted heterocycloalkyl, hydroxy, optionally substituted alkoxy, amino, and $-NH-X_5$, where $X_5$ is selected from the group consisting of hydrogen, optionally substituted alkyl, optionally substituted aryl, optionally substituted heteroaryl, and optionally substituted heterocycloalkyl; and n1 is 0, 1, 2, or 3; and vii) cyano;

viii) an amino of formula $-(X_{15})_{n15}-NX_{16}X_{17}$, where $X_{15}$ is selected from the group consisting of lower alkylene, lower alkenylene, lower alkynylene, aryl, and heteroaryl;

$X_{16}$ and $X_{17}$ are each independently selected from the group consisting of hydrogen, optionally substituted lower alkyl, optionally substituted aryl, optionally substituted heteroaryl, and $-C(O)X_6$, where $X_6$ is selected from the group consisting of hydrogen, optionally substituted alkyl, optionally substituted aryl, optionally substituted heteroaryl, and optionally substituted heterocycloalkyl;

or $X_{16}$ and $X_{17}$, taken together with the nitrogen to which they are attached, form an optionally substituted five-membered or six-membered heteroaromatic or heteroaliphatic ring; and $n_{15}$ is 0 or 1;

x) a thioether or thiol of formula $-(X_{22})_{n22}-S-X_{23}$, where $X_{22}$ is selected from the group consisting of lower alkylene, lower alkenylene, lower alkynylene, aryl, and heteroaryl;

$X_{23}$ is selected from the group consisting of hydrogen, optionally substituted lower alkyl, perflouralkyl, optionally substituted aryl, and optionally substituted heteroaryl; and n22 is 0, 1, 2, or 3;

xi) an N-sulfonamido of structure

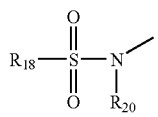

xii) an S-sulfonamido of formula

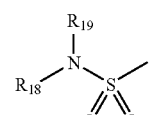

or xiii) $R_1$ and $R_2$, taken together along with the two ring carbons to which they are attached, or $R_2$ and $R_3$, taken together along with the two ring carbons to which they are attached, or $R_3$ and $R_4$, taken together along with the two ring carbons to which they are attached, or $R_4$ and $R_5$, taken together along with the two ring carbons to which they are attached, form a five-, six-, seven-, or eight-membered carbocyclic or heterocyclic aliphatic ring, or a six-membered aromatic or heteroaromatic, or a five- or six-membered heteroaromatic ring, each of which is optionally substituted with one or more substituents, $R_1$;

wherein at least one of $R_1$, $R_2$, $R_3$, $R_4$, and $R_5$ is selected from the group of N-sulfonamido and S-sulfonamido;

further wherein $R_{18}$ is $G_1$-$G_2$-, where $G_2$ is selected from the group consisting of a bond and optionally substituted lower alkylene; and $G_1$ comprises at least two rings and is selected from the group consisting of optionally substituted fused polycyclic aryl, optionally substituted fused polycyclic heteroaryl, optionally substituted fused polycyclic aryl and cycloalkyl, optionally substituted fused polycyclic aryl and heterocycloalkyl, optionally substituted linked bi-aryl, optionally substituted linked aryl-heteroaryl, optionally substituted linked heteroaryl-heteroaryl, and optionally substituted linked aryl-heterocycloalkyl;

or R18 taken together with R19 and the nitrogen to which they are attached forms an optionally substituted heterocycloalkyl which is fused or linked with optionally substituted aryl or heteroaryl;

$R_{19}$ is H, optionally substituted lower alkyl, optionally substituted aralkyl, or taken together with one of $R_1$, $R_2$, $R_3$, $R_4$, or $R_5$, said $R_{19}$ forms an optionally substituted five-, six-, seven-, or eight-membered heterocyclic ring, having the following structure:

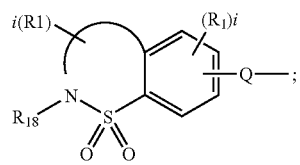

wherein each i is 0, 1, 2, 3, 4; and $R_{20}$ is H, optionally substituted lower alkyl, optionally substituted lower aralkyl, or $R_{20}$ taken together with $R_{18}$ forms an optionally substituted five-, six-, seven-, or eight-membered heterocyclic ring, having the following structure:

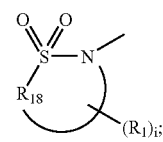

i is 0, 1, 2, 3, 4; and together with in pharmaceutically acceptable carrier.

Further there is disclosed a compound of structural formula I,

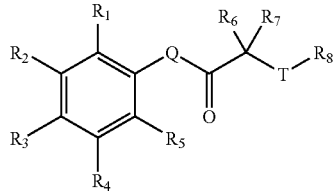

wherein the compound or pharmaceutically acceptable salt, amide, ester or prodrug thereof is capable of inhibiting the catalytic activity of histone deacetylase (HDAC), wherein
a) $R_8$ is selected from the group consisting of
  i) hydrogen;
  ii) optionally substituted $C_1$-$C_8$ straight-chain, branched, or cyclic saturated or unsaturated alkyl;
  iii) cyano;

iv) 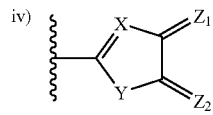

wherein
  X is selected from CH and nitrogen;
  Y is selected from the group consisting of $CH_2$, NH, oxygen and sulfur;
  $Z_1$ and $Z_2$ are each independently selected from the group consisting of null, oxygen, sulfur, and $CR_{11}R_{12}$,
    wherein $R_{11}$ and $R_{12}$ are each independently selected from the group consisting of hydrogen, lower alkyl, lower alkoxy, aryl, aryloxy, $NH_2$, halogen, perhaloalkyl, and hydroxy; and v) 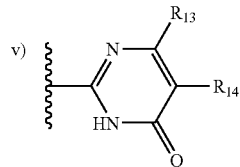

wherein $R_{13}$ and $R_{14}$ are each independently selected from the group consisting of hydrogen, lower alkyl, lower alkoxy, aryl, aryloxy, $NH_2$, halogen, perhaloalkyl, and hydroxy;
  vi) optionally substituted acyl of the formula —C(O)$R_E$, wherein $R_E$ is defined such that the compound having structural formula I may be hydrolyzed to yield a pharmaceutically acceptable acid HOC(O)$R_E$;
  vii) optionally substituted thiol, wherein $G_4$ taken in combination with sulfur forms a disulfide;
  viii) or $R_8$ is equivalent to the balance of Formula I to form a disulfide dimer;
b) T is selected from the group consisting of oxygen, sulfur, and —$NR_{17}$, wherein $R_{17}$ is selected from the group consisting of hydrogen, and optionally substituted lower alkyl;
c) $R_6$ and $R_7$ are each independently selected from the group consisting of hydrogen and lower alkyl or $R_6$ and $R_7$ taken together form an optionally substituted cycloalkyl;
d) Q is selected from the group consisting of a bond, —$(CH_2)_m$—, —$(CH_2)_m$NH—, —$(CH_2)_m$(CO)—, —$(CH_2)_m$NH(CO)—, and —$(CH_2)_m$C(O)NH—, wherein m is 0-7, wherein if Q is not symmetric, Q may be attached in either order; and
e) each $R_1$-$R_5$ is each independently selected from the group consisting of
  i) hydrogen;
  ii) optionally substituted lower alkyl;
  iii) optionally substituted heteroaryl, alkaryl, cycloalkyl, heterocycloalkyl;
  iv) halogen or perhaloalkyl;
  v) an alkoxy of formula —$(X_1)_{n1}$—O—$X_2$, where
    $X_1$ is selected from the group consisting of lower alkylene, lower alkenylene, lower alkynylene, aryl, and heteroaryl;
    $X_2$ is selected from the group consisting of hydrogen, optionally substituted lower alkyl, lower perfluoroalkyl, optionally substituted aryl, optionally substituted heteroaryl, optionally substituted cycloalkyl, and optionally substituted heterocycloalkyl; and
    n1 is 0, 1, 2 or 3; and
  vi) an acyl of formula —$(X_3)_{n1}$—C(O)—$X_4$, where
    $X_3$ is selected from the group consisting of lower alkylene, lower alkenylene, lower alkynylene, aryl, and heteroaryl;
    $X_4$ is selected from the group consisting of optionally substituted lower alkyl, optionally substituted aryl, perfluoroalkyl; optionally substituted heteroaryl, optionally substituted heterocycloalkyl, hydroxy, optionally substituted alkoxy, amino, and —NH—$X_5$,
      where $X_5$ is selected from the group consisting of hydrogen, optionally substituted alkyl, optionally substituted aryl, optionally substituted heteroaryl, and optionally substituted heterocycloalkyl; and
    n1 is 0, 1, 2, or 3; and
  vii) cyano;
  viii) an amino of formula —$(X_{15})_{n15}$—$NX_{16}X_{17}$, where
    $X_{15}$ is selected from the group consisting of lower alkylene, lower alkenylene, lower alkynylene, aryl, and heteroaryl;
    $X_{16}$ and $X_{17}$ are each independently selected from the group consisting of hydrogen, optionally substituted lower alkyl, optionally substituted aryl, optionally substituted heteroaryl, and —C(O)$X_6$,
      where $X_6$ is selected from the group consisting of hydrogen, optionally substituted alkyl, optionally substituted aryl, optionally substituted heteroaryl, and optionally substituted heterocycloalkyl;
    or $X_{16}$ and $X_{17}$, taken together with the nitrogen to which they are attached, form an optionally substituted five-membered or six-membered heteroaromatic or heteroaliphatic ring; and
    $n_{15}$ is 0 or 1;
  x) a thioether or thiol of formula —$(X_{22})_{n22}$—S—$X_{23}$, where
    $X_{22}$ is selected from the group consisting of lower alkylene, lower alkenylene, lower alkynylene, aryl, and heteroaryl;
    $X_{23}$ is selected from the group consisting of hydrogen, optionally substituted lower alkyl, perflouralkyl, optionally substituted aryl, and optionally substituted heteroaryl; and
    n22 is 0, 1, 2, or 3;

xi) an N-sulfonamido of structure

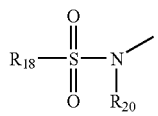

xii) an S-sulfonamido of formula

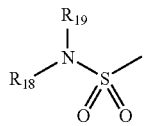

or xiii) $R_1$ and $R_2$, taken together along with the two ring carbons to which they are attached, or $R_2$ and $R_3$, taken together along with the two ring carbons to which they are attached, or $R_3$ and $R_4$, taken together along with the two ring carbons to which they are attached, or $R_4$ and $R_5$, taken together along with the two ring carbons to which they are attached, form a five-, six-, seven-, or eight-membered carbocyclic or heterocyclic aliphatic ring, or a six-membered aromatic or heteroaromatic, or a five- or six-membered heteroaromatic ring, each of which is optionally substituted with one or more substituents, $R_1$;

wherein at least one of $R_1$, $R_2$, $R_3$, $R_4$, and $R_5$ is selected from the group of N-sulfonamido and S-sulfonamido; further wherein $R_{18}$ is $G_1$-$G_2$-, where $G_2$ is selected from the group consisting of a bond and optionally substituted lower alkylene; and $G_1$ comprises at least two rings and is selected from the group consisting of optionally substituted fused polycyclic aryl, optionally substituted fused polycyclic heteroaryl, optionally substituted fused polycyclic aryl and cycloalkyl, optionally substituted fused polycyclic aryl and heterocycloalkyl, optionally substituted linked bi-aryl, optionally substituted linked aryl-heteroaryl, optionally substituted linked heteroaryl-heteroaryl, and optionally substituted linked aryl-heterocycloalkyl; or R18 taken together with R19 and the nitrogen to which they are attached forms an optionally substituted heterocycloalkyl which is fused or linked with optionally substituted aryl or heteroaryl;

$R_{19}$ is H, optionally substituted lower alkyl, optionally substituted aralkyl, or taken together with one of $R_1$, $R_2$, $R_3$, $R_4$, or $R_5$, said $R_{19}$ forms an optionally substituted five-, six-, seven-, or eight-membered heterocyclic ring, having the following structure:

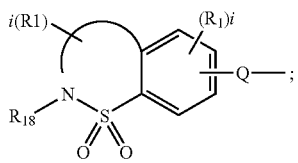

wherein each i is 0, 1, 2, 3, 4; and $R_{20}$ is H, optionally substituted lower alkyl, optionally substituted lower aralkyl, or $R_{20}$ taken together with $R_{18}$ forms an optionally substituted five-, six-, seven-, or eight-membered heterocyclic ring, having the following structure:

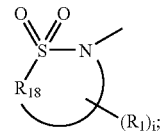

i is 0, 1, 2, 3, 4.

Definition of Terms

The term "pharmaceutically acceptable salt" refers to a formulation of a compound that does not cause significant irritation to an organism to which it is administered and does not abrogate the biological activity and properties of the compound. Pharmaceutical salts can be obtained by reacting a compound of the invention with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound of the invention with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like.

The terms "physiologically acceptable" and "physiologically compatible" refers to excipients, products, or hydrolysis products of disclosed molecular embodiments of the invention. By way of example, protected thiol prodrug embodiments may release acids upon hydrolysis of the protected thiol. Physiologically acceptable excipients and acids are those that do not abrogate the biological activity or properties of the compound, and are nontoxic. "Physiologically acceptable" and "pharmaceutically acceptable" may be coextensive terms.

The term "ester" refers to a chemical moiety with formula —(R)$_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1. Any amine, hydroxy, or carboxyl side chain on the compounds of the present invention can be esterified. The procedures and specific groups to be used to achieve makes such esters are known to those of skill in the art and can readily be found in reference sources such as Greene and Wuts, *Protective Groups in Organic Synthesis*, 3$^{rd}$ Ed., John Wiley & Sons, New York, N.Y., 1999, which is incorporated herein by reference in its entirety.

An "amide" is a chemical moiety with formula —(R)$_n$—C(O)NHR' or —(R)$_n$—NHC(O)R', where R and R' are independently selected from the group consisting of alkyl, cycloalkyl, aryl, heteroaryl (bonded through a ring carbon) and heteroalicyclic (bonded through a ring carbon), and where n is 0 or 1. An amide may be an amino acid or a peptide molecule attached to a molecule of the present invention, thereby forming a prodrug.

Any amine, hydroxy, or carboxyl side chain on the compounds of the present invention can be esterified or amidified. The procedures and specific groups to be used to achieve this end is known to those of skill in the art and can readily be found in reference sources such as Greene and Wuts, *Protec-* tive Groups in Organic Synthesis, 3rd Ed., John Wiley & Sons, New York, N.Y., 1999, which is incorporated herein in its entirety.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility over the parent drug. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Yet another example of a prodrug are protected thiol compounds. Thiols bearing hydrolyzable protecting groups can unmask protected SH groups prior to or simultaneous to use. As shown below, the moiety —C(O)—$R_E$ of a thioester may be hydrolyzed to yield a thiol and a pharmaceutically acceptable acid HO—C(O)—$R_E$.

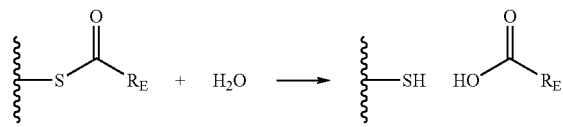

The term "thiol protecting group" refers to thiols bearing hydrolyzable protecting groups that can unmask protected SH groups prior to or simultaneous to use. Preferred thiol protecting groups include but are not limited to thiol esters which release pharmaceutically acceptable acids along with an active thiol moiety. Such pharmaceutically acceptable acids are generally nontoxic and do not abbrogate the biological activity of the active thiol moiety. Examples of pharmaceutically acceptable acids include, but are not limited to: N,N-diethylglycine; 4-ethylpiperazinoacetic acid; ethyl 2-methoxy-2-phenylacetic acid; N,N-dimethylglycine; (nitrophenoxysulfonyl)benzoic acid; acetic acid; maleic acid; fumaric acid; benzoic acid; tartraric acid; natural amino acids (like glutamate, aspartate, cyclic amino acids such proline); D-amino acids; butyric acid; fatty acids like palmitic acid, stearic acid, oleate; pipecolic acid; phosphonic acid; phosphoric acid; pivalate (trimethylacetic acid); succinic acid; cinnamic acid; anthranilic acid; salicylic acid; lactic acid; and pyruvic acids.

As used herein, the term "alkyl" refers to an aliphatic hydrocarbon group. The alkyl moiety may be a "saturated alkyl" group, which means that it does not contain any alkene or alkyne moieties. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 4 carbon atoms. The alkyl group of the compounds of the invention may be designated as "$C_1$-$C_5$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl.

The alkyl group may be substituted or unsubstituted. When substituted, any group(s) besides hydrogen can be the substituent group(s). When substituted, the substituent group(s) is(are) one or more group(s) individually and independently selected from the following non-limiting illustrative list: alkyl, cycloalkyl, aryl, heteroaryl, heterocycloalkyl, hydroxy, alkoxy, aryloxy, O, S, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. Each substituent group may be further substituted.

Unless otherwise indicated, when a group is described as "optionally substituted," it is meant that the group may be substituted with one or more substituents selected from the following non-limiting illustrative list: hydrogen, perhaloaryloxy, alkanoylalkyl, N-aryl-N-alkylamino, heterocyclylalkoxy, heterocyclylthio, hudroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamide, N-arylcarboxamidoalkoxy, cycloalkylcarbonyl, cyanoalkoxy, heterocyclylcarbonyl, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, haloalkylthio, alkanoyloxy, alkoxy, alkoxyalkyl, cycloalkoxy, cycloalkylalkoxy, hydroxyl, amino, thio, nitro, alkylamino, alkylthio, arylamino, aralkylamino, arylthio, arylthioalkyl, alkylsulfonyl, heteroarylthio, heteroarylsulfonyl, heterocyclylsulfonyl, arylsulphonyl, heteroarylsulfonyl, heterocyclylsulphonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkylenedioxy, haloalkylenedioxy, cycloalkyl, cycloalkylalkanoyl, halo, haloalkyl, haloalkoxy, hydroxyhaloalkyl, hydroxyhaloalkoxy, hydroxyalkyl, aryl, aryloxy, aralkoxy, saturated heterocyclyl, heteroaryl, heteroaryloxy, heteroaryloxyalkyl, heteroaralkyl, arylalkenyl, carboalkoxy, alkoxycarboxamido, alkylamidocarboylamido, arylamidocarboylamido, carboalkoxyalkyl, carboalkoxyalkenyl, carboamido, carboxamidoalkyl, cyanocycloalkylalkyl, cycloalkenyl, alkoxycarbonyl, aralkylthio, alkylthio, alkylsulfinyl, arylsulfinyl, dialkylamino, aminoalkyl, dialkylaminoalkyl, aminoaryl, alkylaminoaryl, acylamino, aminocarbonylalkoxy, aminocarbonylamino, aminothiocarbonylamino, aminothiocarbonylaminoalkyl.

Protecting groups that may form the protective derivatives of the substituents recited above are known to those of skill in the art and may be found in references such as Greene and Wuts, above. Each optional substituent may be further optionally substituted. Optionally substituted groups may be unsubstituted.

The term "halo" or, alternatively, "halogen" means fluoro, chloro, bromo or iodo. Preferred halo groups are fluoro, chloro and bromo. The terms "haloalkyl," "haloalkenyl," "haloalkynyl" and "haloalkoxy" include alkyl, alkenyl, alkynyl and alkoxy structures, that are substituted with one or more halo groups or with combinations thereof. The terms "fluoroalkyl" and "fluoroalkoxy" include haloalkyl and haloalkoxy groups, respectively, in which the halo is fluorine.

The term "hetero" in such terms as "heteroalkyl," "heteroalkenyl" "heteroalkynyl," "heterocycloalkyl," and "heteroaryl" refers to groups in which one or more of the backbone atoms is selected from an atom other than carbon, e.g., oxygen, nitrogen, sulfur, phosphorus or combinations thereof.

Cyclic alkyl moieties contain one or more covalently closed ring structures. Cyclic alkyl moieties can have a single ring (monocyclic) or two or more rings (polycyclic or multicyclic). Polycyclic groups include fused polycyclic groups wherein rings share adjacent pairs of backbone atoms, and linked cyclic groups wherein the rings are separate but linked. In fused polycyclic groups, rings may share adjacent carbon atoms, or may share non-carbon atoms such as N. Linked polycyclic groups may be connected by a bond or a linker. Polycyclic groups can be linked by an optionally substituted alkyl moiety including but not limited to saturated alkyl linkers, or unsaturated alkyl linkers such as alkylene (e.g., methylene, ethylene, or propylene) or alkynylene linkers.

The term "carbocyclic" refers to a compound which contains one or more covalently closed ring structures, wherein the atoms forming the backbone of the ring are all carbon atoms. The term "heterocyclic" refers to a compound with contains one or more covalently closed ring structures, wherein at least one ring backbone contains at least one atom which is different from carbon. Generally, heterocyclic groups can contain one to four heteroatoms, each selected from O, S and N, wherein each ring has from 4 to 10 atoms in the ring. Generally, heterocyclic rings do not contain two adjacent O or S atoms. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl.

The term "cycloalkyl" refers to an aliphatic cyclic alkyl moiety wherein the ring is either completely saturated, partially unsaturated, or fully unsaturated, wherein if there is unsaturation, the conjugation of the pi-electrons in the ring do not give rise to aromaticity. The term "cycloalkyl" may refer to a monocyclic or polycyclic group. Cycloalkyl groups may be fused or linked to other cyclic alkyl moieties. A cycloalkyl group may be optionally substituted. Preferred cycloalkyl groups include groups having from three to twelve ring atoms, more preferably from 5 to 10 ring atoms. The term "carbocyclic cycloalkyl" refers to a monocyclic or polycyclic cycloalkyl group which contains only carbon and hydrogen. The term "heterocycloalkyl" refers to a monocyclic or polycyclic cycloalkyl group wherein at least one ring backbone contains at least one atom which is different from carbon. Illustrative examples of carbocyclic cycloalkyl groups include the following moieties:

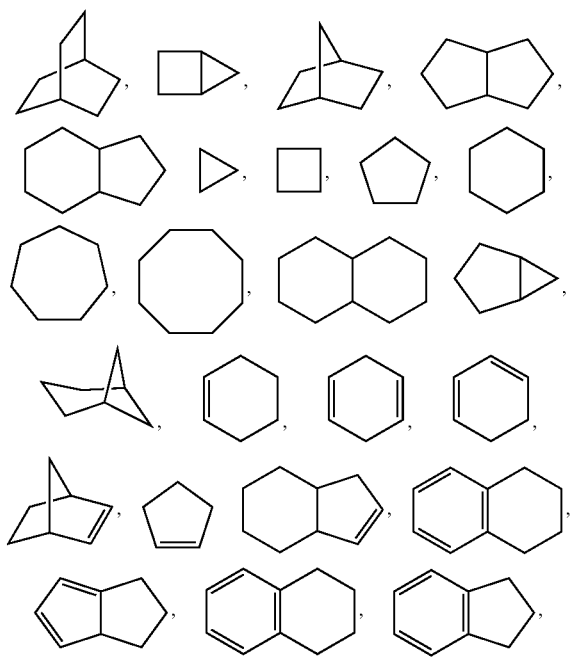

and the like.

A heterocycloalkyl group refers to a cycloalkyl group that includes at least one heteroatom selected from nitrogen, oxygen and sulfur. Heterocycloalkyl groups may be fused with one or more aryl, heteroaryl, cycloalkyl, or heterocycloalkyl groups. Heterocycloalkyl groups may be linked with one or more aryl, heteroaryl, cycloalkyl, or heterocycloalkyl groups. Examples of heterocycloalkyl (non-aromatic heterocyclic groups) are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, titanic, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Illustrative examples of heterocycloalkyl groups include:

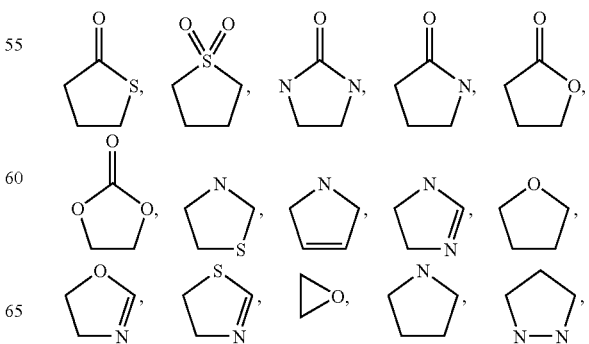

-continued

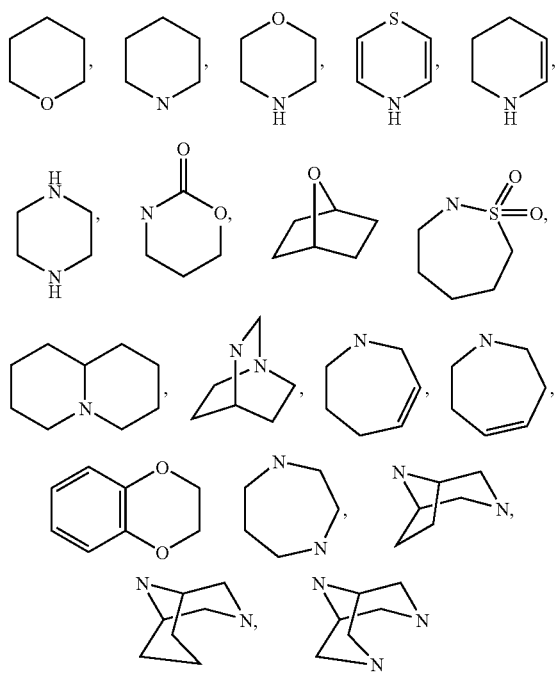

and the like.

The terms "aryl" or "aromatic" refer to a group which has at least one ring having a conjugated pi electron system. Aryl groups can be carbocyclic aryl groups or heteroaryl groups. The term "carbocyclic aryl" refers to a group (e.g., phenyl) in which all ring backbone atoms are carbon. The terms "heteroaryl" or "heteroaromatic" refer to an aryl (aromatic) group that includes one or more ring heteroatoms selected from nitrogen, oxygen and sulfur. Aryl groups may be optionally substituted. Aryl groups may be monocyclic or polycyclic. Polycyclic aryl groups may be fused or linked. Polycyclic aryl groups can be fused or linked to aryl groups or cycloalkyl groups.

Examples of heteroaryl groups include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Polycyclic heteroaryl groups may be attached through carbon ring backbone atoms, or may be attached through ring backbone heteroatoms, especially N, depending on structure of the group. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). Polycyclic heteroaryl groups include benzo-fused ring systems and ring systems substituted with one or two oxo (=O) moieties such as pyrrolidin-2-one.

Illustrative examples of heteroaryl groups include the following moieties:

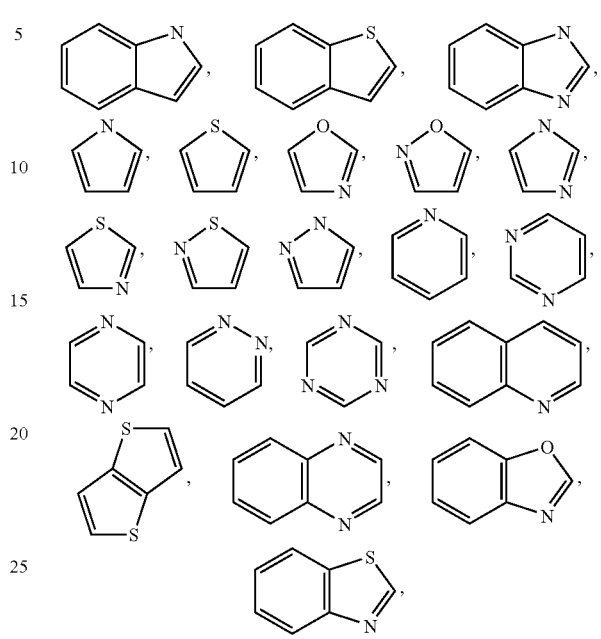

and the like.

The substituent "R" appearing by itself and without a number designation refers to a substituent selected from the group consisting of optionally substituted alkyl, including optionally substituted alkenyl or alkynyl, optionally substituted cycloalkyl, optionally substituted aryl, optionally substituted heteroaryl (bonded through a ring carbon) and optionally substituted hetercycloalkyl (bonded through a ring carbon).

An "O-carboxy" group refers to a RC(=O)O— group, where R is as defined herein.

A "C-carboxy" group refers to a —C(=O)OR groups where R is as defined herein.

An "acyl" group refers to a —C(=O)R group.

An "acetyl" group refers to a —C(=O)CH$_3$, group.

A "trihalomethanesulfonyl" group refers to a X$_3$CS(=O)$_2$— group where X is a halogen.

A "cyano" group refers to a —CN group.

An "isocyanato" group refers to a —NCO group.

A "thiocyanato" group refers to a —CNS group.

An "isothiocyanato" group refers to a —NCS group.

A "sulfinyl" group refers to a —S(=O)—R group, with R as defined herein.

A "S-sulfonamido" group refers to a —S(=O)$_2$NR, group, with R as defined herein.

A "N-sulfonamido" group refers to a RS(=O)$_2$NH— group with R as defined herein.

A "trihalomethanesulfonamido" group refers to a X$_3$CS(=O)$_2$NR— group with X and R as defined herein.

An "O-carbamyl" group refers to a —OC(=O)—NR, group-with R as defined herein.

An "N-carbamyl" group refers to a ROC(=O)NH— group, with R as defined herein.

An "O-thiocarbamyl" group refers to a —OC(=S)—NR, group with R as defined herein.

An "N-thiocarbamyl" group refers to an ROC(=S)NH— group, with R as defined herein.

A "C-amido" group refers to a —C(=O)—NR$_2$ group with R as defined herein.

An "N-amido" group refers to a RC(=O)NH— group, with R as defined herein.

The term partially halogenated alkyl refers to an alkyl group having both hydrogen and halogen substituents.

The term "perhaloalkyl" refers to an alkyl group where all of the hydrogen atoms are replaced by halogen atoms.

The term "lower perfluoroalkoxy" refers to a radical —O—(CX$_2$)$_n$CX$_3$ where X is any halogen, preferable F or Cl, and n is 1-5.

When two substituents taken together along with the two ring carbons to which they are attached form a ring, it is meant that the following structure:

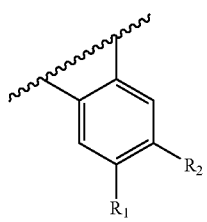

is, for example, representative of a structure such as the following:

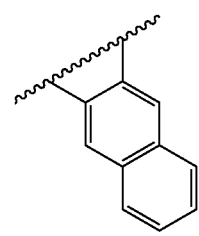

In the above example, R$_1$ and R$_2$, taken together along with the two ring carbons to which they are attached, form a six-membered aromatic ring.

Solubility is a thermodynamic parameter and plays an important role in the determonation of a drug's bioavailability. Since a drug must be soluble in the gastrointestinal fluid to be orally active, the rate and extent of dissolution depend critically upon intrinsic water solubility (neutral species solubility) (Dressman, J.; Amindo, G. L.,; Reppas, C.; Shah. V. P. *Pharm. Res.*, 1998, 15, 11.) Experimental and computational approaches to estimate solubility and permeability in drug discovery and development setting have been described (Lipinski C. A. et al. 1997 *Adv. Drug Deliv. Rev.* 23, 3-25) *Adv. Drug Deliv. Rev.* 23, 3-25 ). Traditional analytical methods define solubility as the concentration of material in solution at equilibrium with its solid form. In this method a compound is extensively shaken in the buffer of choice, filtered through a micropore membrane, and the concentration of dissolved compound in the filtrate determined. This approach results in a thermodynamic solubility assessment. For discovery, it is beneficial to measure kinetic solubility in which a compound DMSO solution is added to aqueous buffer. Several high throughput approaches for solubility have been described, e.g. turbidimetric method (Bevan, C. and Lloyd, R. S. *Anal. Chem.* 2000 72, 1781-1787), nephelometric method (Avdeef, A. (2001) High throughput measurements of solubility profiles. In *Pharmacokinetic Optimization in Drug Research; Biological, Physicochemical, And Computational Strategies* (Testa, B. et al., eds), pp. 305-326, Verlag Helvitica Chimica Actaand). Measurement of solubility at multiple pH levels (pH 1-8), is more useful that a single pH, since many drug candidates contain ionizable groups. A solubility-pH profile provides the pH gradient of the gastrointestinal tract.

Accurate understanding of a compound's solubility is also necessary to not only prepare and dispense formulations, but also to evaluate new chemical series and provide feedback to drive synthetic optimization. Structural series of compounds are synthesized with the aim of improving solubility by the addition of various chemical moieties. Structural elements known to confer aqueous solubility on otherwise insoluble molecular entities include but are not limited to N-piperazinylethyl, N-morpholinylethyl, 1,3-dihydroxy-2N-propanoyl moieties. Common solubilizing groups often incorporated in synthetic approaches to improve solubility of molecules include amine functionality, such as dimethylamino, diethylamino, piperazinyl, N-methyl-N-isopropylamino, morpholino, pyrrolidino moieties, or groups bearing aliphatic alcohol functionality, such as that found in ethanolamine or glycerol.

In certain embodiments of the invention, a structural element known to confer aqueous solubility is incorporated in a compound of the invention. Such structural elements are preferably attached to synthetically accessible regions of the compound. In certain embodiments, such structural elements are attached to or incorporate synthetically available N atoms in amine or amide or sulfonamide moieties of the compound. In certain embodiments a solubilizing group is attached to or incorporates a N atom and is chosen from the group consisting of dimethylamino, diethylamino, piperazinyl, N-methyl-N-isopropylamino, morpholino, pyrrolidino moieties, or groups bearing aliphatic alcohol functionality, such as that found in ethanolamine or glycerol.

In certain embodiments, the invention relates to a compound of Formula I where R$_1$-R$_5$ are hydrogen.

In other embodiments R$_2$ is an alkoxy. The alkoxy may be selected from the group consisting of methoxy, ethoxy, propoxy, n-butoxy, t-butoxy, and isobutoxy. In some embodiments, R$_3$ is an alkoxy.

In certain embodiments, R$_3$ is a halogen. "Halogen" refers to a substituent selected from the group consisting of fluorine, chlorine, bromine, and iodine. Thus, in some embodiments the halogen may be chlorine, whereas in other embodiments, the halogen may be bromine or fluorine. In still other embodiments, R$_3$ is a perhaloalkyl. The perhaloalkyl may be selected from the group consisting of trifluoromethyl, pentafluoroethyl, and heptafluoropropyl.

In some embodiments, R$_3$ is a heterocyclylic ring. The heterocyclylic ring may be selected from the group consisting of furan, thiophene, pyrrole, pyrroline, pyrrolidine, oxazole, thiazole, imidazole, imidazoline, imidazolidine, pyrazole, pyrazoline, pyrazolidine, isoxazole, isothiazole, triazole, thiadiazole, pyran, pyridine, piperidine, morpholine, thiomorpholine, pyridazine, pyrimidine, pyrazine, piperazine, triazine,

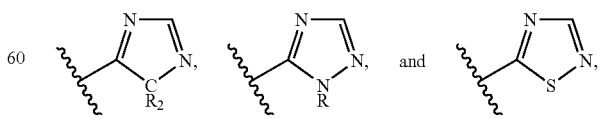

where R is as defined herein. In some embodiments the heterocyclyl is pyrrolidine, whereas in other embodiments, the heterocyclyl is morpholine.

In certain embodiments, R$_3$ is —NH(CO)R, where R is as defined herein. In some embodiments, R is selected from hydrogen, and lower alkyl, where the alkyl may be selected from the group consisting of methyl, ethyl, propyl, n-butyl, t-butyl, and isobutyl.

In some embodiments, R$_2$ and R$_3$, taken together along with the two ring carbons to which they are attached form a six-membered heterocyclic ring. In certain of these embodiments, the six-membered heterocyclic ring has the following structure:

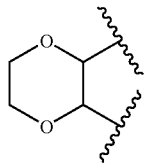

Thus, in some embodiments, the compound of Formula I will have the following structure:

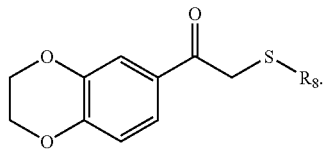

In some embodiments R$_3$ or R$_4$ is an optionally substituted N-sulfonamido or an optinally substituted S-sulfonamido.

In some embodiments R$_3$ or R$_4$ has the structure

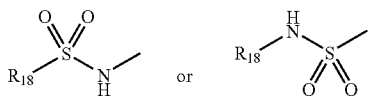

wherein R$_{18}$ is selected from the group consisting of optionally substituted aryl_and optionally substituted heteroaryl.

In some embodiments R$_{18}$ is phenyl, singly or multiply substituted with C$_{1-5}$ alkyl, C$_{1-5}$ perhaloalkyl, C$_{1-5}$ alkoxy, C$_{1-5}$ perhaloalkyl alkoxy, and N-alkylamido.

In some embodiments R$_6$ and R$_7$ are hydrogen.

In certain embodiments, R$_8$ is cyano. In other embodiments, R$_8$ is

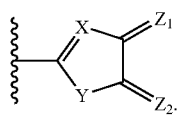

In some of these embodiments, X is nitrogen, Y is oxygen and Z$_1$ and Z$_2$ are H$_2$, whereas in other embodiments, X is nitrogen, Y is NH, Z$_1$ is oxygen and Z$_2$ is H$_2$. In still other embodiments, X is nitrogen, Y is NH, and Z$_1$ and Z$_2$ are oxygen, while in other embodiments, X is nitrogen, Y is sulfur, Z$_1$ is (H)(OH) and Z$_2$ is H$_2$.

When Z$_1$ or Z$_2$ are H$_2$, it is meant that the ring carbon to which Z$_1$ or Z$_2$ are attached forms a methylene (—CH$_2$—) group. When Z$_1$ or Z$_2$ are oxygen, it is meant that the ring carbon to which Z$_1$ or Z$_2$ are attached forms a carbonyl (—C(O)—) group. When Z$_1$ or Z$_2$ are (H)(OH), it is meant that the ring carbon to which Z$_1$ or Z$_2$ are attached forms a hydroxymethylene (—CH(OH)—) group.

In certain other embodiments, R$_8$ is

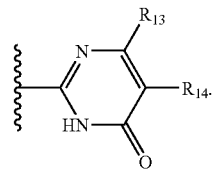

In some of these embodiments, R$_{13}$ and R$_{14}$ are hydrogen, whereas in other embodiments, R$_{13}$ is lower alkyl and R$_{14}$ are hydrogen, where the alkyl may be selected from the group consisting of methyl, ethyl, propyl, n-butyl, t-butyl, and isobutyl.

In certain embodiments, the present invention relates to a compound of Formula I where T is sulfur. In other embodiments, T is oxygen, whereas in yet other embodiments, T is —NR.

In certain embodiments of compounds of the invention, Q is a bond.

In certain embodiments of compounds of the invention where Q is a bond, T is S.

In certain embodiments of compounds of the invention where Q is a bond and T is S, R6 and R7 are both H or are both methyl.

In certain embodiments of compounds of the invention where Q is a bond, T is S and R6 and R7 are both H or are both methyl, R$_3$ is selected from the group consisting of N-sulfonamido and S-sulfonamido.

In certain embodiments of compounds of the invention where Q is a bond, T is S, R6 and R7 are both H or are both methyl and R$_3$ is selected from the group consisting of N-sulfonamido and S-sulfonamido, R$_1$, R$_2$, R$_4$, and R$_5$ are hydrogen.

In certain embodiments of compounds of the invention where Q is a bond, T is S, R6 and R7 are both H or are both methyl and R$_3$ is selected from the group consisting of N-sulfonamido and S-sulfonamido and R$_1$, R$_2$, R$_4$, and R$_5$ are hydrogen, G2 is a bond, methylene, or ethylene.

In certain embodiments of compounds of the invention, G1 is an optionally substituted fused polycyclic aryl.

In certain embodiments of compounds of the invention, G1 is an optionally substituted naphthyl.

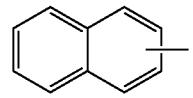

In certain embodiments of compounds of the invention, G1 is an optionally substituted naphthyl and the naphthyl is optionally singly or multiply substituted with substituents independently chosen from a set of substituents {K}, which is the group consisting of hydrogen, perhaloaryloxy, alkanoylalkyl, N-aryl-N-alkylamino, heterocyclylalkoxy, heterocyclylthio, hudroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamide, N-arylcarboxamidoalkoxy, cycloalkylcarbonyl, cyanoalkoxy, heterocyclylcarbonyl, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, haloalkylthio, alkanoyloxy, alkoxy, alkoxyalkyl, cycloalkoxy, cycloalkylalkoxy, hydroxyl, amino, thio, nitro, alkylamino, alkylthio, arylamino, aralkylamino, arylthio, arylthioalkyl, alkylsulfonyl, heteroarylthio, heteroarylsulfonyl, heterocyclylsulfonyl, arylsulphonyl, heteroarylsulfonyl, heterocyclylsulphonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkylenedioxy, haloalkylenedioxy, cycloalkyl, cycloalkylalkanoyl, halo, haloalkyl, haloalkoxy, hydroxyhaloalkyl, hydroxyhaloalkoxy, hydroxyalkyl, aryl, aryloxy, aralkoxy, saturated heterocyclyl, heteroaryl, heteroaryloxy, heteroaryloxyalkyl, heteroaralkyl, arylalkenyl, carboalkoxy, alkoxycarboxamido, alkylamidocarboylamido, arylamidocarboylamido, carboalkoxyalkyl, carboalkoxyalkenyl, carboamido, carboxamidoalkyl, cyanocycloalkylalkyl, cycloalkenyl, alkoxycarbonyl, aralkylthio, alkylthio, alkylsulfinyl, arylsulfinyl, dialkylamino, aminoalkyl, dialkylaminoalkyl, aminoaryl, alkylaminoaryl, acylamino, aminocarbonylalkoxy, aminocarbonylamino, aminothiocarbonylamino, aminothiocarbonylaminoalkyl.

In certain embodiments of compounds of the invention, G1 is an optionally substituted naphthyl, the naphthyl is optionally singly or multiply substituted with substituents independently chosen from the group {K}, Q is a bond, T is S, and R6 and R7 are both H.

In certain embodiments of compounds of the invention, G1 is an optionally substituted naphthyl, the naphthyl is optionally singly or multiply substituted with substituents independently chosen from the group {K}, Q is a bond, T is S, R6 and R7 are both H, and $R_3$ is selected from the group consisting of N-sulfonamido and S-sulfonamido.

In certain embodiments of compounds of the invention, G1 is an optionally substituted naphthyl, the naphthyl is optionally singly or multiply substituted with substituents independently chosen from the group {K}, Q is a bond, T is S, R6 and R7 are both H, $R_3$ is selected from the group consisting of N-sulfonamido and S-sulfonamido, and $R_1$, $R_2$, $R_4$ and $R_5$ are hydrogen.

In certain embodiments of compounds of the invention, G1 is an optionally substituted naphthyl, the naphthyl is optionally singly or multiply substituted with substituents independently chosen from the group {K}, Q is a bond, T is S, R6 and R7 are both H, $R_3$ is selected from the group consisting of N-sulfonamido and S-sulfonamido, $R_1$, $R_2$, $R_4$ and $R_5$ are hydrogen, and G2 is a bond, methylene, or ethylene.

In certain embodiments of compounds of the invention, G1 is an optionally substituted naphthyl, the naphthyl is optionally singly or multiply substituted with substituents independently chosen from the group {K}, Q is a bond, T is S, R6 and R7 are both H, $R_3$ is selected from the group consisting of N-sulfonamido and S-sulfonamido, $R_1$, $R_2$, $R_4$ and $R_5$ are hydrogen, G2 is a bond, methylene, or ethylene, and the compound has a structure selected from a group consisting of:

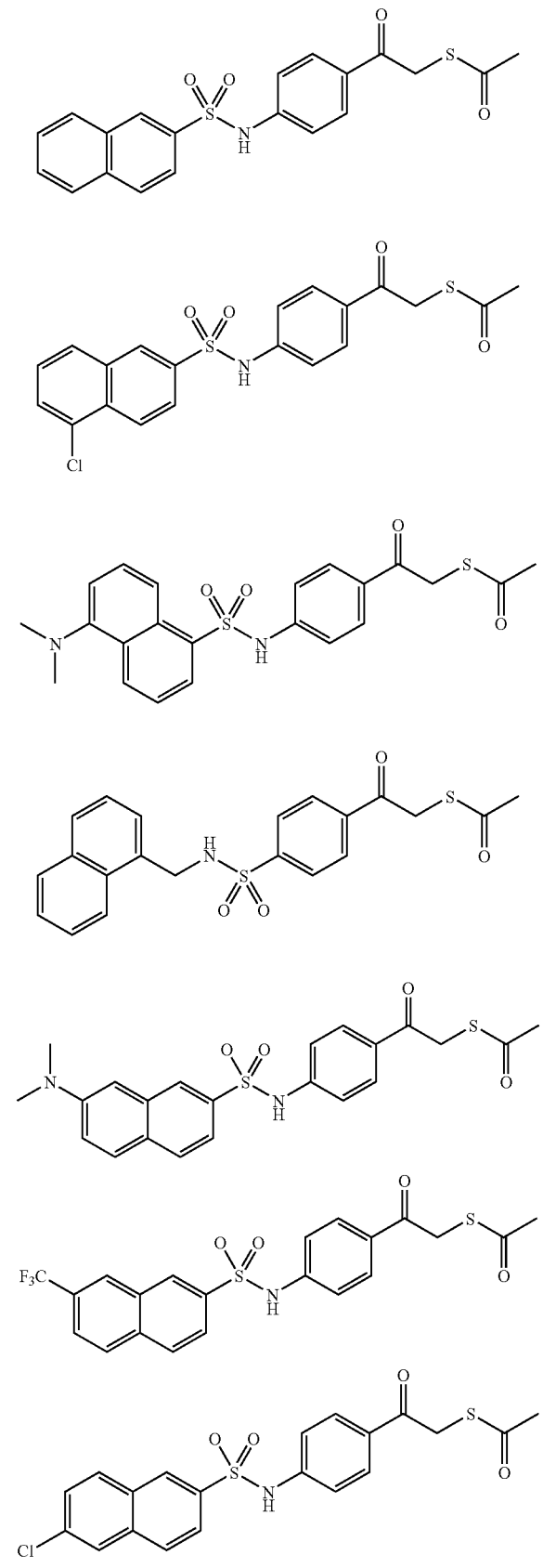

-continued
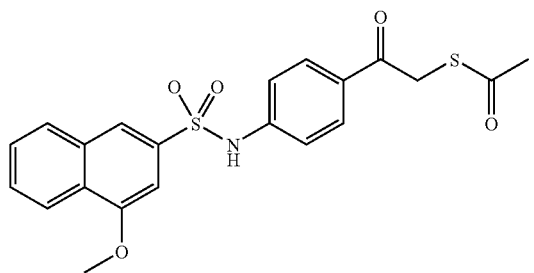
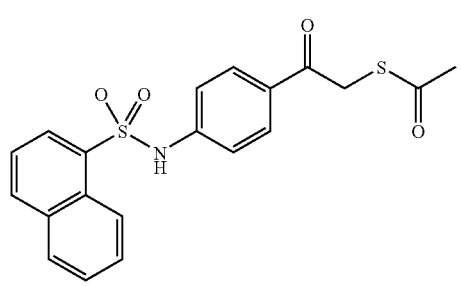
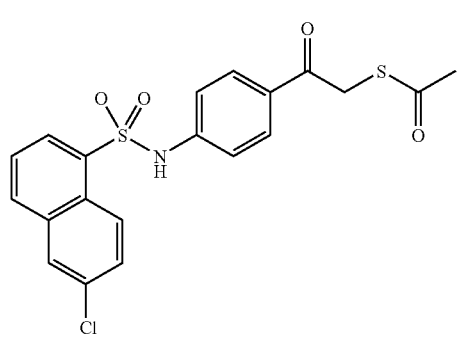
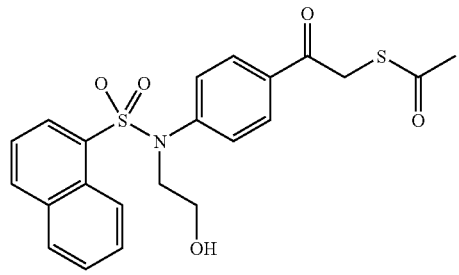
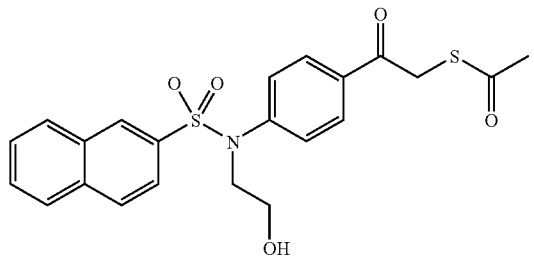
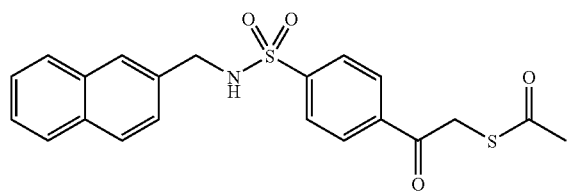
-continued
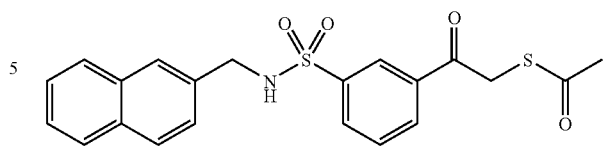
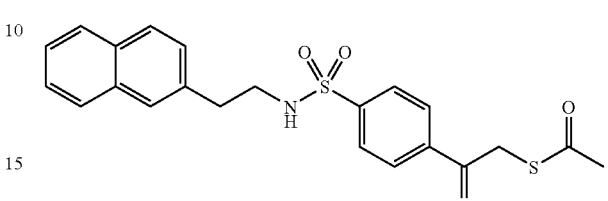
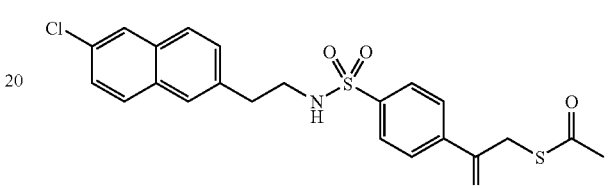
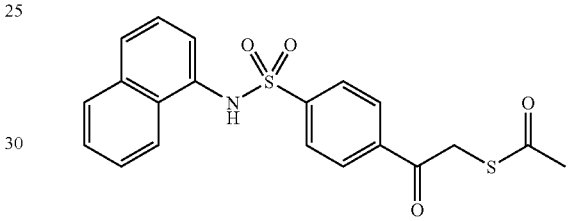
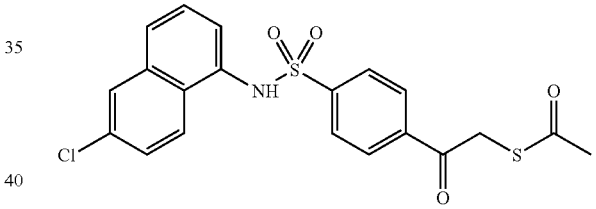
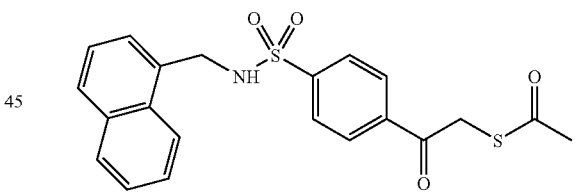
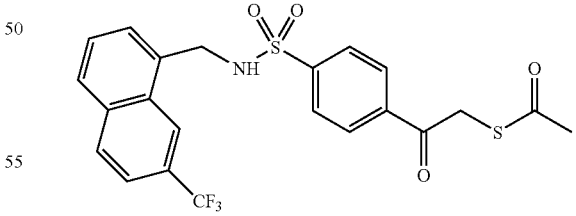
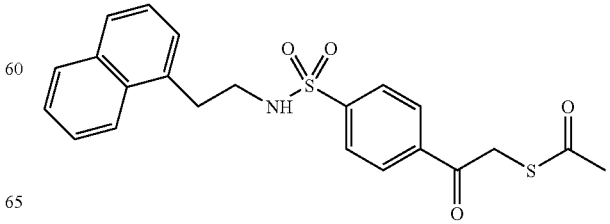

-continued

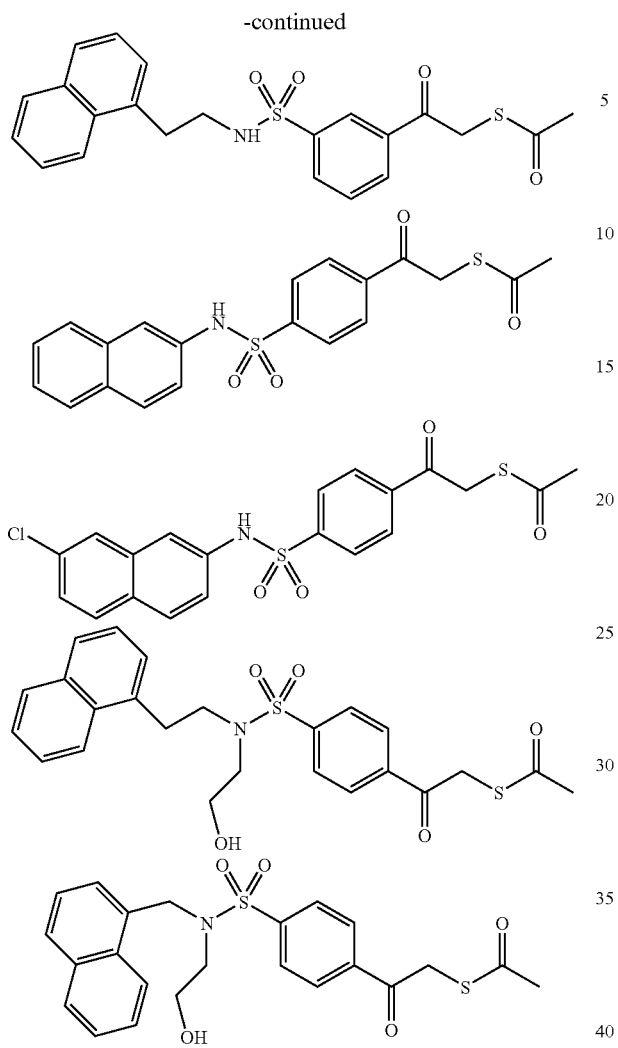

In certain embodiments of compounds of the invention, G1 is an optionally substituted naphthyl, the naphthyl is optionally singly or multiply substituted with substituents independently chosen from the group {K}, Q is a bond, T is S, R6 and R7 are both H and $R_2$ is selected from the group consisting of N-sulfonamido and S-sulfonamido.

In certain embodiments of compounds of the invention, G1 is an optionally substituted naphthyl, the naphthyl is optionally singly or multiply substituted with substituents independently chosen from the group {K}, Q is a bond, T is S, R6 and R7 are both H, $R_2$ is selected from the group consisting of N-sulfonamido and S-sulfonamido and the compound has a structure selected from a group consisting of:

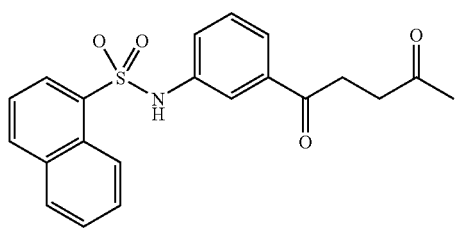

-continued

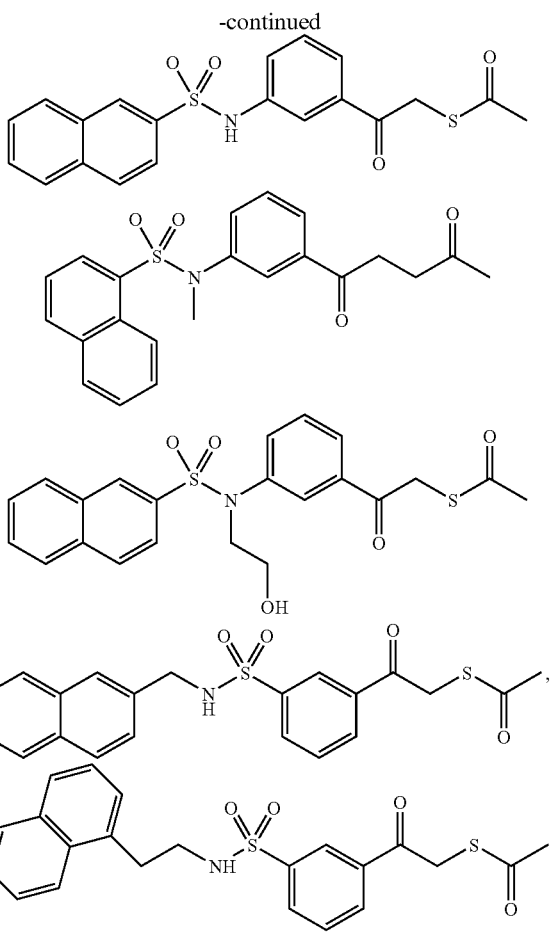

In certain embodiments of compounds of the invention, G1 is an optionally substituted fused polycyclic heteroaryl.

In certain embodiments of compounds of the invention, G1 is an optionally substituted fused polycyclic heteroaryl selected from the set of substituents {L} which is the group consisting of:

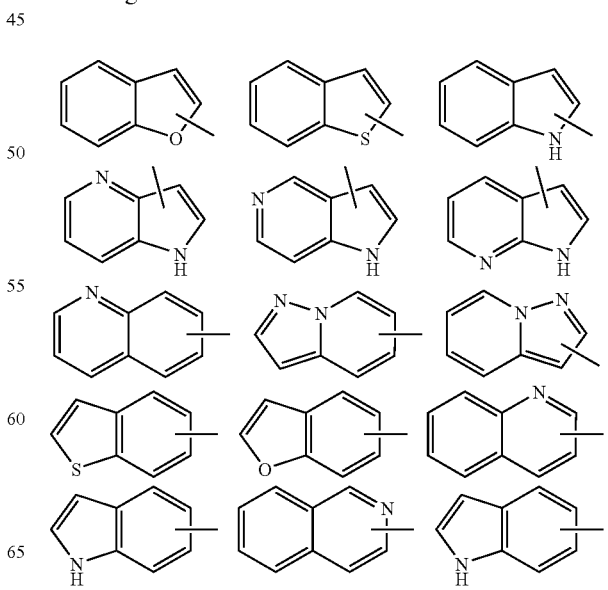

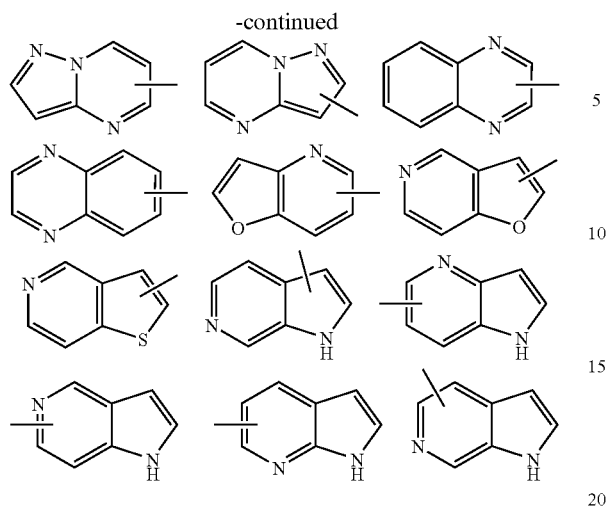

In certain embodiments of compounds of the invention, G1 is an optionally substituted fused polycyclic heteroaryl selected the group {L} and G1 is optionally singly or multiply substituted with substituents independently chosen from the group {K}.

In certain embodiments of compounds of the invention, G1 is an optionally substituted fused polycyclic heteroaryl selected from group {L} and G1 is optionally singly or multiply substituted with substituents independently chosen from the group {K}, and Q is a bond, T is S, and R6 and R7 are both H In certain embodiments of compounds of the invention, G1 is an optionally substituted fused polycyclic heteroaryl selected from the group {L} and G1 is optionally singly or multiply substituted with substituents independently chosen from the group {K}, Q is a bond, T is S, R6 and R7 are both H and $R_3$ is selected from the group consisting of N-sulfonamido and S-sulfonamido.

In certain embodiments of compounds of the invention, G1 is an optionally substituted fused polycyclic heteroaryl selected from the group {L} and G1 is optionally singly or multiply substituted with substituents independently chosen from the group {K}, Q is a bond, T is S, R6 and R7 are both H, $R_3$ is selected from the group consisting of N-sulfonamido and S-sulfonamido and $R_1$, $R_2$, $R_4$, and $R_5$ are hydrogen.

In certain embodiments of compounds of the invention, G1 is an optionally substituted fused polycyclic heteroaryl selected from the group {L} and G1 is optionally singly or multiply substituted with substituents independently chosen from the group {K}, Q is a bond, T is S, R6 and R7 are both H, $R_3$ is selected from the group consisting of N-sulfonamido and S-sulfonamido, $R_1$, $R_2$, $R_4$ and $R_5$ are hydrogen and G2 is a bond, methylene, or ethylene.

In certain embodiments of compounds of the invention, G1 is an optionally substituted fused polycyclic heteroaryl selected from the group {L} and G1 is optionally singly or multiply substituted with substituents independently chosen from the group {K}, Q is a bond, T is S, R6 and R7 are both H, $R_3$ is selected from the group consisting of N-sulfonamido and S-sulfonamido, $R_1$, $R_2$, $R_4$ and $R_5$ are hydrogen, G2 is a bond, methylene, or ethylene and the compound has the structure selected from a group consisting of:

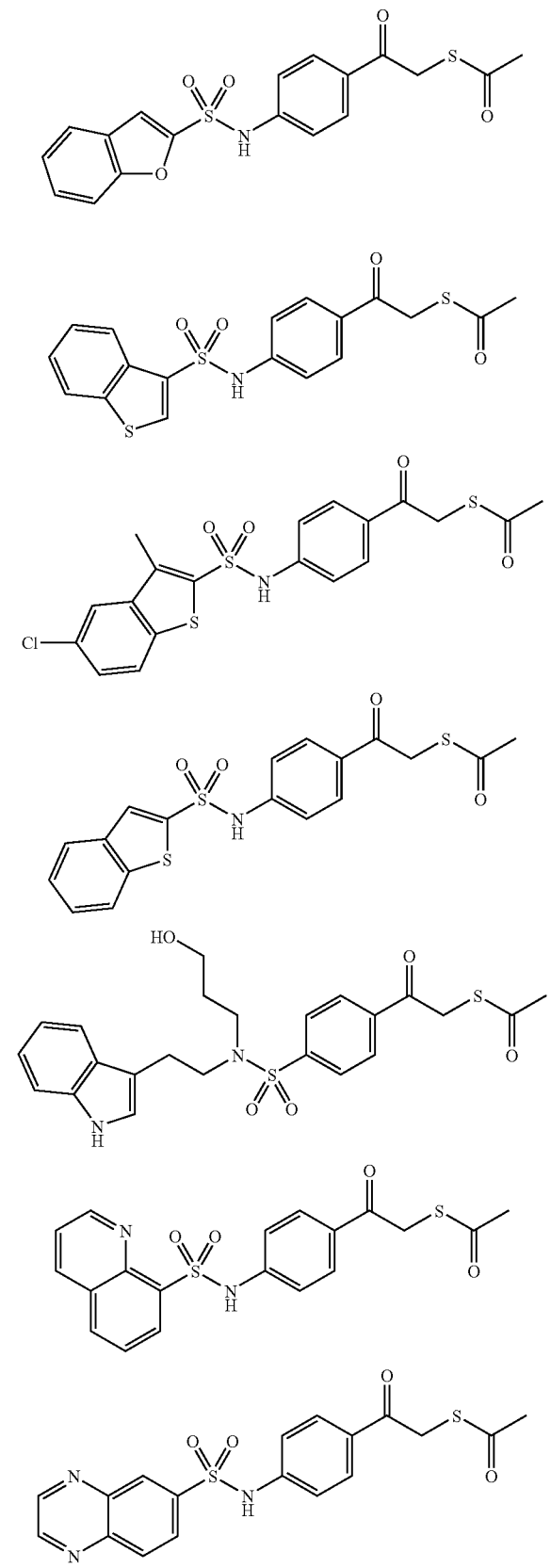

-continued
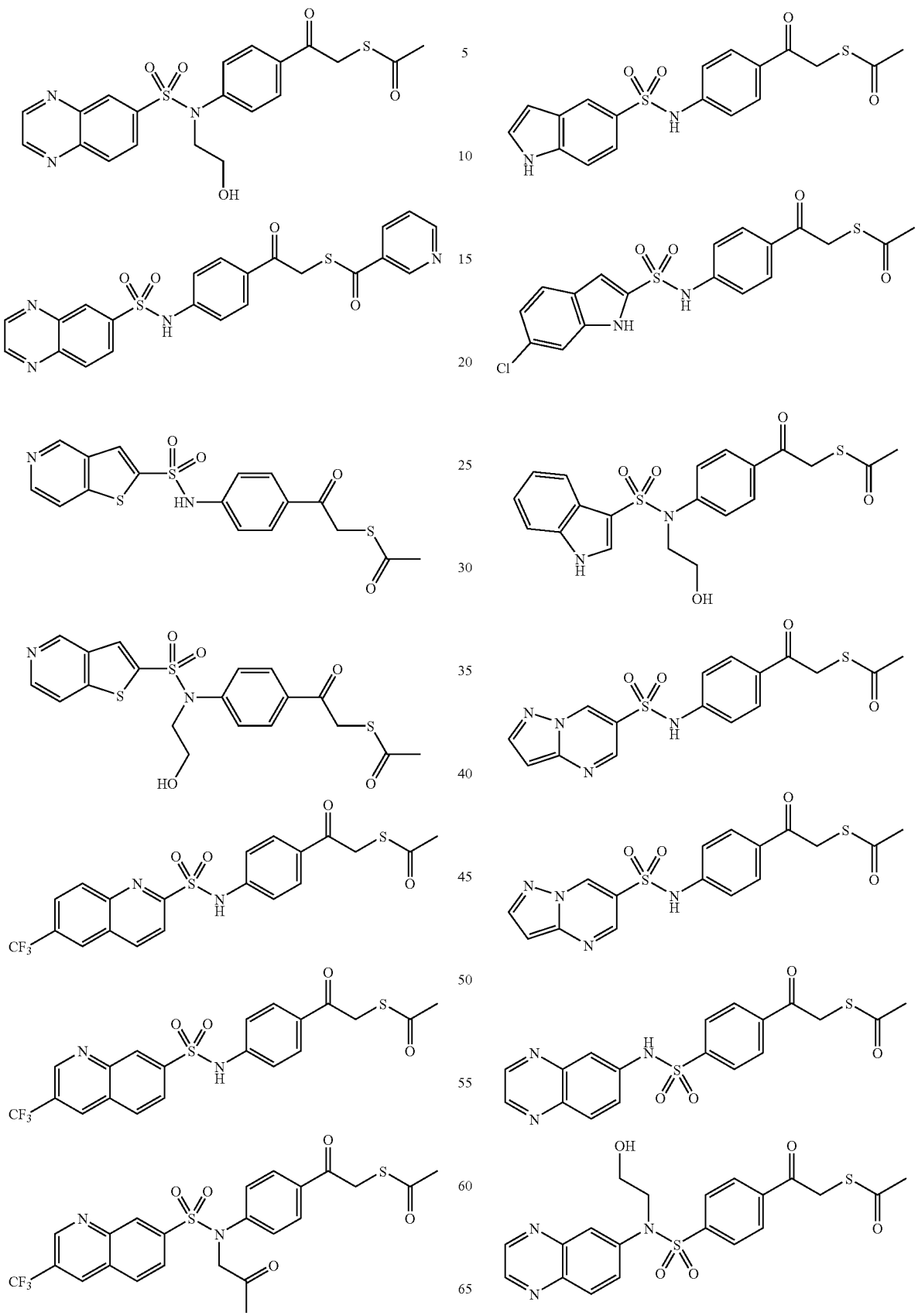

-continued

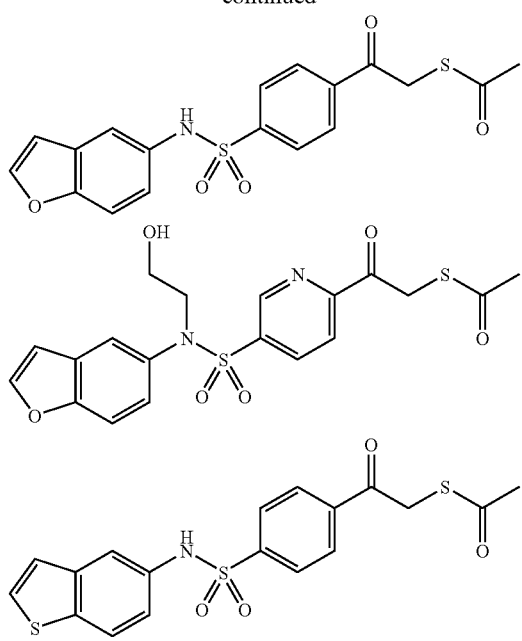

In certain embodiments of compounds of the invention, G1 is an optionally substituted naphthyl, the naphthyl is optionally singly or multiply substituted with substituents independently chosen from the group {K}, Q is a bond, T is S, R6 and R7 are both H, and R₂ is selected from the group consisting of N-sulfonamido and S-sulfonamido.

In certain embodiments of compounds of the invention, G1 is an optionally substituted naphthyl, the naphthyl is optionally singly or multiply substituted with substituents independently chosen from the group {K}, Q is a bond, T is S, R6 and R7 are both H, R₂ is selected from the group consisting of N-sulfonamido and S-sulfonamido and the compound has the structure selected from a group consisting of:

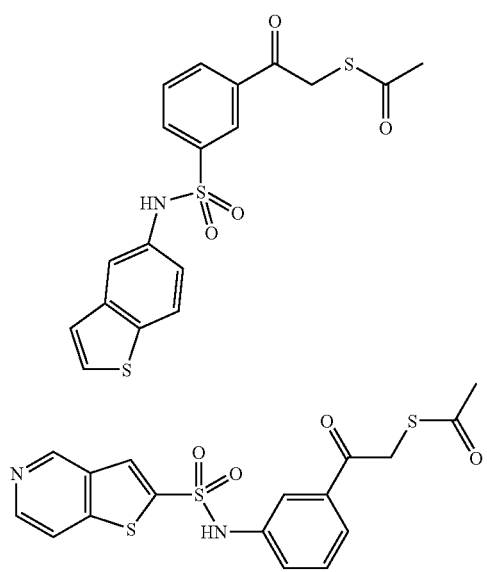

In certain embodiments of compounds of the invention, Q is a bond and G1 is an optionally substituted polycyclic aryl and cycloalkyl ring.

In certain embodiments of compounds of the invention, Q is a bond and G1 is an optionally substituted polycyclic aryl and cycloalkyl ring, which is selected from a group consisting of:

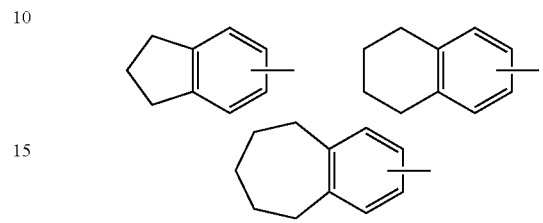

In certain embodiments of compounds of the invention, Q is a bond and G1 is an optionally substituted polycyclic aryl and cycloalkyl ring, which is selected from a group consisting of:

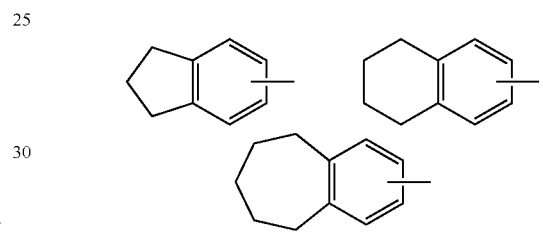

and G1 is optionally singly or multiply substituted with substituents independently chosen from the group {K}.

In certain embodiments of compounds of the invention, Q is a bond and G1 is an optionally substituted polycyclic aryl and cycloalkyl ring, which is selected from a group consisting of:

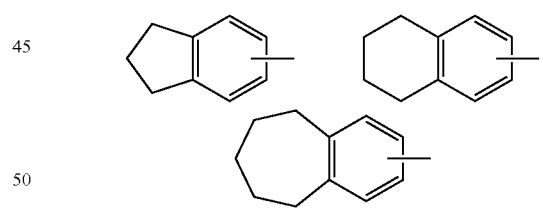

and G1 is optionally singly or multiply substituted with substituents independently chosen from the group {K}, Q is a bond, T is S and R6 and R7 are both H.

In certain embodiments of compounds of the invention, Q is a bond and G1 is an optionally substituted polycyclic aryl and cycloalkyl ring, which is selected from a group consisting of:

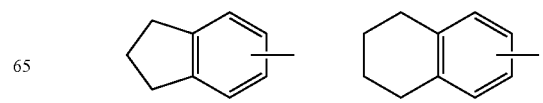

-continued

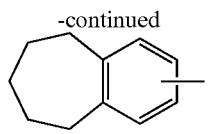

and G1 is optionally singly or multiply substituted with substituents independently chosen from the group {K}, Q is a bond, T is S and R6 and R7 are both H and $R_2$ or $R_3$ is selected from the group consisting of N-sulfonamido and S-sulfonamido.

In certain embodiments of compounds of the invention, Q is a bond and G1 is an optionally substituted polycyclic aryl and cycloalkyl ring, which is selected from a group consisting of:

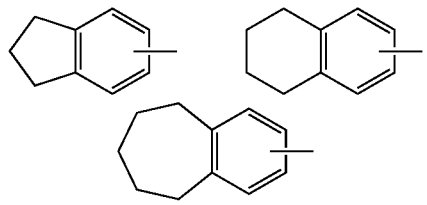

and G1 is optionally singly or multiply substituted with substituents independently chosen from the group {K}, Q is a bond, T is S and R6 and R7 are both H, $R_2$ or $R_3$ is selected from the group consisting of N-sulfonamido and S-sulfonamido and $R_1$, $R_4$, and $R_5$ are hydrogen and wherein one of $R_2$ and $R_3$ are hydrogen.

In certain embodiments of compounds of the invention, Q is a bond and G1 is an optionally substituted polycyclic aryl and cycloalkyl ring, which is selected from a group consisting of:

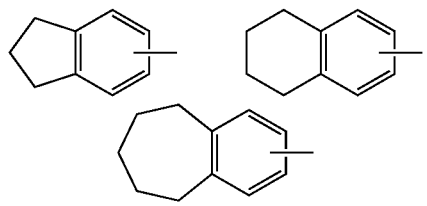

and G1 is optionally singly or multiply substituted with substituents independently chosen from the group {K}, Q is a bond, T is S and R6 and R7 are both H, $R_2$ or $R_3$ is selected from the group consisting of N-sulfonamido and S-sulfonamido, $R_1$, $R_4$, and $R_5$ are hydrogen and wherein one of $R_2$ and $R_3$ are hydrogen, and G2 is a bond, methylene, or ethylene.

In certain embodiments of compounds of the invention, Q is a bond and G1 is an optionally substituted polycyclic aryl and cycloalkyl ring, which is selected from a group consisting of:

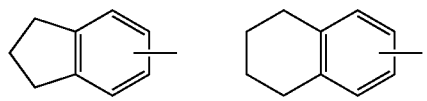

-continued

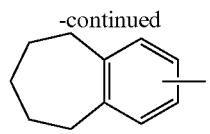

and G1 is optionally singly or multiply substituted with substituents independently chosen from the group {K}, Q is a bond, T is S and R6 and R7 are both H, $R_2$ or $R_3$ is selected from the group consisting of N-sulfonamido and S-sulfonamido, $R_1$, $R_4$, and $R_5$ are hydrogen, wherein one of $R_2$ and $R_3$ are hydrogen, G2 is a bond, methylene, or ethylene and the compound has the structure selected from a group consisting of:

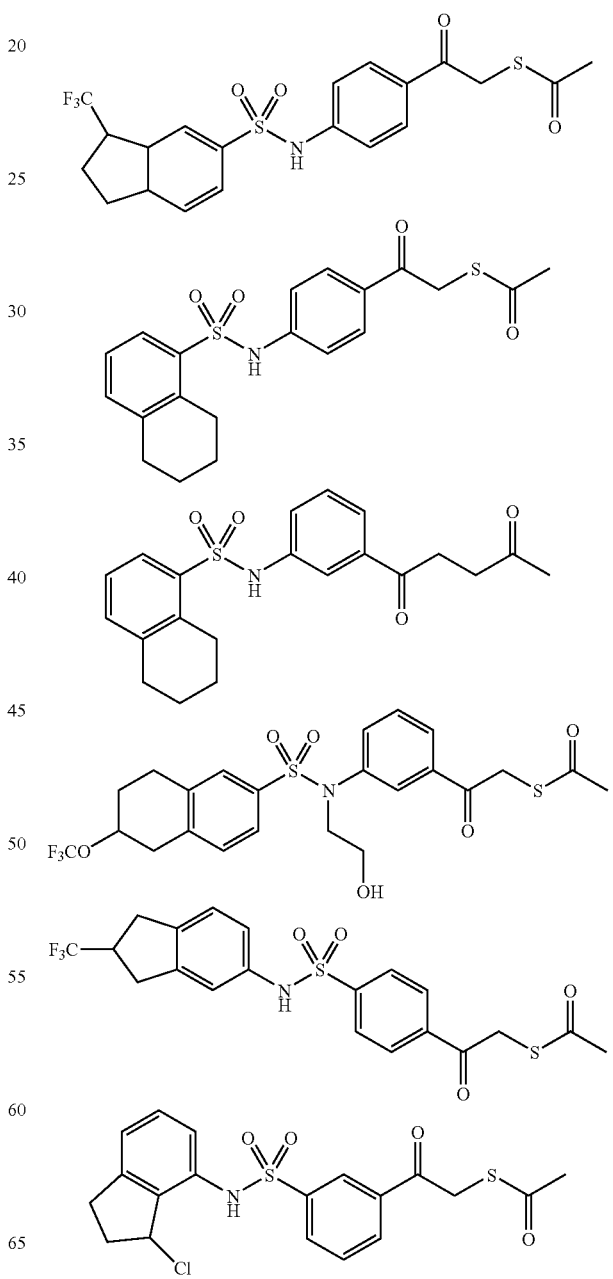

-continued

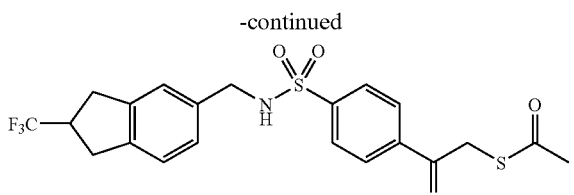
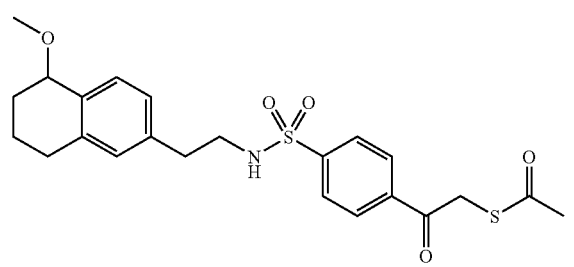
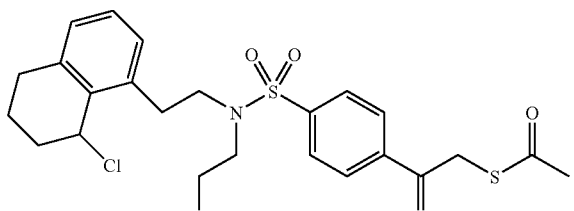
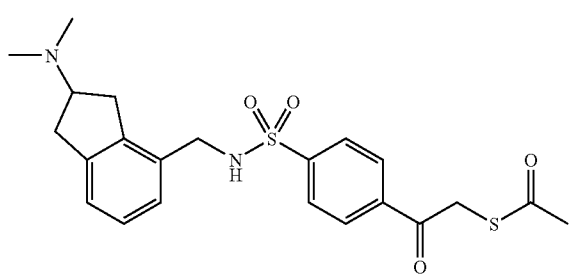
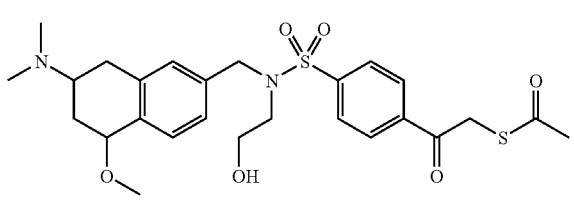
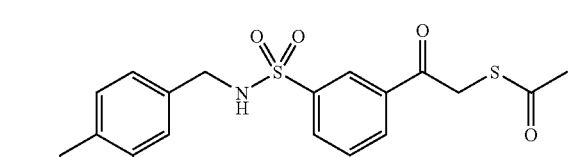

-continued

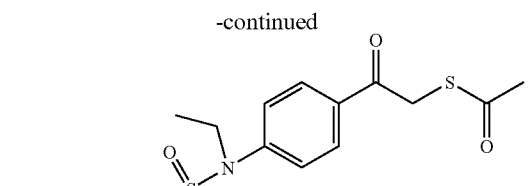
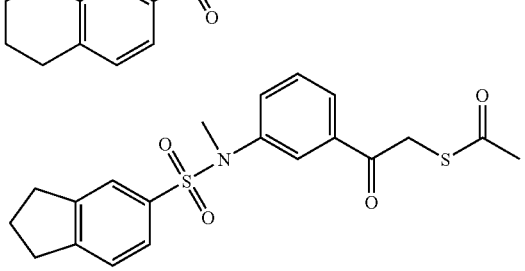

In certain embodiments of compounds of the invention, Q is a bond and G1 is an optionally substituted fused aryl and heterocycloalkyl, an optionally substituted fused heteroaryl and cycloalkyl, or an optionally substituted fused heteroaryl and heterocycloalkyl.

In certain embodiments of compounds of the invention, Q is a bond and G1 is an optionally substituted fused aryl and heterocycloalkyl, an optionally substituted fused heteroaryl and cycloalkyl, or an optionally substituted fused heteroaryl and heterocycloalkyl and G1 is selected from a group consisting of:

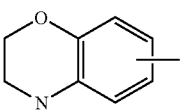 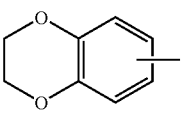
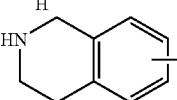 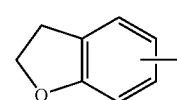
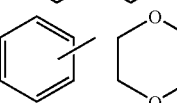 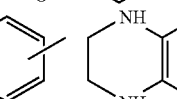
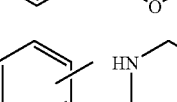 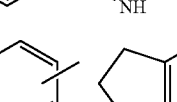
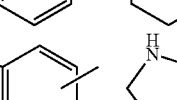 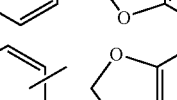
 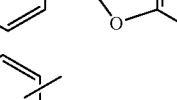
 

In certain embodiments of compounds of the invention, Q is a bond and G1 is an optionally substituted fused aryl and heterocycloalkyl, an optionally substituted fused heteroaryl and cycloalkyl, or an optionally substituted fused heteroaryl and heterocycloalkyl and where G1 is optionally singly or multiply substituted with substituents independently chosen from the group {K}.

In certain embodiments of compounds of the invention, Q is a bond and G1 is an optionally substituted fused aryl and heterocycloalkyl, an optionally substituted fused heteroaryl and cycloalkyl, or an optionally substituted fused heteroaryl and heterocycloalkyl, where G1 is optionally singly or multiply substituted with substituents independently chosen from the group {K}, and Q is a bond, T is S.

In certain embodiments of compounds of the invention, Q is a bond and G1 is an optionally substituted fused aryl and heterocycloalkyl, an optionally substituted fused heteroaryl and cycloalkyl, or an optionally substituted fused heteroaryl and heterocycloalkyl, where G1 is optionally singly or multiply substituted with substituents independently chosen from the group {K}, Q is a bond, T is S and $R_2$ or $R_3$ is selected from the group consisting of N-sulfonamido and S-sulfonamido.

In certain embodiments of compounds of the invention, Q is a bond and G1 is an optionally substituted fused aryl and heterocycloalkyl, an optionally substituted fused heteroaryl and cycloalkyl, or an optionally substituted fused heteroaryl and heterocycloalkyl, where G1 is optionally singly or multiply substituted with substituents independently chosen from the group {K}, Q is a bond, T is S, $R_2$ or $R_3$ is selected from the group consisting of N-sulfonamido and S-sulfonamido and $R_1$, $R_4$, and $R_5$ are hydrogen and wherein one of $R_2$ and $R_3$ are hydrogen.

In certain embodiments of compounds of the invention, Q is a bond and G1 is an optionally substituted fused aryl and heterocycloalkyl, an optionally substituted fused heteroaryl and cycloalkyl, or an optionally substituted fused heteroaryl and heterocycloalkyl, where G1 is optionally singly or multiply substituted with substituents independently chosen from the group {K}, Q is a bond, T is S, $R_2$ or $R_3$ is selected from the group consisting of N-sulfonamido and S-sulfonamido, $R_1$, $R_4$, and $R_5$ are hydrogen and wherein one of $R_2$ and $R_3$ are hydrogen. and G2 is a bond, methylene, or ethylene.

In certain embodiments of compounds of the invention, Q is a bond and G1 is an optionally substituted fused aryl and heterocycloalkyl, an optionally substituted fused heteroaryl and cycloalkyl, or an optionally substituted fused heteroaryl and heterocycloalkyl, where G1 is optionally singly or multiply substituted with substituents independently chosen from the group {K}, Q is a bond, T is S, $R_2$ or $R_3$ is selected from the group consisting of N-sulfonamido and S-sulfonamido, $R_1$, $R_4$, and $R_5$ are hydrogen and wherein one of $R_2$ and $R_3$ are hydrogen and G2 is a bond, methylene, or ethylene and the compound has the structure selected from a group consisting of:

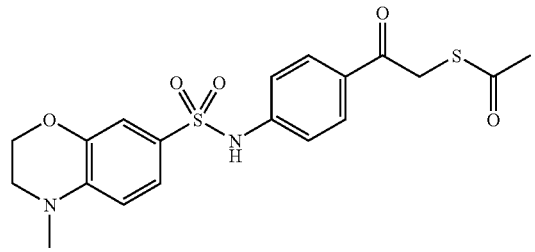

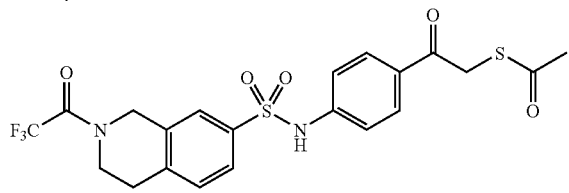

-continued

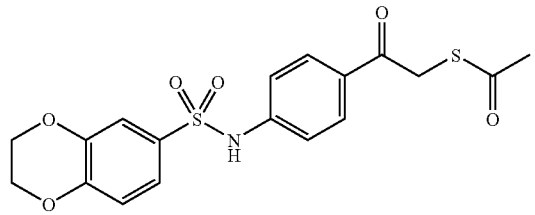

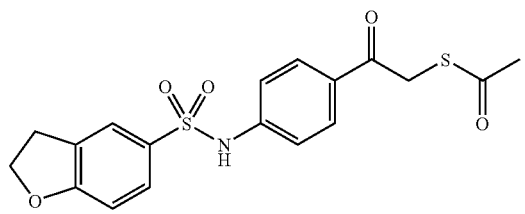

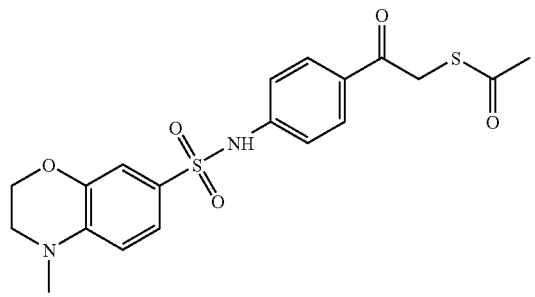

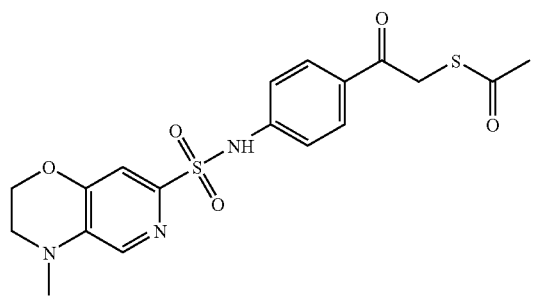

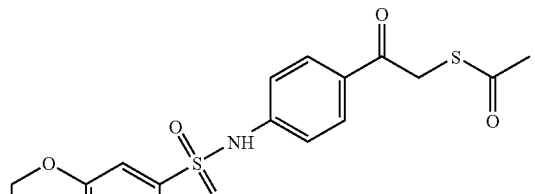

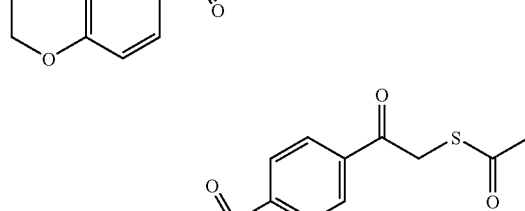

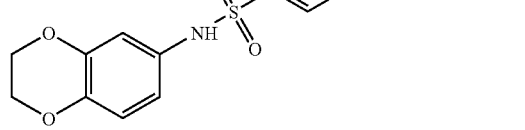

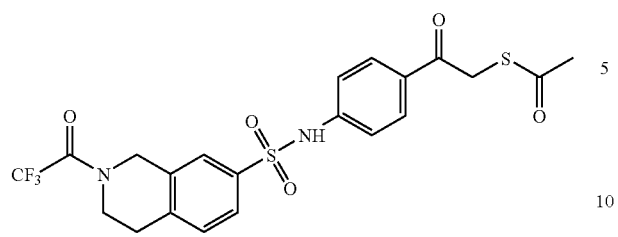
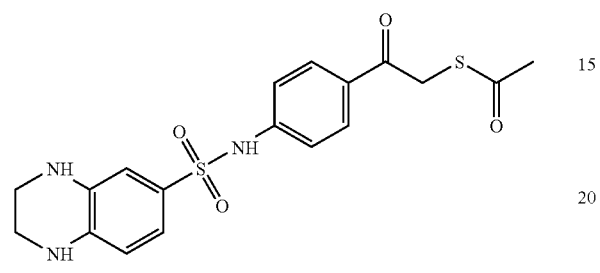
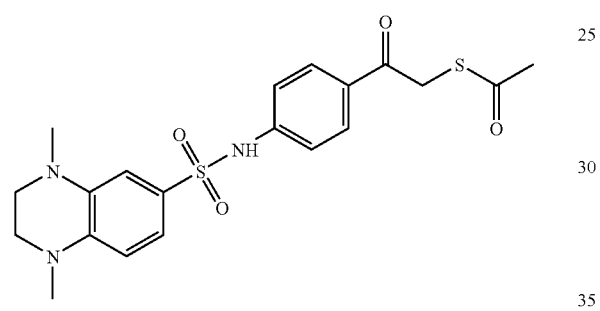
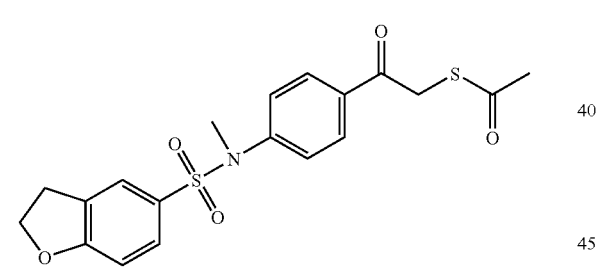
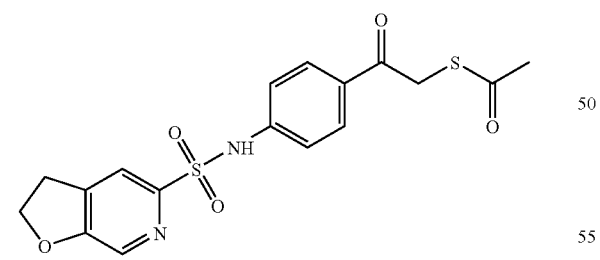
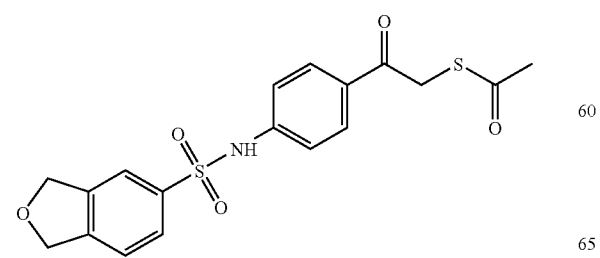
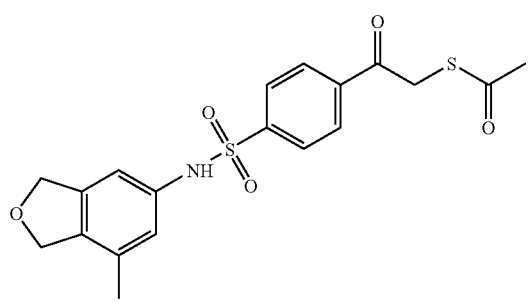
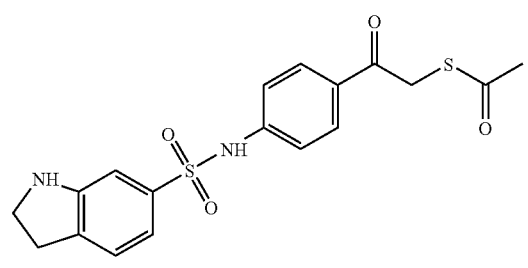
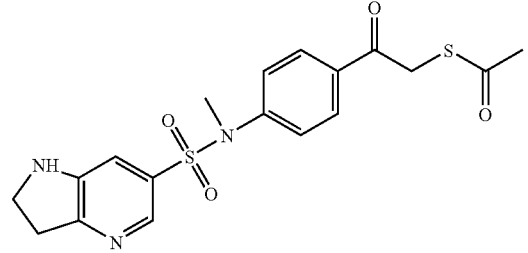
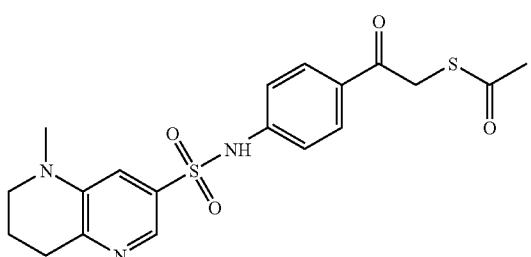
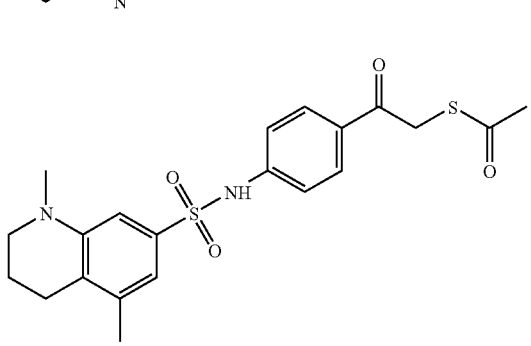
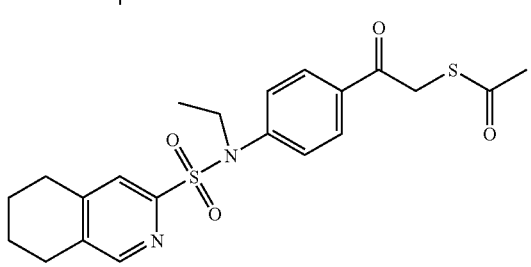

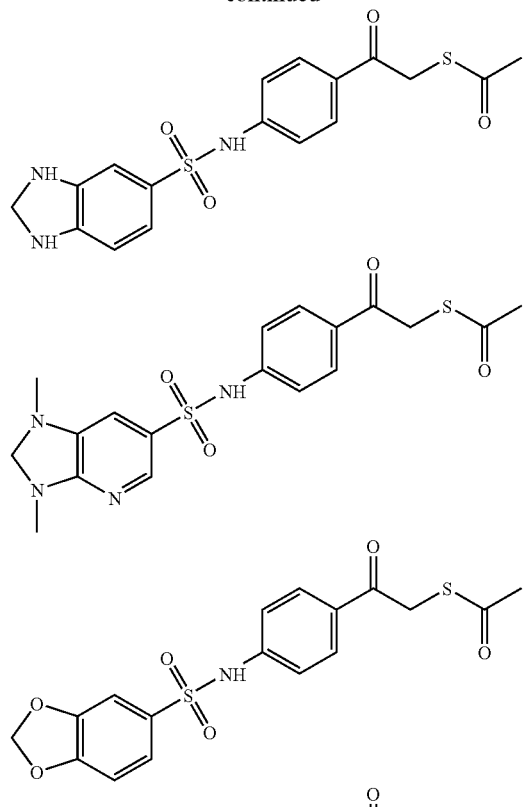

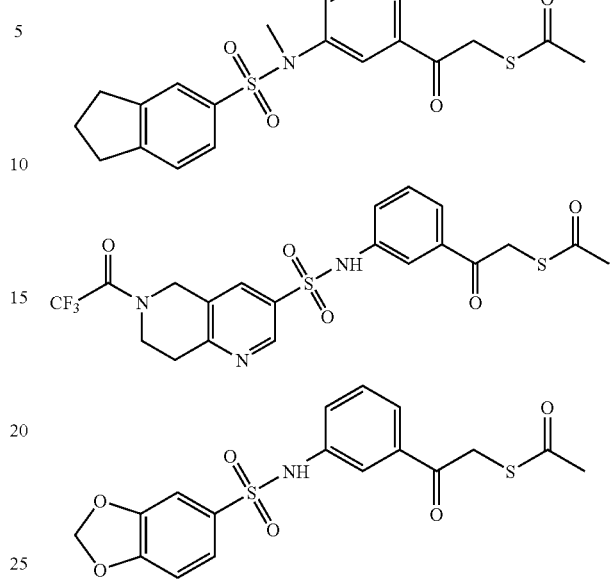

In certain embodiments of compounds of the invention, Q is a bond and G1 is an optionally substituted fused aryl and heterocycloalkyl, an optionally substituted fused heteroaryl and cycloalkyl, or an optionally substituted fused heteroaryl and heterocycloalkyl, where G1 is optionally singly or multiply substituted with substituents independently chosen from the group {K}, Q is a bond, T is S, $R_2$ or $R_3$ is selected from the group consisting of N-sulfonamido and S-sulfonamido, $R_1$, $R_4$, and $R_5$ are hydrogen and wherein one of $R_2$ and $R_3$ are hydrogen, G2 is a bond, methylene, or ethylene and $R_2$ is selected from the group consisting of N-sulfonamido.

In certain embodiments of compounds of the invention, Q is a bond and G1 is an optionally substituted fused aryl and heterocycloalkyl, an optionally substituted fused heteroaryl and cycloalkyl, or an optionally substituted fused heteroaryl and heterocycloalkyl, where G1 is optionally singly or multiply substituted with substituents independently chosen from the group {K}, Q is a bond, T is S, $R_2$ or $R_3$ is selected from the group consisting of N-sulfonamido and S-sulfonamido, $R_1$, $R_4$, and $R_5$ are hydrogen and wherein one of $R_2$ and $R_3$ are hydrogen, G2 is a bond, methylene, or ethylene, $R_2$ is selected from the group consisting of N-sulfonamido and the compound has the structure selected from a group consisting of:

In certain embodiments of compounds of the invention, the compound is selected from the group consisting of:

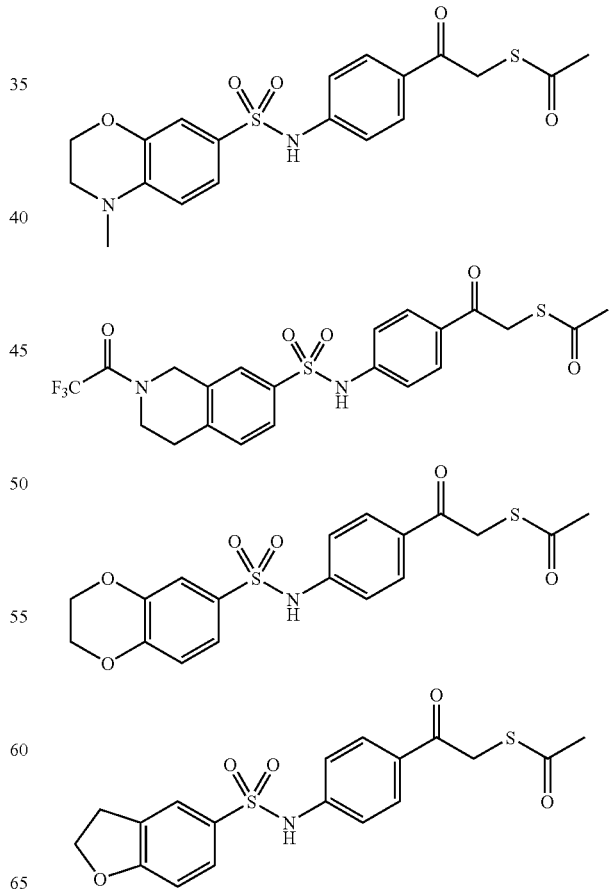

-continued
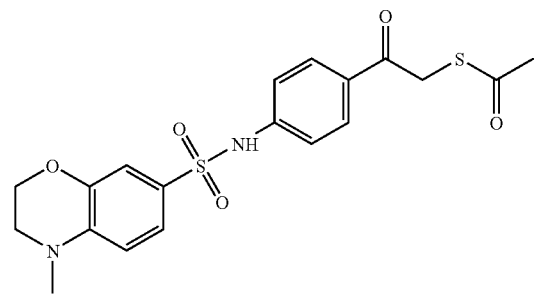
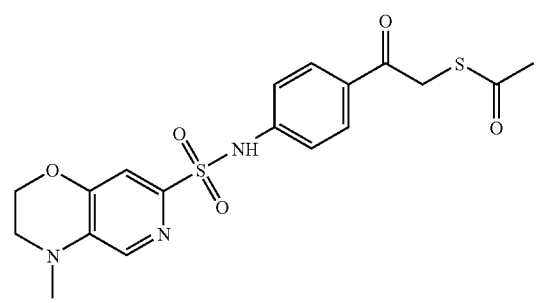
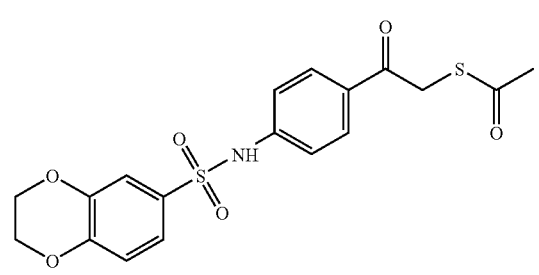
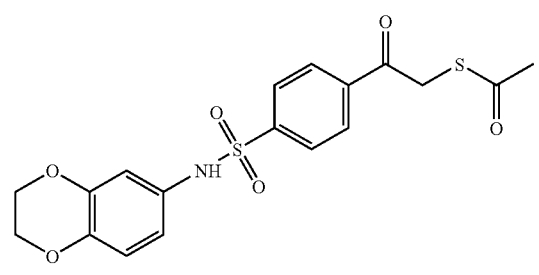
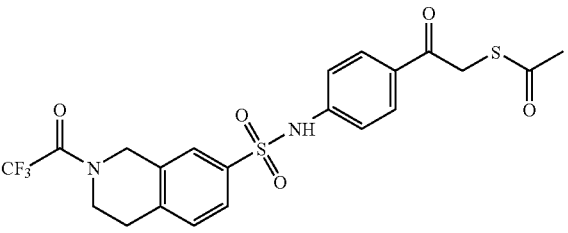
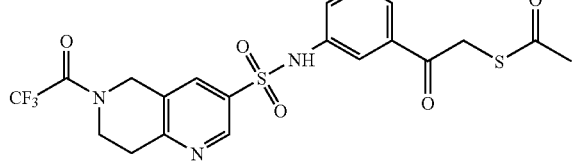
-continued
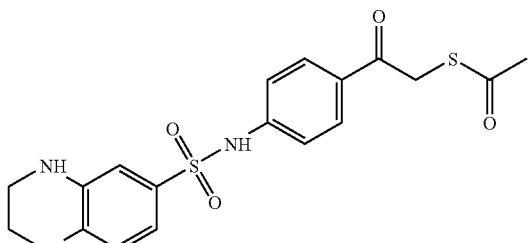
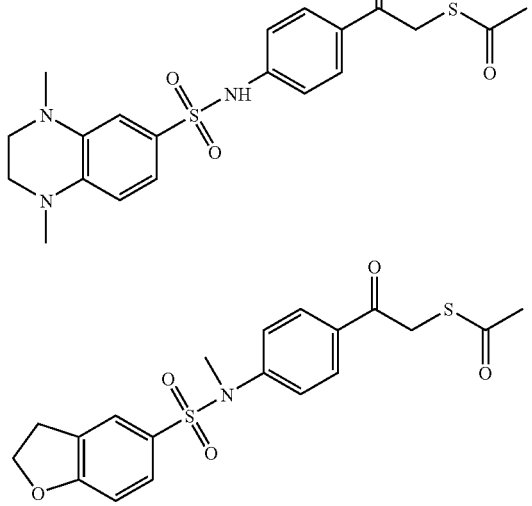
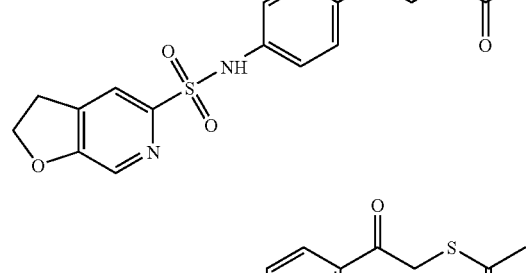
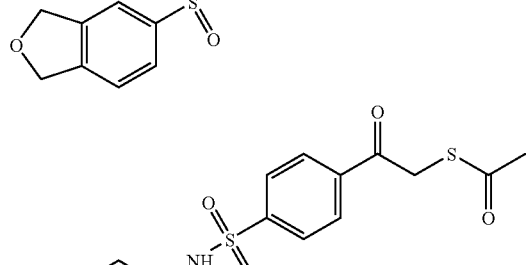

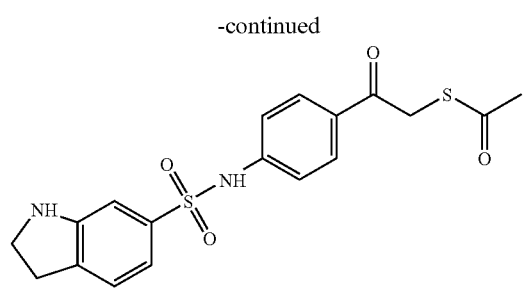

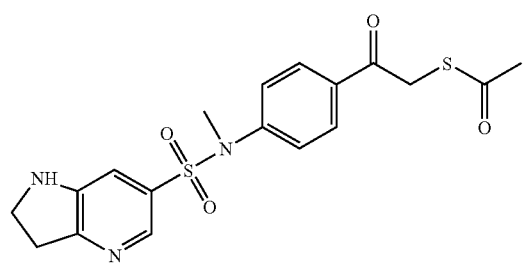

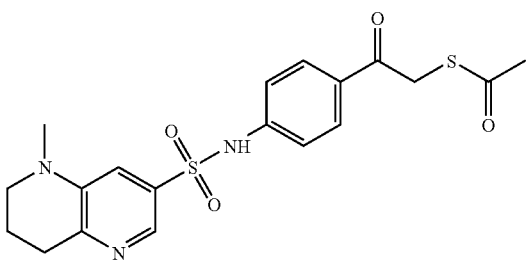

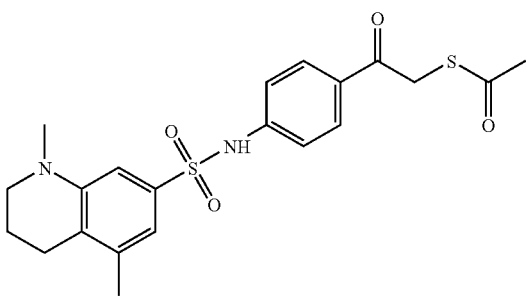

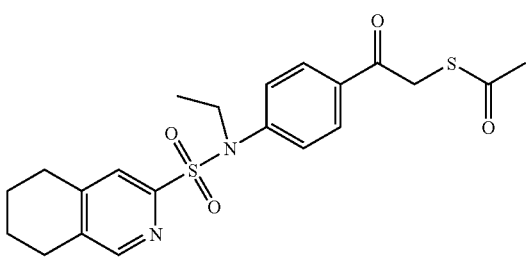

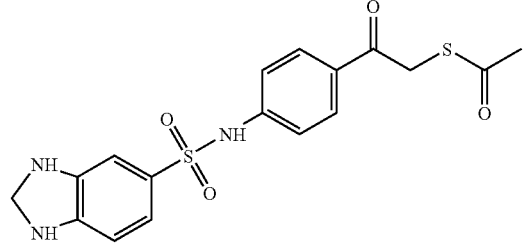

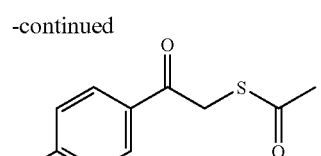

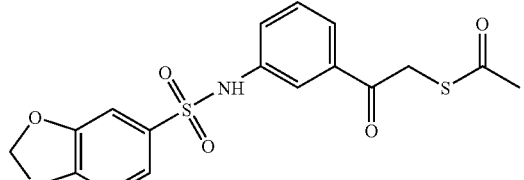

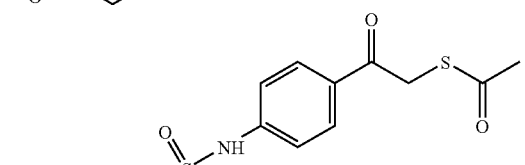

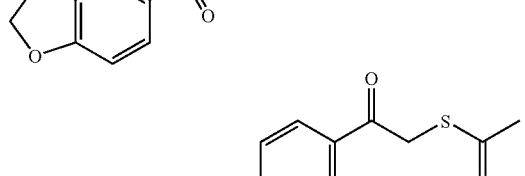

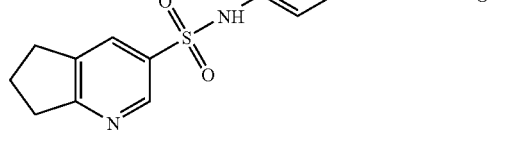

In certain embodiments of compounds of the invention, Q is a bond and G1 is an optionally substituted linked biaryl.

In certain embodiments of compounds of the invention, Q is a bond, G1 is an optionally substituted linked biaryl selected from a group consisting of:

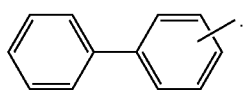

In certain embodiments of compounds of the invention, Q is a bond, G1 is an optionally substituted linked biaryl selected from a group consisting of:

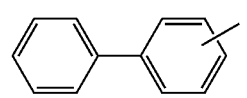

and G1 is optionally singly or multiply substituted with substituents independently chosen from the group {K}.

In certain embodiments of compounds of the invention, Q is a bond, G1 is an optionally substituted linked biaryl selected from a group consisting of:

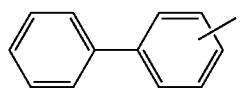

and G1 is optionally singly or multiply substituted with substituents independently chosen from the group {K}, and Q is a bond, T is S, R6 and R7 are both H.

In certain embodiments of compounds of the invention, Q is a bond, G1 is an optionally substituted linked biaryl selected from a group consisting of:

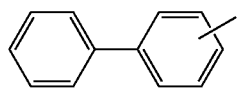

and G1 is optionally singly or multiply substituted with substituents independently chosen from the group {K}, Q is a bond, T is S, R6 and R7 are both H, and $R_2$ or $R_3$ is selected from the group consisting of N-sulfonamido and S-sulfonamido.

In certain embodiments of compounds of the invention, Q is a bond, G1 is an optionally substituted linked biaryl selected from a group consisting of:

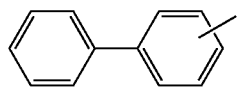

and G1 is optionally singly or multiply substituted with substituents independently chosen from the group {K}, Q is a bond, T is S, R6 and R7 are both H, $R_2$ or $R_3$ is selected from the group consisting of N-sulfonamido and S-sulfonamido and $R_1$, $R_4$, and $R_5$ are hydrogen, wherein one of $R_2$ and $R_3$ are hydrogen.

In certain embodiments of compounds of the invention, Q is a bond, G1 is an optionally substituted linked biaryl selected from a group consisting of:

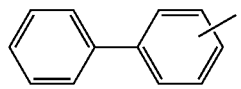

and G1 is optionally singly or multiply substituted with substituents independently chosen from the group {K}, Q is a bond, T is S, R6 and R7 are both H, $R_2$ or $R_3$ is selected from the group consisting of N-sulfonamido and S-sulfonamido, $R_1$, $R_4$, and $R_5$ are hydrogen, wherein one of $R_2$ and $R_3$ are hydrogen, and G2 is a bond, methylene, or ethylene.

In certain embodiments of compounds of the invention, Q is a bond, G1 is an optionally from a group consisting of:

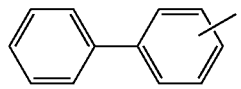

and G1 is optionally singly or multiply substituted with substituents independently chosen from the group {K}, Q is a bond, T is S, R6 and R7 are both H, $R_2$ or $R_3$ is selected from the group consisting of N-sulfonamido and S-sulfonamido, $R_1$, $R_4$, and $R_5$ are hydrogen, wherein one of $R_2$ and $R_3$ are hydrogen, G2 is a bond, methylene, or ethylene and the compound has the structure selected from a group consisting of:

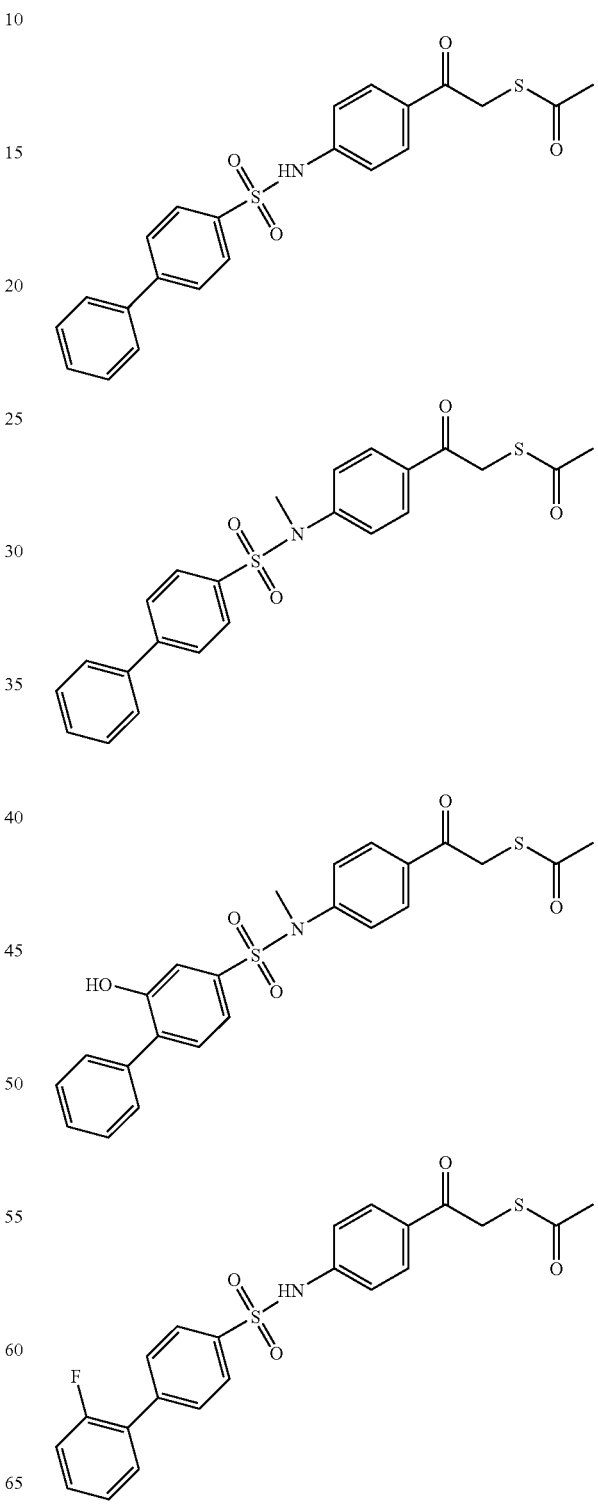

-continued
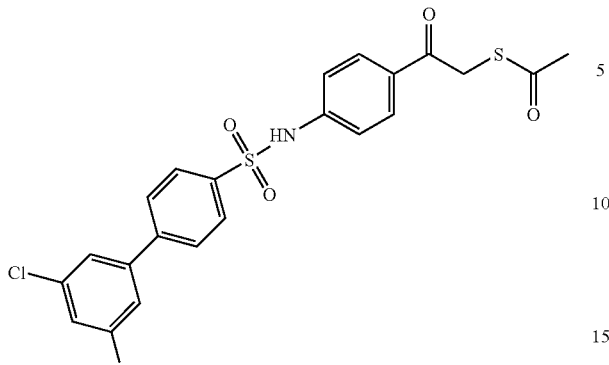
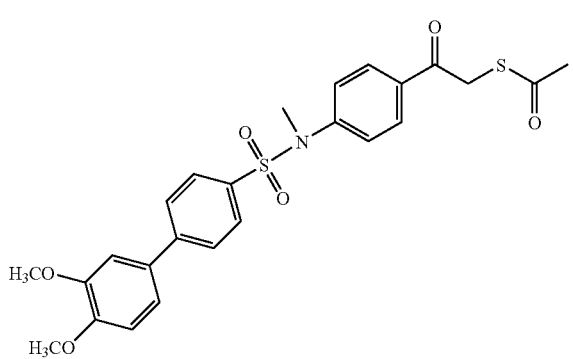
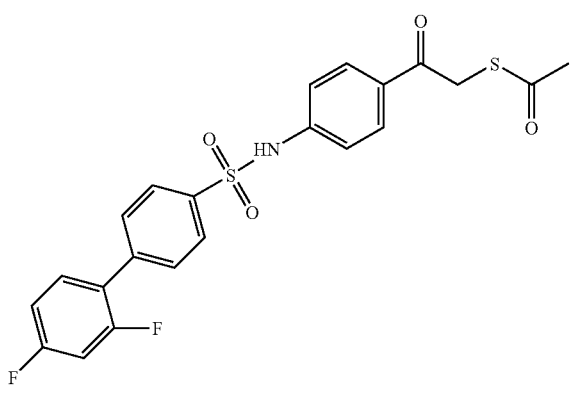
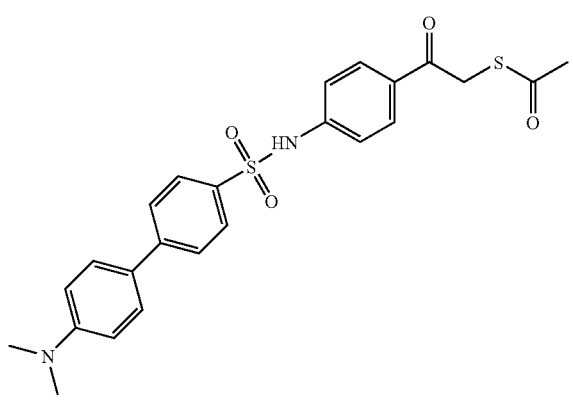
-continued
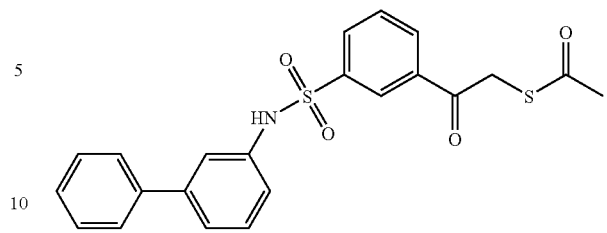
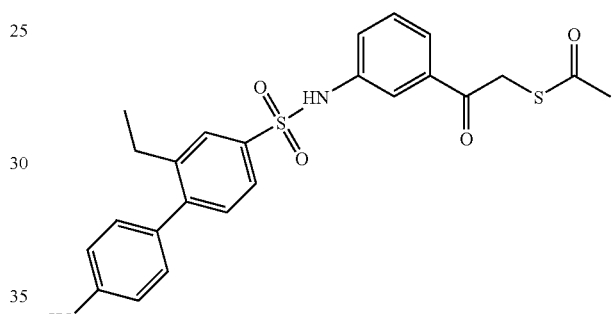
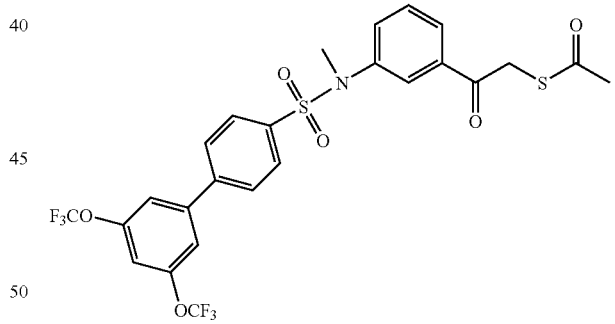
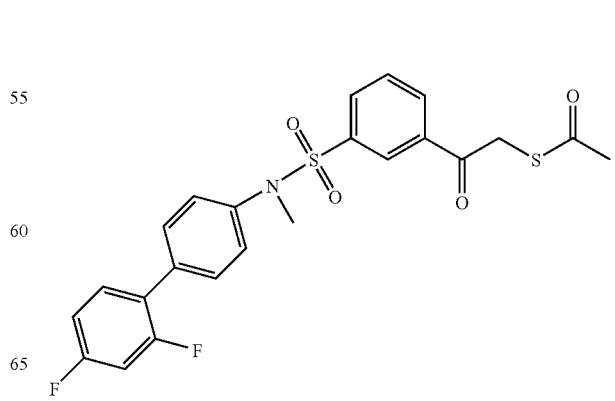

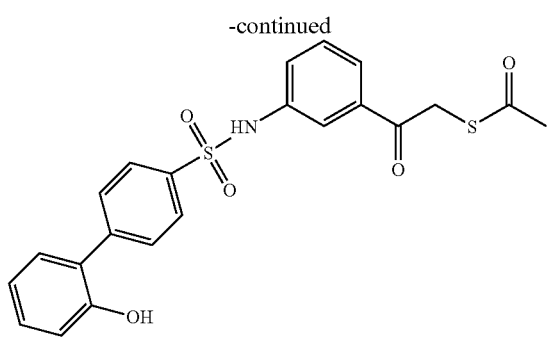

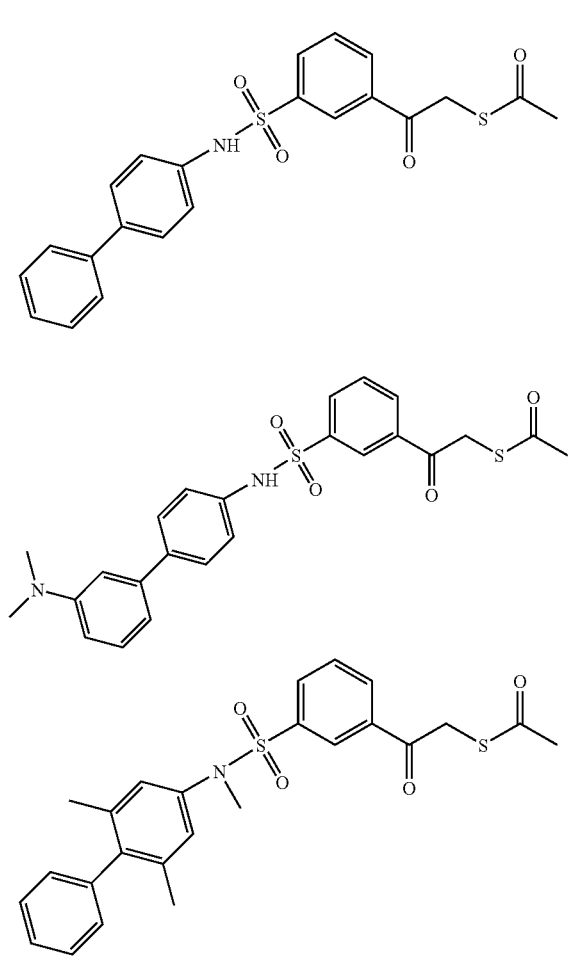

In certain embodiments of compounds of the invention, Q is a bond, G1 is an optionally substituted linked biaryl selected from a group consisting of:

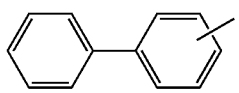

and G1 is optionally singly or multiply substituted with substituents independently chosen from the group {K}, Q is a bond, T is S, R6 and R7 are both H and the compound is selected from the group consisting of In certain embodiments of compounds of the invention, Q is a bond and G1 is an optionally substituted linked aryl and heteroaryl ring.

In certain embodiments of compounds of the invention, Q is a bond and G1 is an optionally substituted linked aryl and heteroaryl ring selected from a group consisting of:

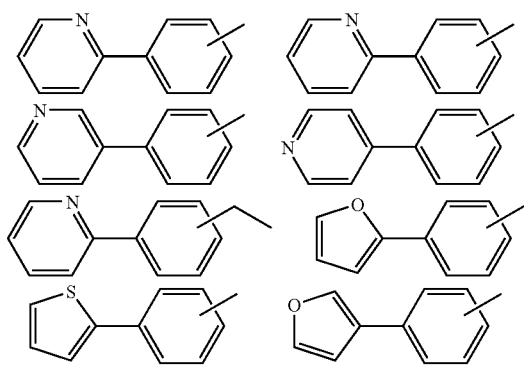

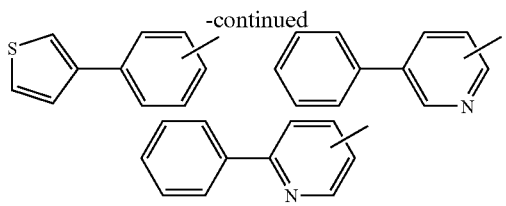

In certain embodiments of compounds of the invention, Q is a bond and G1 is an optionally substituted linked aryl and heteroaryl ring selected from a group consisting of:

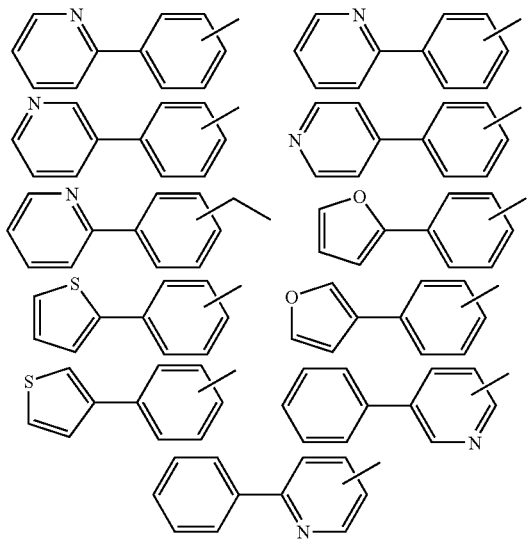

and G1 is optionally singly or multiply substituted with substituents independently chosen from the group {K}.

In certain embodiments of compounds of the invention, Q is a bond and G1 is an optionally substituted linked aryl and heteroaryl ring selected from a group consisting of:

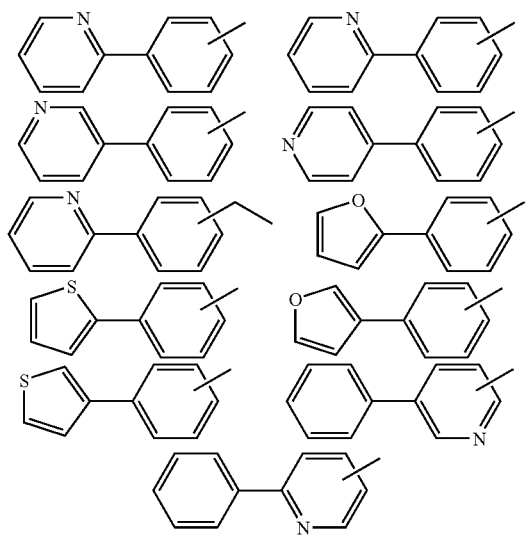

and G1 is optionally singly or multiply substituted with substituents independently chosen from the group {K}, Q is a bond, T is S, R6 and R7 are both H.

In certain embodiments of compounds of the invention, Q is a bond and G1 is an optionally substituted linked aryl and heteroaryl ring selected from a group consisting of:

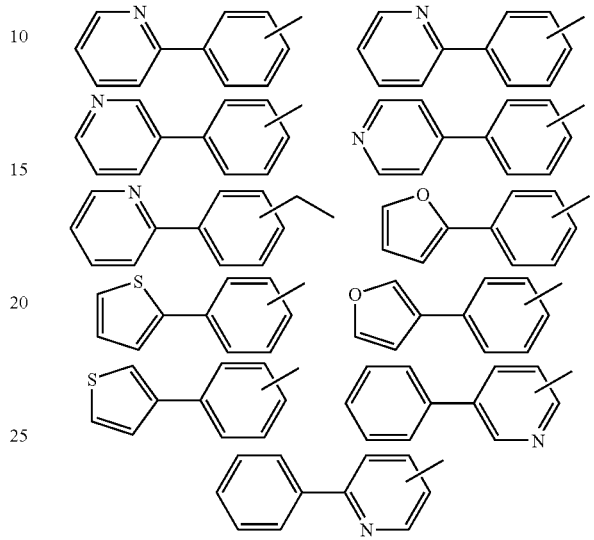

and G1 is optionally singly or multiply substituted with substituents independently chosen from the group {K}, Q is a bond, T is S, R6 and R7 are both H, and $R_3$ is selected from the group consisting of N-sulfonamido and S-sulfonamido.

In certain embodiments of compounds of the invention, Q is a bond and G1 is an optionally substituted linked aryl and heteroaryl ring selected from a group consisting of:

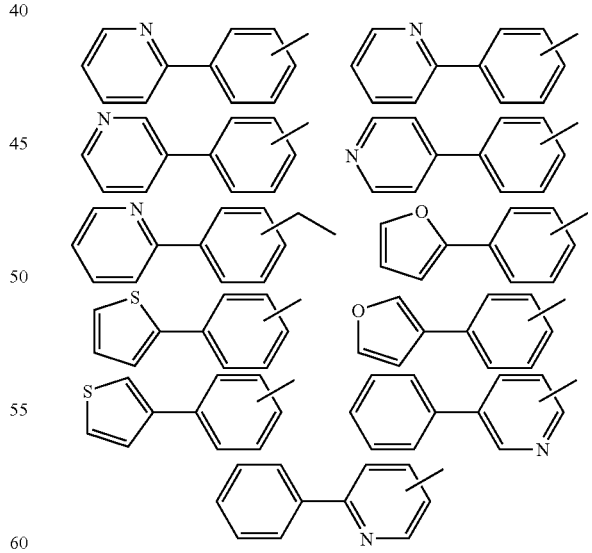

and G1 is optionally singly or multiply substituted with substituents independently chosen from the group {K}, Q is a bond, T is S, R6 and R7 are both H, $R_3$ is selected from the group consisting of N-sulfonamido and S-sulfonamido and $R_1, R_2, R_4,$ and $R_5$ are hydrogen.

In certain embodiments of compounds of the invention, Q is a bond and G1 is an optionally substituted linked aryl and heteroaryl ring selected from a group consisting of:

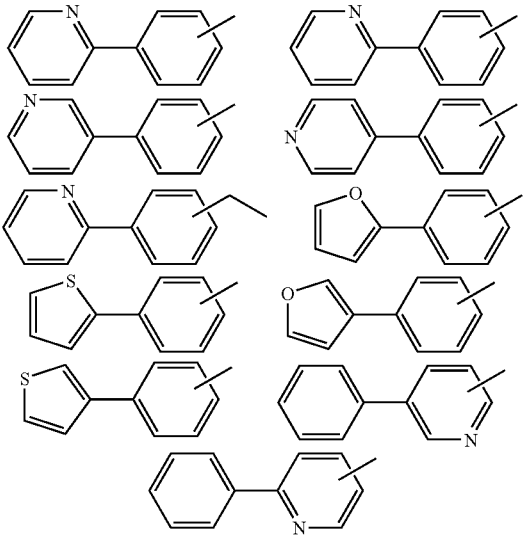

and G1 is optionally singly or multiply substituted with substituents independently chosen from the group {K}, Q is a bond, T is S, R6 and R7 are both H, $R_3$ is selected from the group consisting of N-sulfonamido and S-sulfonamido, $R_1$, $R_2$, $R_4$, and $R_5$ are hydrogen and G2 is a bond, methylene, or ethylene.

In certain embodiments of compounds of the invention, Q is a bond and G1 is an optionally substituted linked aryl and heteroaryl ring selected from a group consisting of:

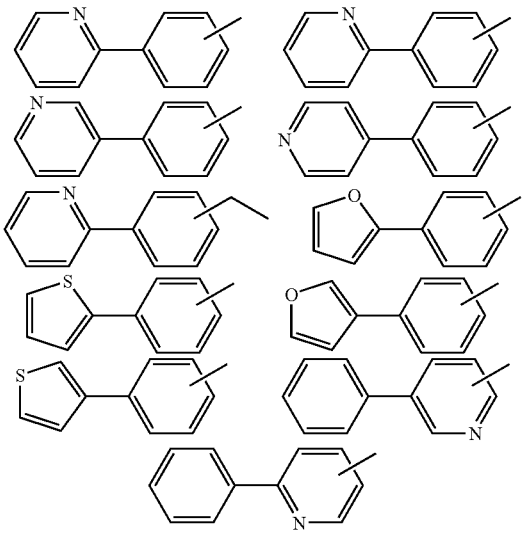

and G1 is optionally singly or multiply substituted with substituents independently chosen from the group {K}, Q is a bond, T is S, R6 and R7 are both H, $R_3$ is selected from the group consisting of N-sulfonamido and S-sulfonamido, $R_1$, $R_2$, $R_4$, and $R_5$ are hydrogen, G2 is a bond, methylene, or ethylene and the compound has the structure selected from a group consisting of:

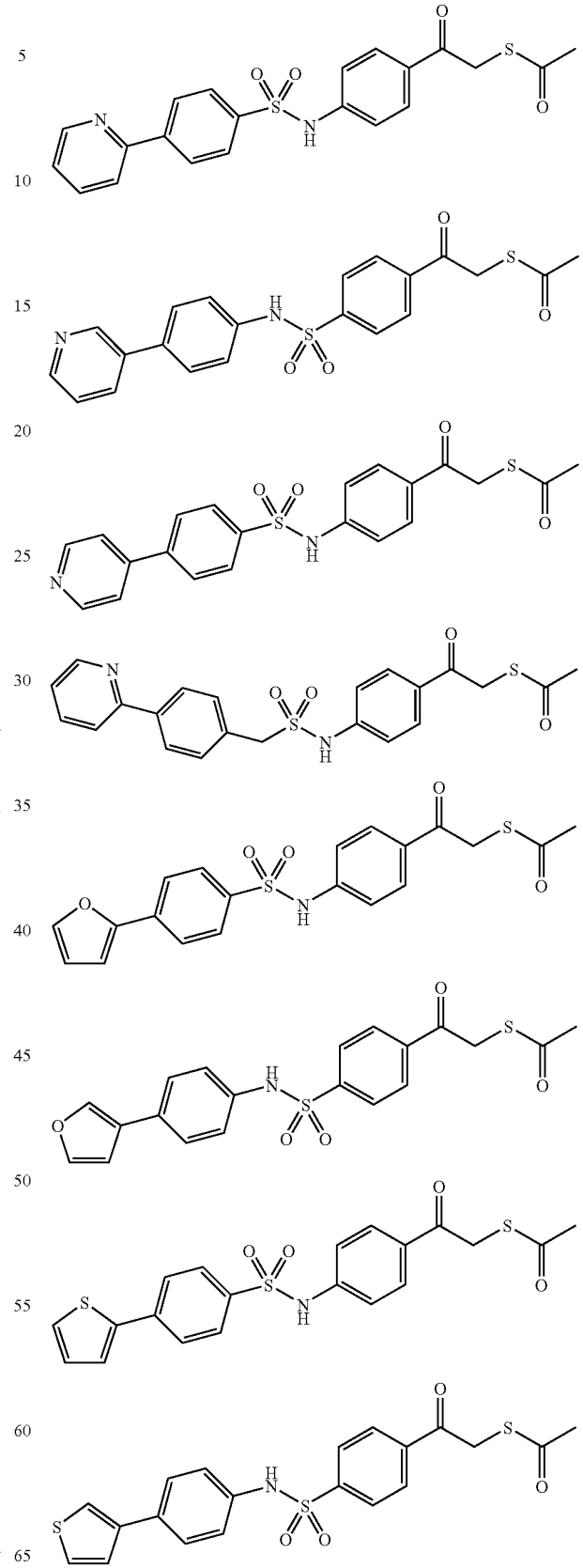

-continued

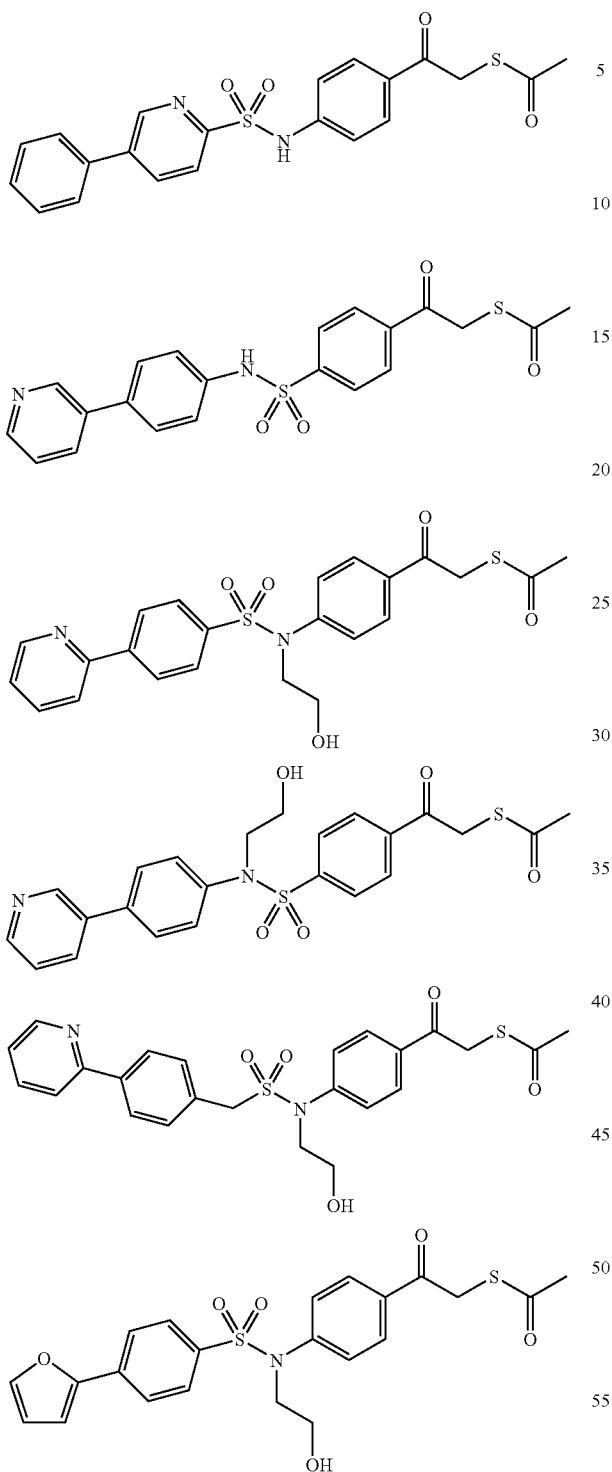

In certain embodiments of compounds of the invention, Q is a bond and G1 is an optionally substituted linked heteroaryl and heteroaryl ring.

In certain embodiments of compounds of the invention, Q is a bond and G1 is an optionally substituted linked heteroaryl and heteroaryl ring and G1 is selected from a group consisting of:

In certain embodiments of compounds of the invention, Q is a bond and G1 is an optionally substituted linked heteroaryl and heteroaryl ring and G1 is selected from a group consisting of:

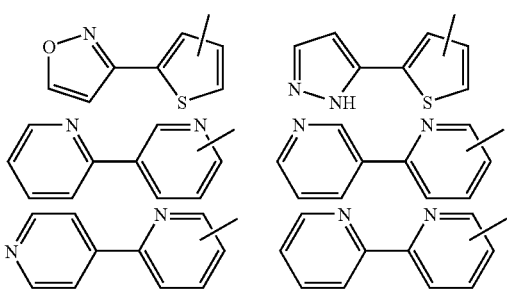

-continued

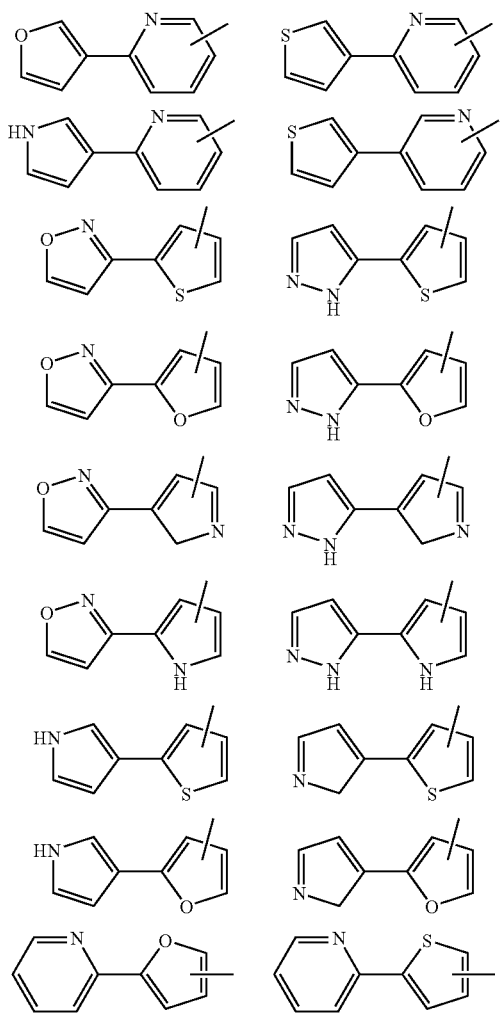

and G1 is optionally singly or multiply substituted with substituents independently chosen from the group {K}, Q is a bond and G1 is an optionally substituted linked heteroaryl and heteroaryl ring and G1 is selected from a group consisting of:

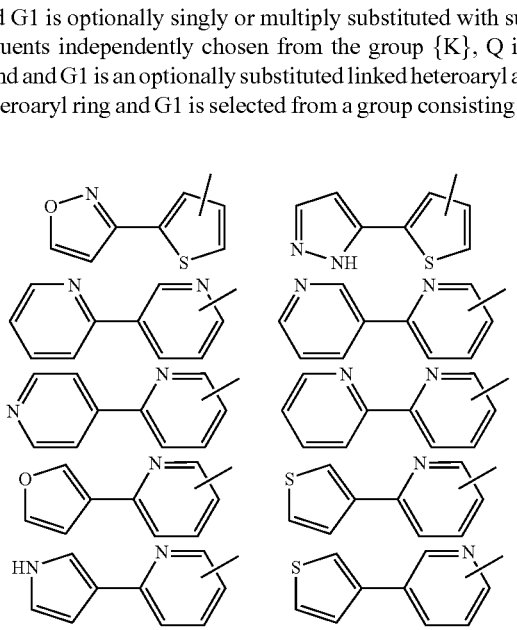

-continued

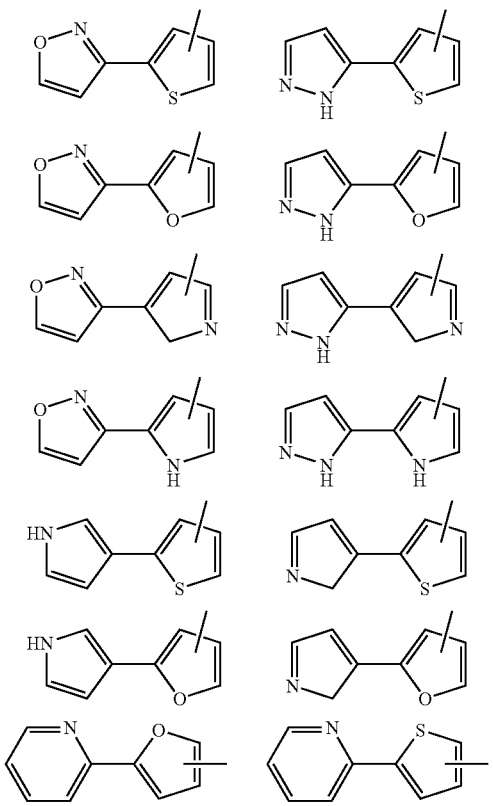

and G1 is optionally singly or multiply substituted with substituents independently chosen from the group {K}, and Q is a bond, T is S, R6 and R7 are both H.

In certain embodiments of compounds of the invention, Q is a bond and G1 is an optionally substituted linked heteroaryl and heteroaryl ring and G1 is selected from a group consisting of:

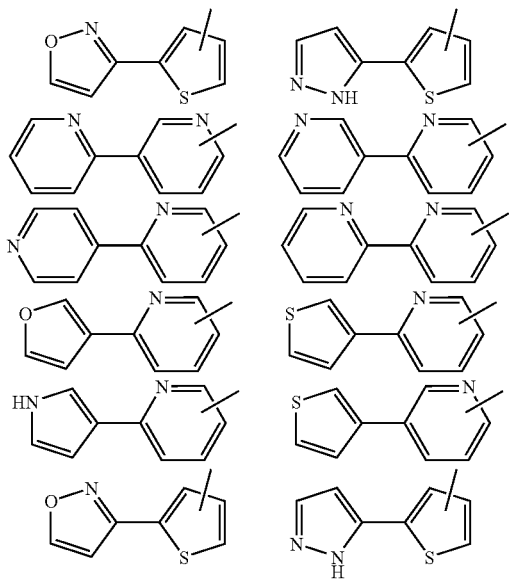

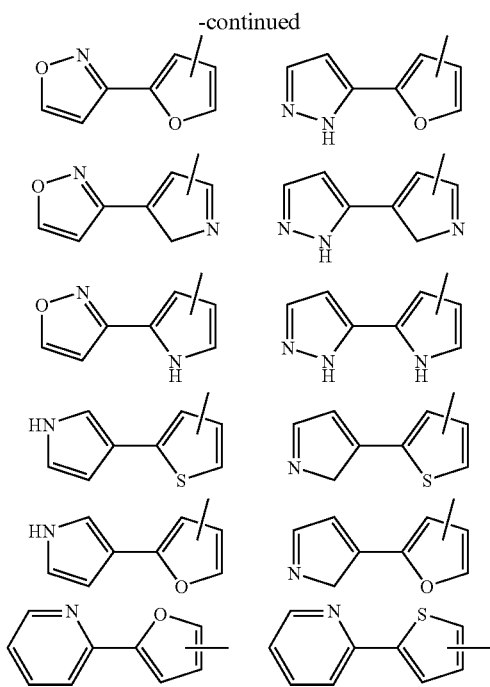

and G1 is optionally singly or multiply substituted with substituents independently chosen from the group {K}, Q is a bond, T is S, R6 and R7 are both H, and $R_3$ is selected from the group consisting of N-sulfonamido and S-sulfonamido.

In certain embodiments of compounds of the invention, Q is a bond and G1 is an optionally substituted linked heteroaryl and heteroaryl ring and G1 is selected from a group consisting of:

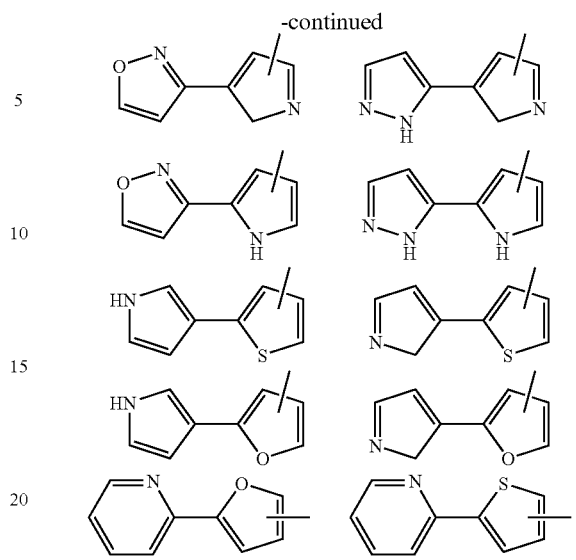

and G1 is optionally singly or multiply substituted with substituents independently chosen from the group {K}, Q is a bond, T is S, R6 and R7 are both H, $R_3$ is selected from the group consisting of N-sulfonamido and S-sulfonamido and $R_1$, $R_2$, $R_4$, and $R_5$ are hydrogen.

In certain embodiments of compounds of the invention, Q is a bond and G1 is an optionally substituted linked heteroaryl and heteroaryl ring and G1 is selected from a group consisting of:

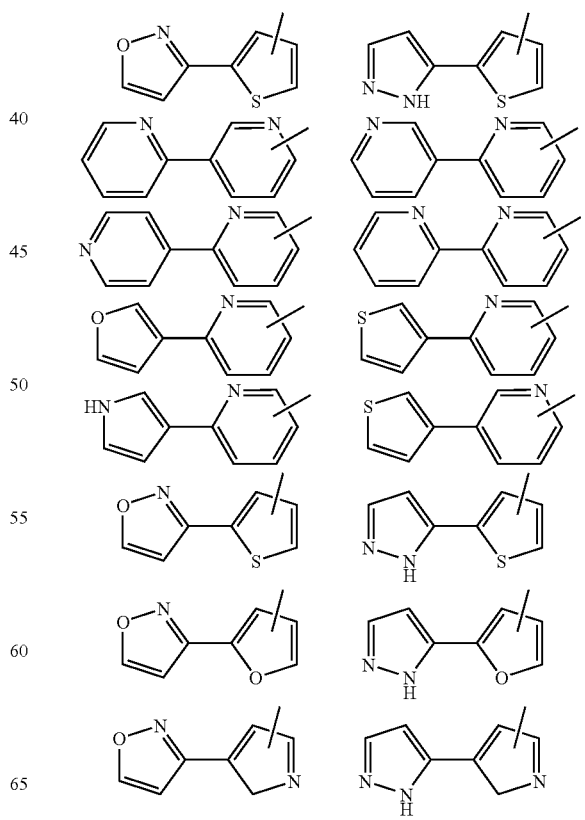

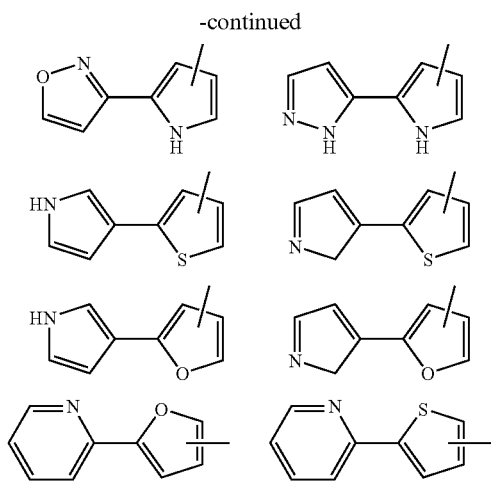

and G1 is optionally singly or multiply substituted with substituents independently chosen from the group {K}, Q is a bond, T is S, R6 and R7 are both H, $R_3$ is selected from the group consisting of N-sulfonamido and S-sulfonamido, $R_1$, $R_2$, $R_4$, and $R_5$ are hydrogen and G2 is a bond, methylene, or ethylene.

In certain embodiments of compounds of the invention, Q is a bond and G1 is an optionally substituted linked heteroaryl and heteroaryl ring and G1 is selected from a group consisting of:

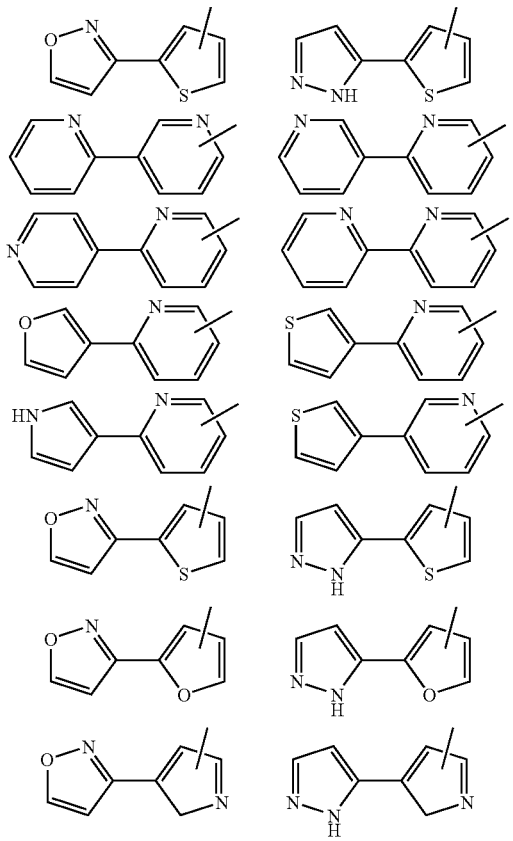

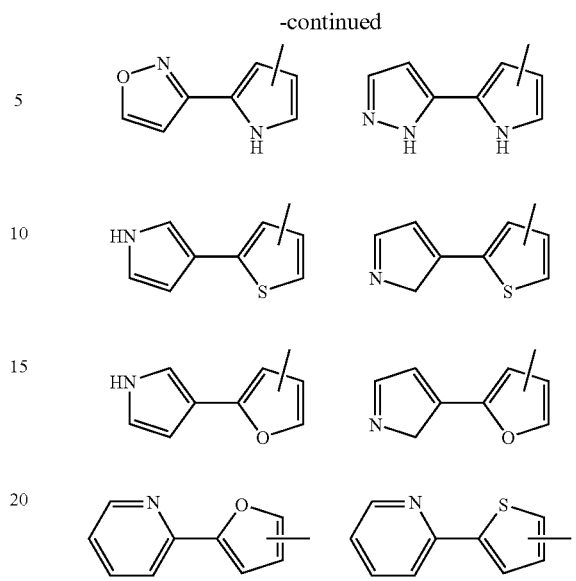

and G1 is optionally singly or multiply substituted with substituents independently chosen from the group {K}, Q is a bond, T is S, R6 and R7 are both H, $R_3$ is selected from the group consisting of N-sulfonamido and S-sulfonamido, $R_1$, $R_2$, $R_4$, and $R_5$ are hydrogen, G2 is a bond, methylene, or ethylene and the compound has the structure selected from a group consisting of:

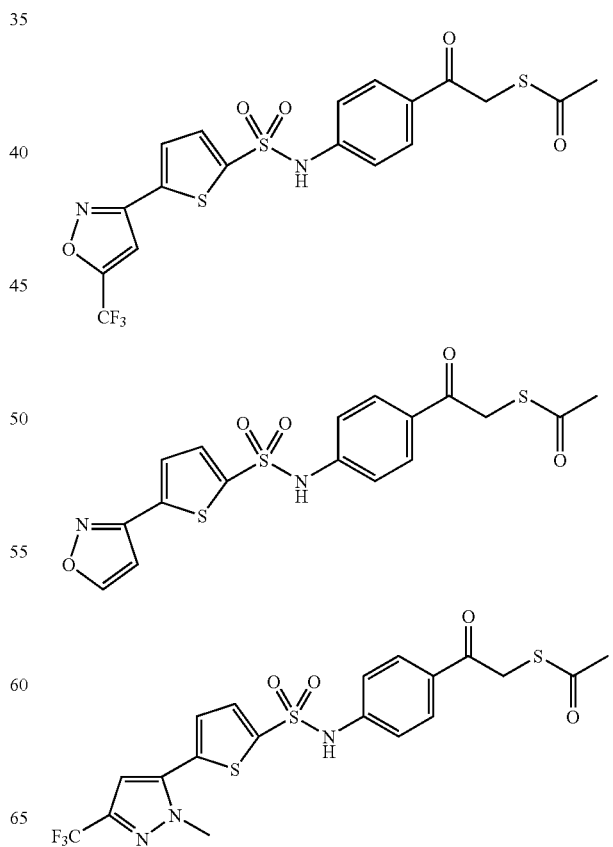

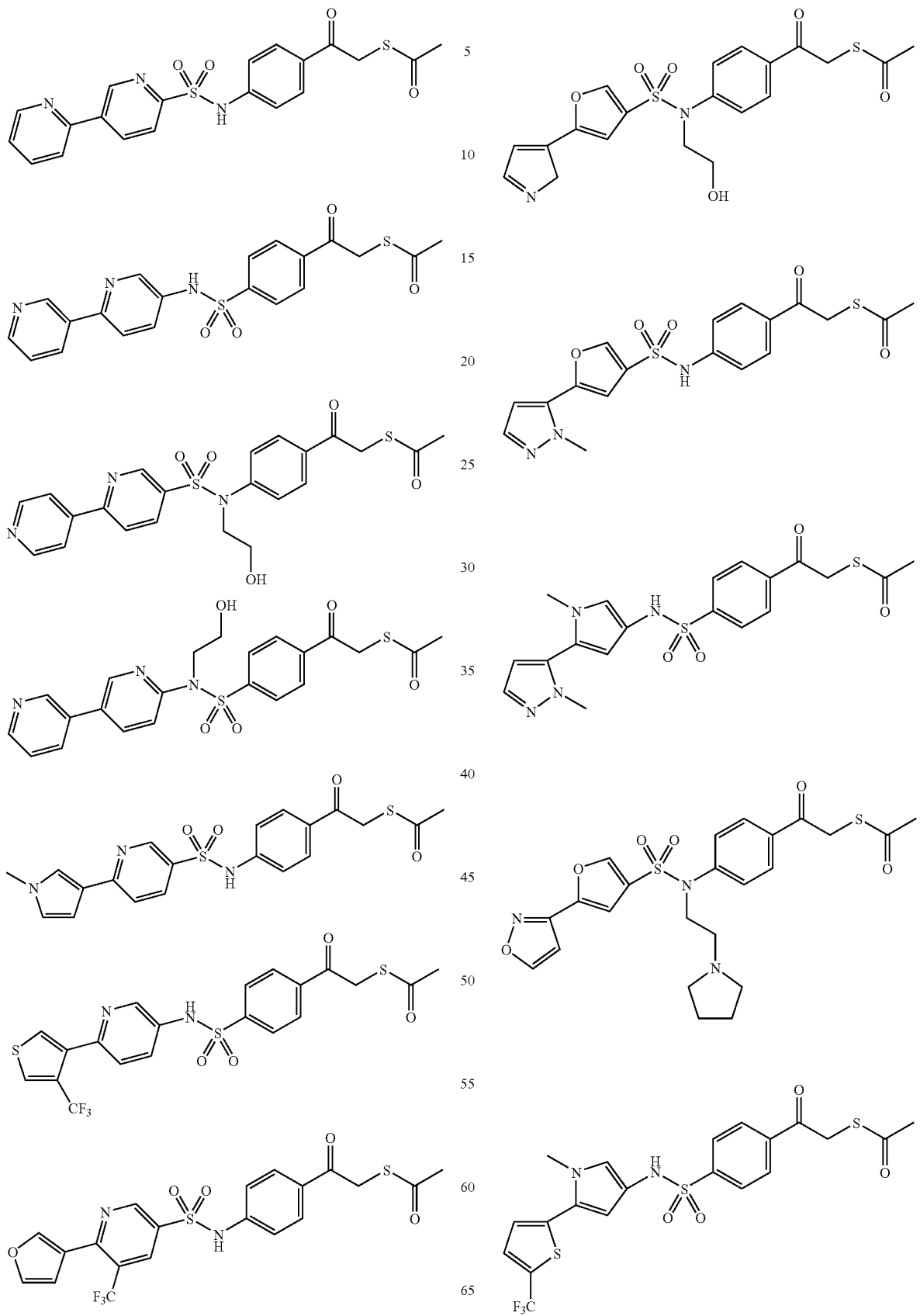

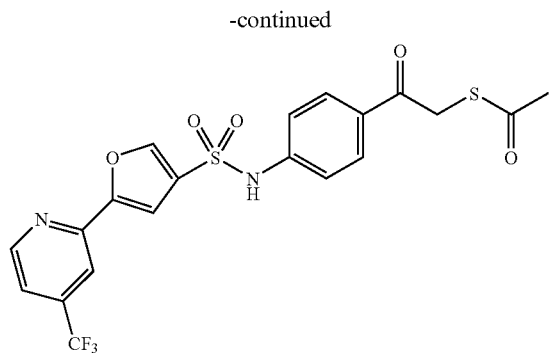

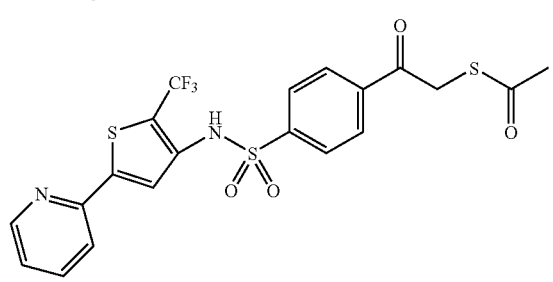

In certain embodiments of compounds of the invention, compounds having a structure of formula II:

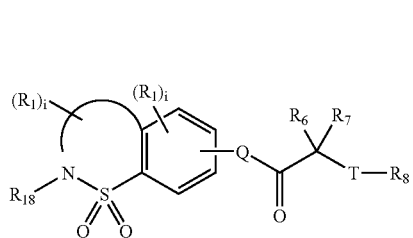

(II)

In certain embodiments of compounds of the invention, compounds having a structure of formula II selected from a group consisting of:

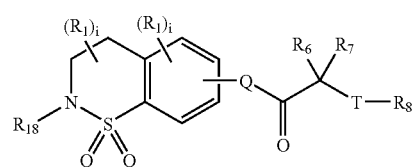

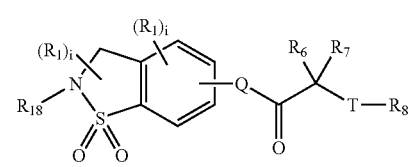

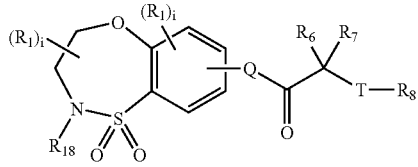

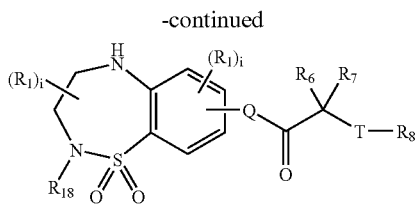

In certain embodiments of compounds of the invention, compounds having a structure of formula II selected from a group consisting of:

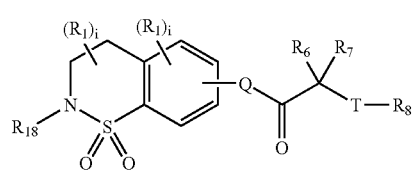

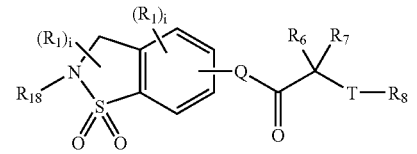

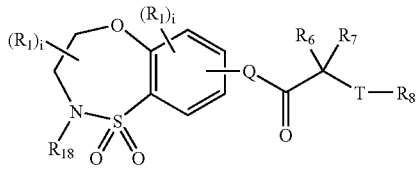

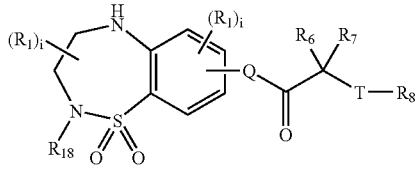

where $(R_1)_1$ is an endocyclic carbonyl

In certain embodiments of compounds of the invention, compounds selected from a group consisting of:

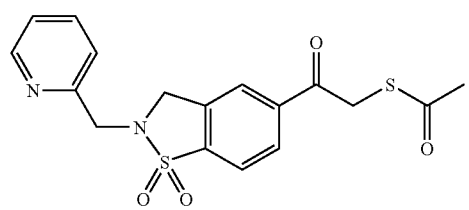

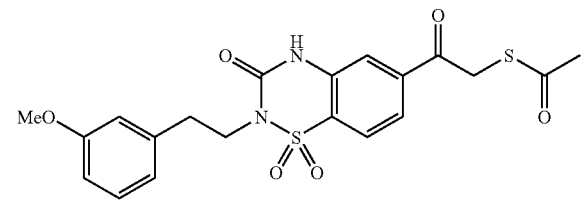

In certain embodiments of compounds of the invention, compounds having a structure of formula

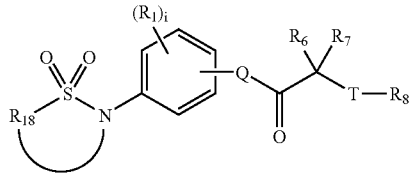
(III)

In certain embodiments of compounds of the invention, compounds having a structure of formula

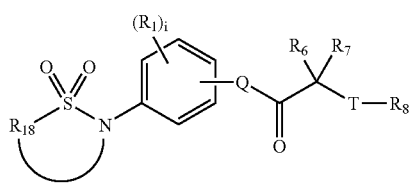
(III)

where the compound has a structure selected from a group consisting of:

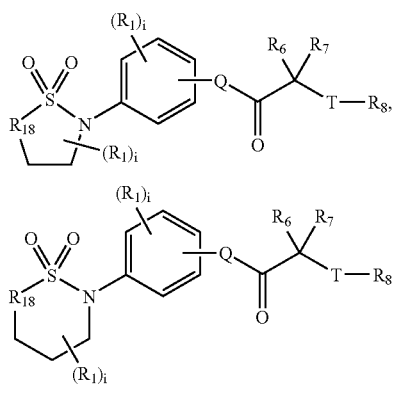

In certain embodiments of compounds of the invention, compounds having a structure of formula

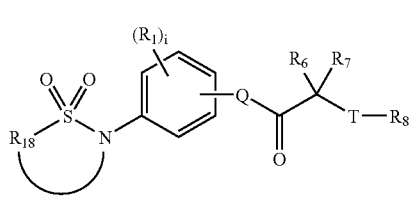
(III)

where the compound has a structure selected from a group consisting of:

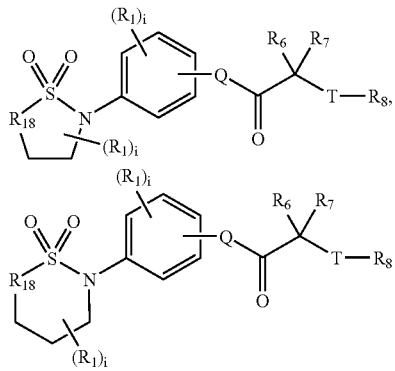

where $(R_1)_1$ is an endocyclic carbonyl.

In certain embodiments of compounds of the invention, compounds having a structure of formula

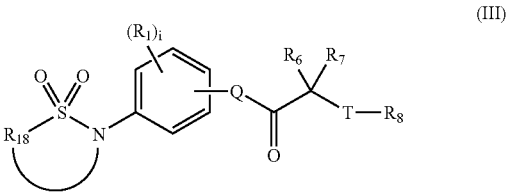
(III)

where the compound has a structure selected from a group consisting of:

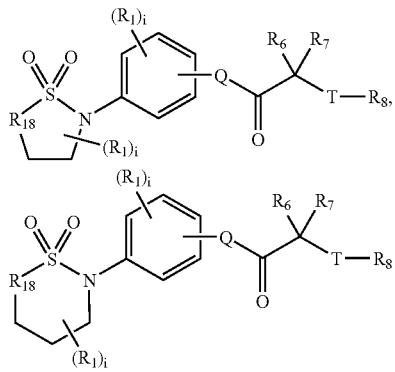

where the compound has the structure selected from a group consisting of:

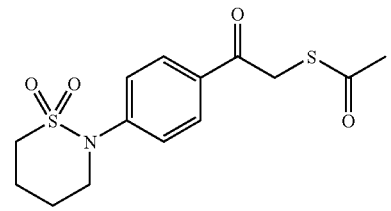

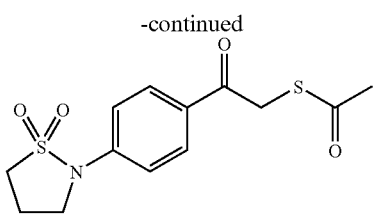

In another aspect, the invention relates to a compound selected from the group consisting of the compounds set forth in the examples or a pharmaceutically acceptable salt, ester, amide, or prodrug thereof:

Exemplary compounds and pharmaceutically acceptable esters or prodrugs thereof according to the invention include, but are not limited to, disulfide dimers, mercaptans, and thioesters of compounds of Formula I.

In one embodiment, the invention excludes of Formula I, capable of inhibiting the catalytic activity of histone deacetylase (HDAC).

In accordance with another aspect, the present invention provides compounds of Formula I, capable of inhibiting the cellular function of HDAC. In another aspect, the present invention provides pharmaceutical compositions comprising compounds of Formula I, capable of inhibiting the cellular function of histone deacetylase (HDAC).

In accordance with yet another aspect, the present invention provides a method of modulating the catalytic activity of HDAC comprising contacting said HDAC with a compound of the invention.

In accordance with yet another aspect, the present invention provides a method of inhibiting the catalytic activity of HDAC comprising contacting said HDAC with a pharmaceutical composition using the disclosed compounds.

In accordance with yet another aspect, the present invention provides a method of modulating the cellular function of

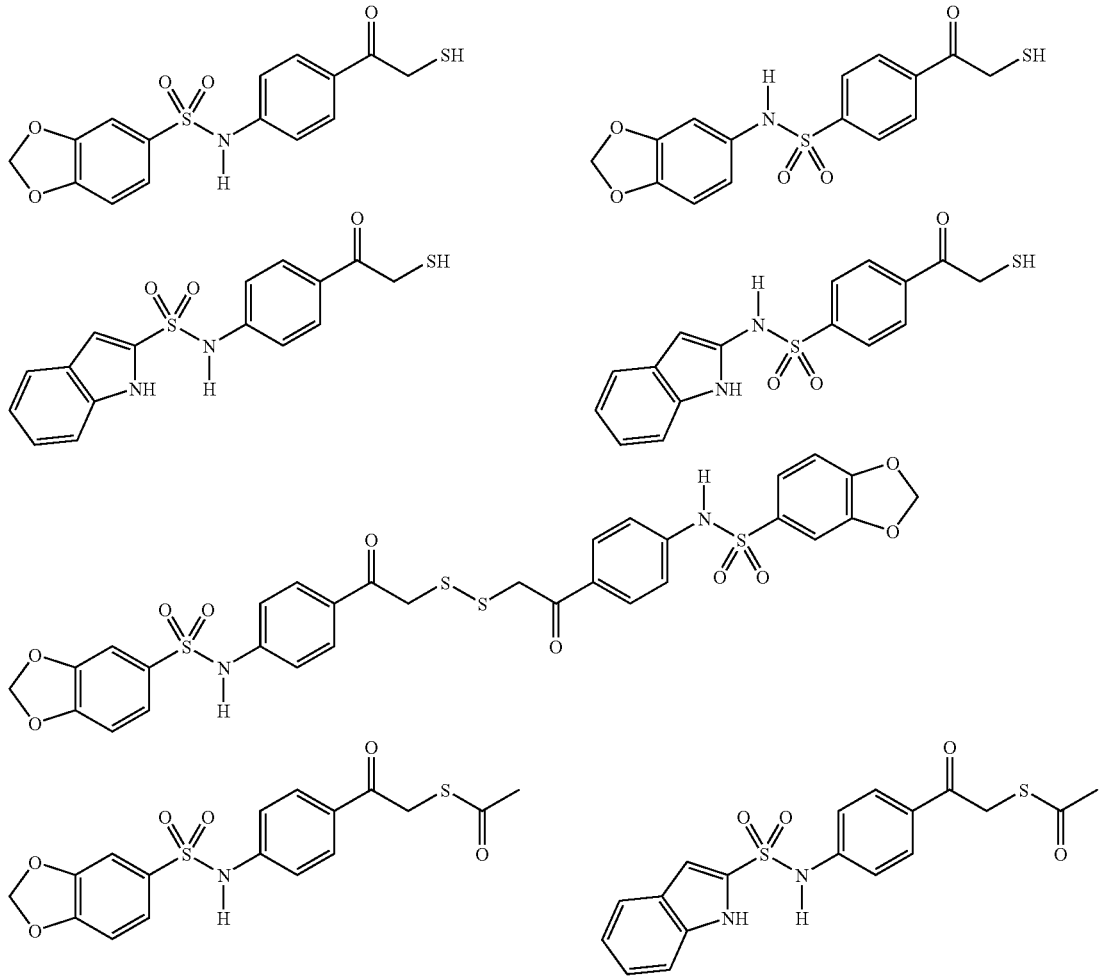

Uses of Compounds of the Invention

In accordance with one aspect, the present invention provides compounds of Formula I, where each compound is capable of inhibiting the catalytic activity of histone deacetylase (HDAC). In another aspect, the present invention provides pharmaceutical compositions comprising compounds HDAC comprising contacting said HDAC with a pharmaceutical composition containing the disclosed compounds.

In accordance with yet another aspect, the present invention provides a method of inhibiting the catalytic activity of HDAC comprising contacting said HDAC with a pharmaceutical composition of the disclosed compounds.

In accordance with yet another aspect, the present invention provides a method of identifying a carbonyl compound that modulates the cellular function of HDAC, comprising the steps of:
a) contacting cells expressing HDAC with a disclosed compound and
b) measuring an effect of the compound or composition.

In one embodiment, the present invention provides the above method wherein the effect is inhibition of the catalytic activity of HDAC. In a specific embodiment, the effect is histone hyperacetylation.

In one embodiment, the present invention provides the above method wherein the effect is a change in cell phenotype. In one embodiment, the present invention provides the above method wherein the effect is a change in cell proliferation.

In accordance with yet another aspect, the present invention provides a In accordance with yet another aspect, the present invention provides a In accordance with yet another aspect of the invention, the present invention provides methods and compositions for treating certain diseases or disease states. Methods and compositions are provided for using compounds of the invention for treating diseases or disease states including, but not limited to, cancers, autoimmune diseases, tissue damage, central nervous system disorders, neurodegenerative disorders, fibrosis, bone disorders, and disorders in which angiogenesis play a role in pathogenesis.

In accordance with one aspect, methods and compositions of the invention are used for treating cancer. In some embodiments, but without limitation, the term cancer refers to and is selected from disorders such as colon cancer, breast cancer, ovarian cancer, lung cancer and prostrate cancer, tumor invasion, tumor growth, tumor metastasis, and cancers of the oral cavity and pharynx (lip, tongue, mouth, pharynx), esophagus, stomach, small intestine, large intestine, rectum, liver and biliary passages, pancreas, larynx, bone, connective tissue, skin, cervix uteri, corpus endometrium, testis, bladder, kidney and other urinary tissues, eye, brain and central nervous system, thyroid and endocrine gland. The term "cancer" also encompasses Hodgkin's disease, non-Hodgkin's lymphomas, multiple myeloma and hematopoietic malignancies including leukemias (Chronic Lymphocytic Leukemia) and lymphomas including lymphocytic, granulocytic and monocytic. Additional types of cancers which may be treated using the compounds and methods of the invention include, but are not limited to, adrenocarcinoma, angiosarcoma, astrocytoma, acoustic neuroma, anaplastic astrocytoma, basal cell carcinoma, blastoglioma, chondrosarcoma, choriocarcinoma, chordoma, craniopharyngioma, cutaneous melanoma, cystadenocarcinoma, endotheliosarcoma, embryonal carcinoma, ependymoma, Ewing's tumor, epithelial carcinoma,. fibrosarcoma, gastric cancer, genitourinary tract cancers, glioblastoma multiforme, head and neck cancer, hemangioblastoma, hepatocellular carcinoma, hepatoma, Kaposi's sarcoma, large cell carcinoma, cancer of the larynx, leiomyosarcoma, leukemias, liposarcoma, lymphatic system cancer, lymphomas, lymphangiosarcoma, lymphangioendotheliosarcoma, medullary thyroid carcinoma, medulloblastoma, meningioma mesothelioma, myelomas, myxosarcoma neuroblastoma, neurofibrosarcoma, oligodendroglioma, osteogenic sarcoma, epithelial ovarian cancer, papillary carcinoma, papillary adenocarcinomas, parathyroid tumours, pheochromocytoma, pinealoma, plasmacytomas, retinoblastoma, rhabdomyosarcoma, sebaceous gland carcinoma, seminoma, skin cancers, melanoma, small cell lung carcinoma, squamous cell carcinoma, sweat gland carcinoma, synovioma, thyroid cancer, uveal melanoma, and Wilm's tumor.

In accordance with another aspect, methods and compositions of the invention are used for preventing neoplasias including, but not limited to, brain cancer, bone cancer, a leukemia, a lymphoma, epithelial cell-derived neoplasia (epithelial carcinoma) such as basal cell carcinoma, adenocarcinoma, gastrointestinal cancer such as lip cancer, mouth cancer, esophogeal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body. The neoplasia can be selected from gastrointestinal cancer, liver cancer, bladder cancer, pancreas cancer, ovary cancer, prostate cancer, cervical cancer, lung cancer, breast cancer and skin cancer, such as squamous cell and basal cell cancers.

In accordance with another aspect, methods and compositions of the invention are used for treating autoimmune diseases including, but not limited to: autoimmune disease that targets the nervous system, e.g., multiple sclerosis, myasthenia gravis, autoimmune neuropathies such as Guillain-Barré syndrome, autoimmune uveitis; autoimmune disease that targets the gastrointestinal system, e.g., Crohn's disease, ulcerative colitis, primary biliary cirrhosis; autoimmune hepatitis; autoimmune disease that targets the blood, e.g., autoimmune hemolytic anemia, pernicious anemia, autoimmune thrombocytopenia; autoimmune disease that targets endocrine glands, e.g., Type 1 or immune-mediated diabetes mellitus, Grave's disease, Hashimoto's thyroiditis, autoimmune oophoritis and orchitis, autoimmune disease of the adrenal gland; autoimmune disease that targets blood vessels, e.g., temporal arteritis, anti-phospholipid syndrome, vasculitides such as Wegener's granulomatosis, Behcet's disease; autoimmune disease that targets multiple organs including the musculoskeletal system, e.g., rheumatoid arthritis, scleroderma, polymyositis, dermatomyositis, spondyloarthropathies such as ankylosing spondylitis, Sjogren's syndrome; autoimmune disease that targets skin, e.g., psoriasis, dermatitis herpetiformis, pemphigus vulgaris, or vitiligo.

In accordance with another aspect, methods and compositions of the invention are used for treating disease states characterized by tissue damage, where the disease states include, but are not limited to, vascular diseases, migraine headaches, periarteritis nodosa, thyroiditis, aplastic anemia, Hodgkin's disease, sclerodoma, rheumatic fever, type I diabetes, neuromuscular junction disease including *myasthenia gravis,* white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like.

In accordance with another aspect, methods and compositions of the invention are used for treating the fibrosis which occurs with radiation therapy.

In accordance with another aspect, methods and compositions of the invention are used for treating subjects having adenomatous polyps, including those with familial adenomatous polyposis (FAP). Additionally, the present compounds and methods can be used to prevent polyps from forming in patients at risk of FAP.

In accordance with another aspect, methods and compositions of the invention are used for treating anemias or thalassemias including, without limitation, sickle cell anemia.

In accordance with another aspect, methods and compositions of the invention are used for treating a cardiovascular condition, e.g., cardiac hypertrophy and heart failure.

In accordance with another aspect, methods and compositions of the invention are used for treating diseases related to an inflammatory condition including, but not limited to, rhumatoid arthritis (RA), inflammatory bowel disease (IBD), ulcerative colitis and psoriasis.

In accordance with another aspect, methods and compositions of the invention are used for treating certain central nervous system disorders including, but not limited to, Parkinson's disease, Alzheimer's disease, Alzheimer's dementia, and central nervous system damage resulting from stroke, ischemia and trauma.

In accordance with another aspect, methods and compositions of the invention are used for treating a neurological or polyglutamine-repeat disorder including, but not limited to, Huntington's disease, Spinocerebellar ataxia 1 (SCA 1), Machado-Joseph disease (MJD)/Spinocerebella ataxia 3 (SCA 3), Kennedy disease/Spinal and bulbar muscular atrophy (SBMA) and Dentatorubral pallidolusyian atrophy (DRPLA).

In accordance with another aspect, methods and compositions of the invention are used for treating neurodegenerative disorders in which HDAC inhibition is useful include nerve degeneration or nerve necrosis in disorders such as hypoxia, hypoglycemia, epilepsy, and in cases of central nervous system (CNS) trauma (such as spinal cord and head injury), hyperbaric oxygen convulsions and toxicity, dementia e.g. pre-senile dementia, and AIDS-related dementia, cachexia, Sydenham's chorea, Huntington's disease, Amyotrophic Lateral Sclerosis, Korsakoffs disease, imbecility relating to a cerebral vessel disorder, sleeping disorders, schizophrenia, depression, depression or other symptoms associated with Premenstrual Syndrome (PMS), anxiety and septic shock.

In accordance with another aspect, methods and compositions of the invention are used for treating bone diseases, including bone disorders involving osteoclasts and chonrocytes. Without wishing to be limited by this theory, it is noted that HDAC activity regulates the process of osteoclastogenesis and chondrocyte differentiation, such that inhibitors of HDAC are also useful in the treatment of all bone disorders involving osteoclasts and chondrocytes.

In accordance with another aspect, methods and compositions of the invention are used for treating ophthalmic diseases and other diseases in which angiogenesis plays a role in pathogeneis, such as glaucoma, retinal ganglion degeneration, occular ischemia, retinitis, retinopathies, uveitis, ocular photophobia, and of inflammation and pain associated with acute injury to the eye tissue.

Methods and compositions of the invention are used for treating human and non-human subjects. Methods and compositions of the invention are suitable for veterinary uses in treating companion animals, exotic animals and farm animals, including mammals, rodents, and the like. In particular embodiments, methods and compositions of the invention are used for treating horses, dogs, and cats.

The terms "treat" or "treating" or "therapy" as used herein refer to (1) reducing the rate of process of a disease, or, in case of cancer reducing the size of the tumor; (2) inhibiting to some extent further progress of the disease, which in case of cancer may mean slowing to some extent, or preferably stopping, tumor metastasis or tumor growth; and/or, (3) relieving to some extent (or, preferably, eliminating) one or more symptoms associated with the disease. Thus, the term "therapeutically effective amount" as used herein refers to that amount of the compound being administered which will provide therapy or affect treatment.

In accordance with certain aspects of the invention, the compounds of the present invention act as anti-tumor compounds and/or inhibit the growth of a tumor, i.e., they are tumor-growth-inhibiting compounds. The terms "anti-tumor" and "tumor-growth-inhibiting," when modifying the term "compound," and the terms "inhibiting" and "reducing", when modifying the terms "compound" and/or "tumor," mean that the presence of the subject compound is correlated with at least the slowing of the rate of growth of the tumor. More preferably, the terms "anti-tumor," "tumor-growth-inhibiting," "inhibiting," and "reducing" refer to a correlation between the presence of the subject compound and at least the temporary cessation of tumor growth. The terms "anti-tumor," "tumor-growth-inhibiting," "inhibiting," and "reducing" also refer to, a correlation between the presence of the compound(s) of the invention and at least the temporary reduction in the mass of the tumor. It is understood that the effectiveness of compounds of the invention as anti-tumor, or tumor-inhibiting, agents may be contribute to their effectiveness in treating cancer, but that the compound of the invention may also act through other mechanisms to exert measured effects on cancer.

The term "cellular function" refers to the function of HDAC in the cell. The term "HDAC function" is generally understood to refer to interaction of HDAC with a natural binding partner, and is particularly understood to refer to catalytic activity. The "cellular function" of HDAC is understood to refer not only to the catalyic activity of HDAC in a cell, but also to the cellular effects of HDAC catalytic activity on the function of the cell. The term "catalytic activity", in the context of the invention, defines the rate at which HDAC deacetylates a substrate. Catalytic activity can be measured, for example, by determining the amount of a substrate converted to a product as a function of time. Deacetylation of a substrate occurs at the active-site of HDAC. The active-site is normally a cavity in which the substrate binds to HDAC and is deacetylated.

The term "substrate" as used herein refers to a molecule deacetylated by HDAC. The substrate is preferably a peptide and more preferably a protein. In some embodiments, the protein is a histone, whereas in other embodiments, the protein is not a histone.

The term "inhibit" refers to decreasing the cellular function of HDAC. It is understood that compounds of the present invention may inhibit the cellular function of HDAC by various direct or indirect mechanisms, in particular by direct or indirect inhibition of the catalytic activity of HDAC. The term "activates" refers to increasing the cellular function of HDAC.

The term "modulates" refers to altering the function of HDAC by increasing or decreasing the probability that a complex forms between HDAC and a natural binding partner. A modulator may increase the probability that such a complex forms between HDAC and the natural binding partner, or may increase or decrease the probability that a complex forms between HDAC and the natural binding partner depending on the concentration of the compound exposed to HDAC, or may decrease the probability that a complex forms between HDAC and the natural binding partner. A modulator may activate the catalytic activity of HDAC, or may activate or inhibit the catalytic activity of HDAC depending on the concentration of the compound exposed to HDAC, or may inhibit the catalytic activity of HDAC.

The term "complex" refers to an assembly of at least two molecules bound to one another. The term "natural binding partner" refers to polypeptides that bind to HDAC in cells. A change in the interaction between HDAC and a natural binding partner can manifest itself as an increased or decreased probability that the interaction forms, or an increased or decreased concentration of HDAC/natural binding partner complex.

The term "contacting" as used herein refers to mixing a solution comprising a compound of the invention with a liquid medium bathing the cells of the methods. The solution comprising the compound may also comprise another component, such as dimethylsulfoxide (DMSO), which facilitates the uptake of the compound or compounds into the cells of the methods. The solution comprising the compound of the invention may be added to the medium bathing the cells by utilizing a delivery apparatus, such as a pipet-based device or syringe-based device.

The term "monitoring" refers to observing the effect of adding the compound to the cells of the method. The effect can be manifested in a change in cell phenotype, cell proliferation, HDAC catalytic activity, substrate protein acetylation levels, gene expression changes, or in the interaction between HDAC and a natural binding partner.

The term "effect" describes a change or an absence of a change in cell phenotype or cell proliferation. "Effect" can also describe a change or an absence of a change in the catalytic activity of HDAC. "Effect" can also describe a change or an absence of a change in an interaction between HDAC and a natural binding partner.

The term "cell phenotype" refers to the outward appearance of a cell or tissue or the function of the cell or tissue. Examples of cell phenotype are cell size (reduction or enlargement), cell proliferation (increased or decreased numbers of cells), cell differentiation (a change or absence of a change in cell shape), cell survival, apoptosis (cell death), or the utilization of a metabolic nutrient (e.g., glucose uptake). Changes or the absence of changes in cell phenotype are readily measured by techniques known in the art.

Pharmaceutical Compositions

The present invention also relates to a pharmaceutical composition comprising a compound of the invention, or a pharmaceutically acceptable salt, solvate, amide, ester, or prodrug thereof, as described herein and a pharmaceutically acceptable carrier, diluent, or excipient, or a combination thereof.

The term "pharmaceutical composition" refers to a mixture of a compound of the invention with other chemical components, such as carriers, diluents or excipients. The pharmaceutical composition facilitates administration of the compound to an organism. Multiple techniques administering a compound exist in the art including, but not limited to: intravenous, oral, aerosol, parenteral, ophthalmic, pulmonary and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" refers to relatively nontoxic chemical compounds or agents. Such carriers may facilitate the incorporation of a compound into cells or tissues. For example, human serum albumin (HSA) is a commonly utilized carrier as it facilitates the uptake of many organic compounds into the cells or tissues of an organism.

The term "diluent" refers to chemical compounds that are used to dilute the compound of interest prior to delivery. Diluents can also be used to stabilize compounds because they can provide a more stable environment. Salts dissolved in buffered solutions (providing pH control) are utilized as diluents in the art. One commonly used buffered solution is phosphate buffered saline. It is a buffer found naturally in the blood system. Since buffer salts can control the pH of a solution at low concentrations, a buffered diluent rarely modifies the biological activity of a compound.

The compounds described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," 20th ed. Edited by Alfonso Gennaro, 2000.

Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or compression processes.

Pharmaceutical compositions for use in accordance with the present invention thus may be formulated in conventional manner using one or more pharmaceutically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

For intravenous injections, the agents of the invention may be formulated in aqueous solutions, preferably in pharmaceutically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, the agents of the invention may be formulated in aqueous or nonaqueous solutions, preferably with pharmaceutically compatible buffers or excipients. Such excipients are generally known in the art.

For oral administration, the compounds can be formulated readily by combining the active compounds with pharmaceutically acceptable carriers or excipients well known in the art. Such carriers enable the compounds of the invention to be formulated as tablets, powders, pills, dragees, capsules, liquids, gels, syrups, elixirs, slurries, suspensions and the like, for oral ingestion by a patient to be treated. Pharmaceutical preparations for oral use can be obtained by mixing one or more solid excipient with one or more compound of the invention, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal or sublingual administration, the compositions may take the form of tablets, lozenges, or gels formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form,. e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be a 10% ethanol, 10% polyethylene glycol 300, 10% polyethylene glycol 40 castor oil (PEG-40 castor oil) with 70% aqueous solution. This cosolvent system dissolves hydrophobic compounds well, and itself produces low toxicity upon systemic administration. Naturally, the proportions of a cosolvent system may be varied considerably without destroying its solubility and toxicity characteristics. Furthermore, the identity of the cosolvent components may be varied: for example, other low-toxicity nonpolar surfactants may be used instead of PEG-40 castor oil, the fraction size of polyethylene glycol 300 may be varied; other biocompatible polymers may replace polyethylene glycol, e.g., polyvinyl pyrrolidone; and other sugars or polysaccharides maybe included in the aqueous solution.

Alternatively, other delivery systems for hydrophobic pharmaceutical compounds may be employed. Liposomes and emulsions are well known examples of delivery vehicles or carriers for hydrophobic drugs. Certain organic solvents such as N-methylpyrrolidone also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free acid or base forms. 156.

The disclosed compounds can be used for the manufacture of a medicament for use in the treatment of a condition mediated by HDAC activity.

Routes of Administration

Suitable routes of administration include local or systemic routes of administration including, but not limited to, topical, transdermal, oral, rectal, transmucosal, pulmonary, ophthalmic, intestinal, parenteral, intramuscular, subcutaneous, intravenous, intramedullary, intrathecal, direct intraventricular, intraperitoneal, intranasal, or intraocular delivery. In certain embodiments, compounds of the invention are administered topically, e,g in an ointment, patch, nasal spray, or eye drops/ointment. In certain embodiments, compounds of the invention are delivered by intestinal, parenteral, intramuscular, subcutaneous, intravenous, intramedullary, intrathecal, direct intraventricular, intraperitoneal, intranasal, or intraocular injections.

Alternately, one may administer the compound in a local rather than systemic manner, for example, via injection of the compound directly into an organ, often in a depot or sustained release formulation. Furthermore, one may administer the drug in a targeted drug delivery system, for example, in a liposome coated with organ-specific antibody. The liposomes will be targeted to and taken up selectively by the organ.

General Synthetic Methods for Preparing Disclosed Compounds

Molecular embodiments of the present invention can be synthesized using standard synthetic techniques known to those of skill in the art. Compounds of the present invention can be synthesized using the general synthetic procedures set forth in Schemes I-IV.

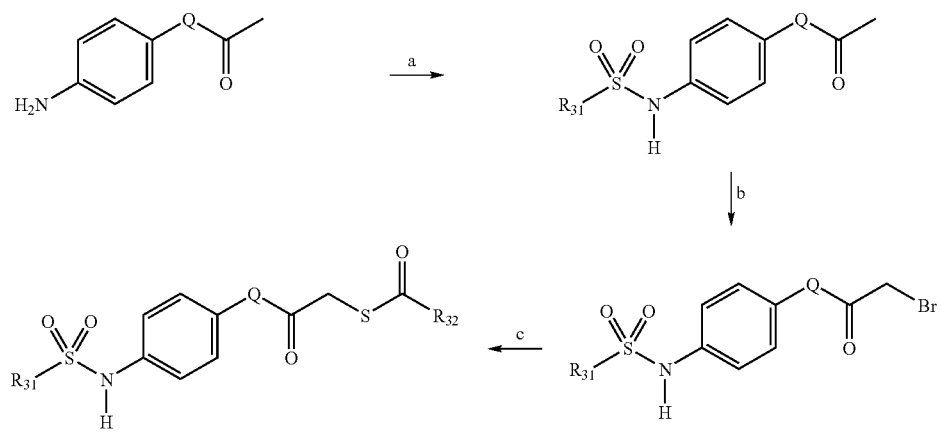

General procedure for sulfonamide: Scheme I

Reagents: (a) $R_{31}SO_2Cl$, Et3N, THF; (b) PTT, THF; (c) $KSCOR_{32}$, MeOH

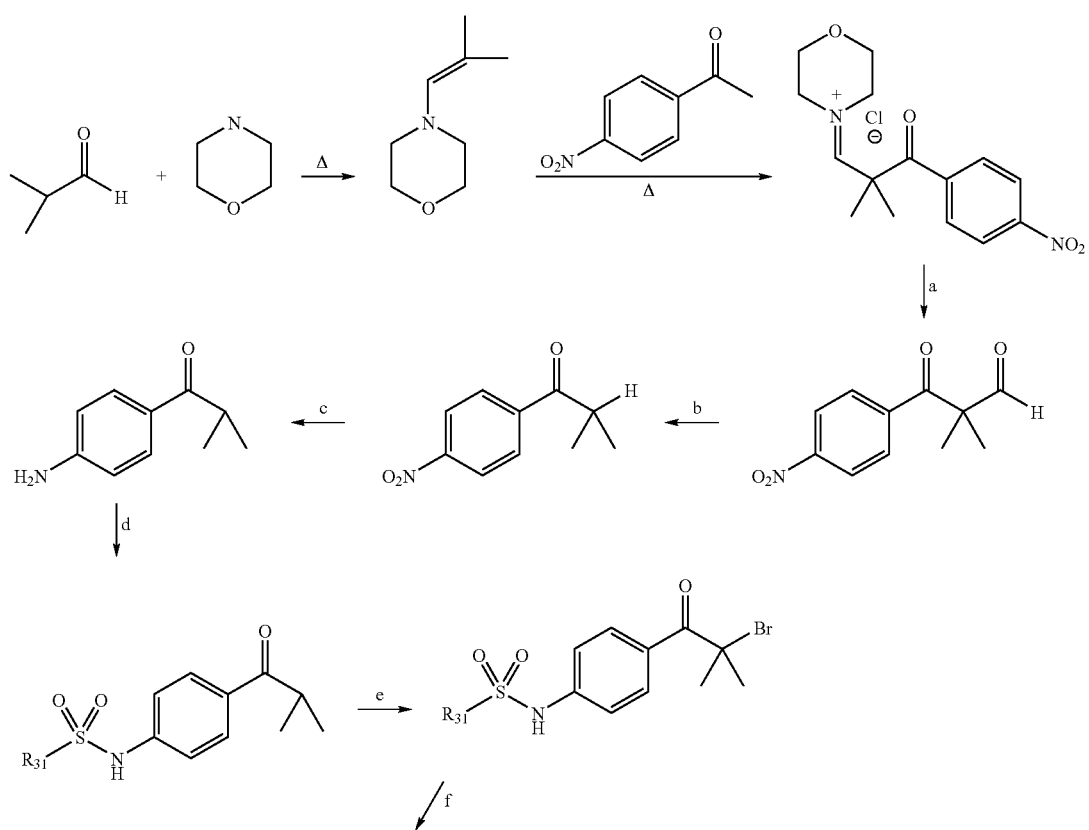

General procedure for alpha gem-dimethyl ketone: Scheme II

-continued
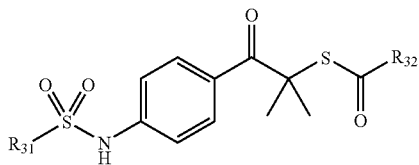
Reagents: (a) water, ether; (b) con. HCl, ether; (c) SnCl₂•2H₂O, DMF, Et₃N; (d) R₃₁SO₂Cl, pyridine, THF; (e) PTT, THF; (f) KSC(O)R₃₂, MeOH
Scheme III
General procedure for reversed sulfonamide (a):
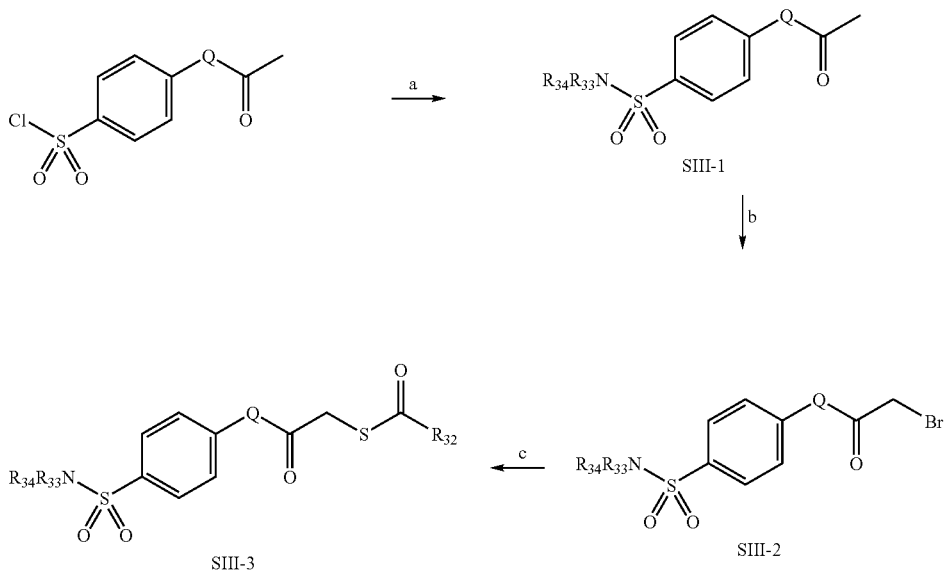
Reagents: (a) Amine (R₃₄R₃₃NH), THF, pyr; (b) THF, PTT; (c) MeOH, KSC(O)R₃₂
Scheme IV
General procedure for reversed sulfonamide (b)
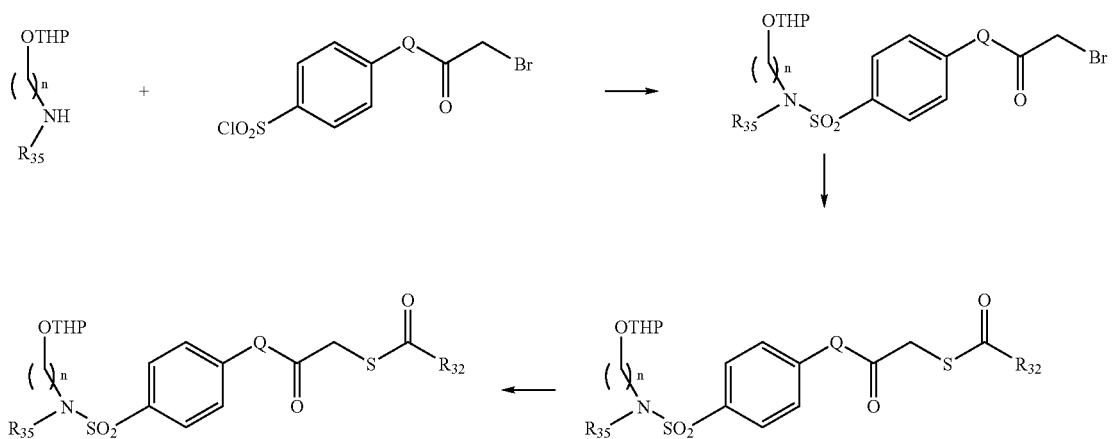

Scheme V
General Procedure for the Synthesis of Sulfoxides
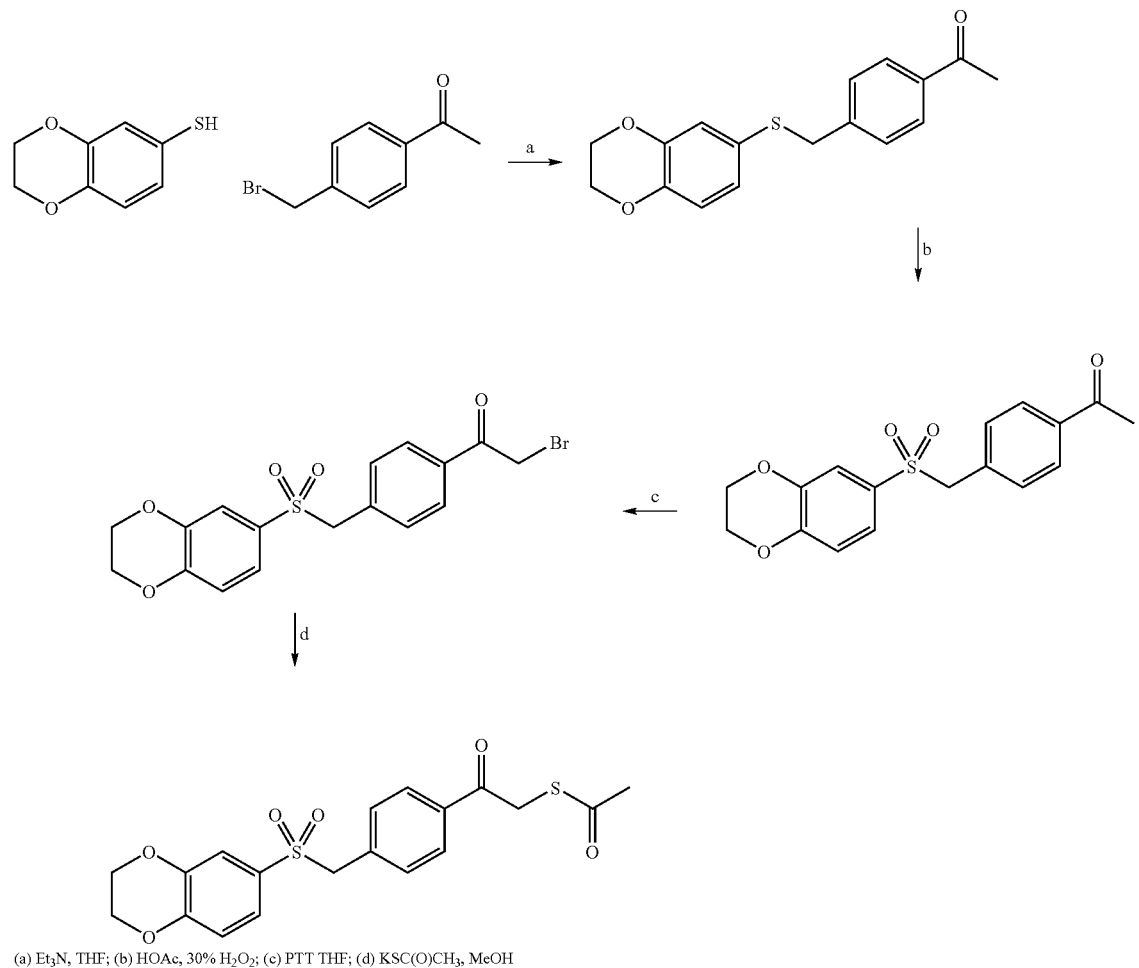
(a) Et$_3$N, THF; (b) HOAc, 30% H$_2$O$_2$; (c) PTT THF; (d) KSC(O)CH$_3$, MeOH
Scheme VI
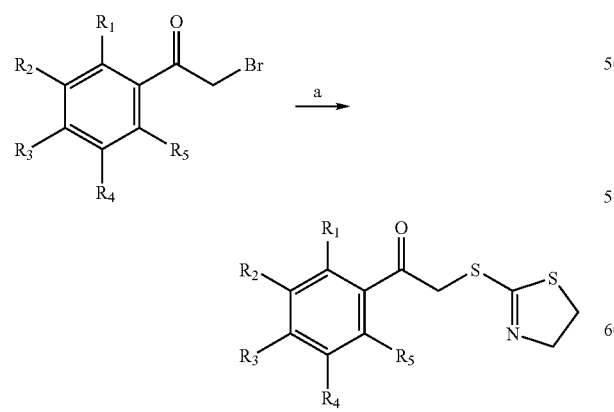
Reagents: (a) 2-mercaptothiazoline, NaOH, EtOH
Scheme VII
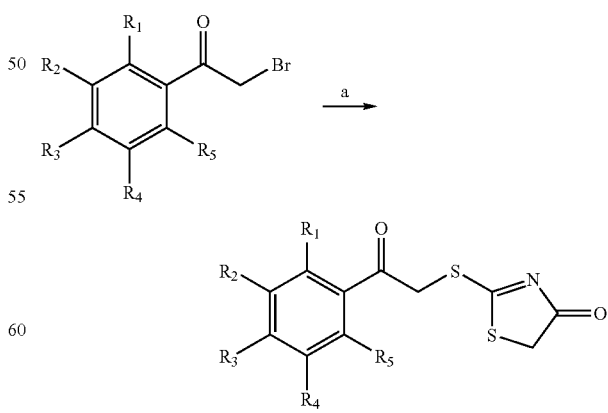
Reagents: a) EtOH, NaOH, Rhodanine Scheme VII
General Procedure for the Synthesis of Mercaptans and Disulfides:
Dynthesis of disulfide embodiments of the present invention.

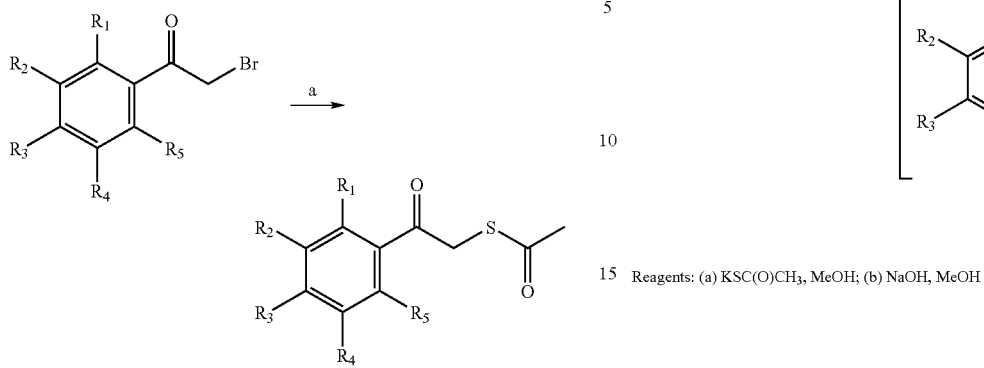

Reagents: (a) KSC(O)CH$_3$, MeOH; (b) NaOH, MeOH

Alternative general scheme for the synthesis of thiol (mercaptan) and disulfide embodiments of the present invention

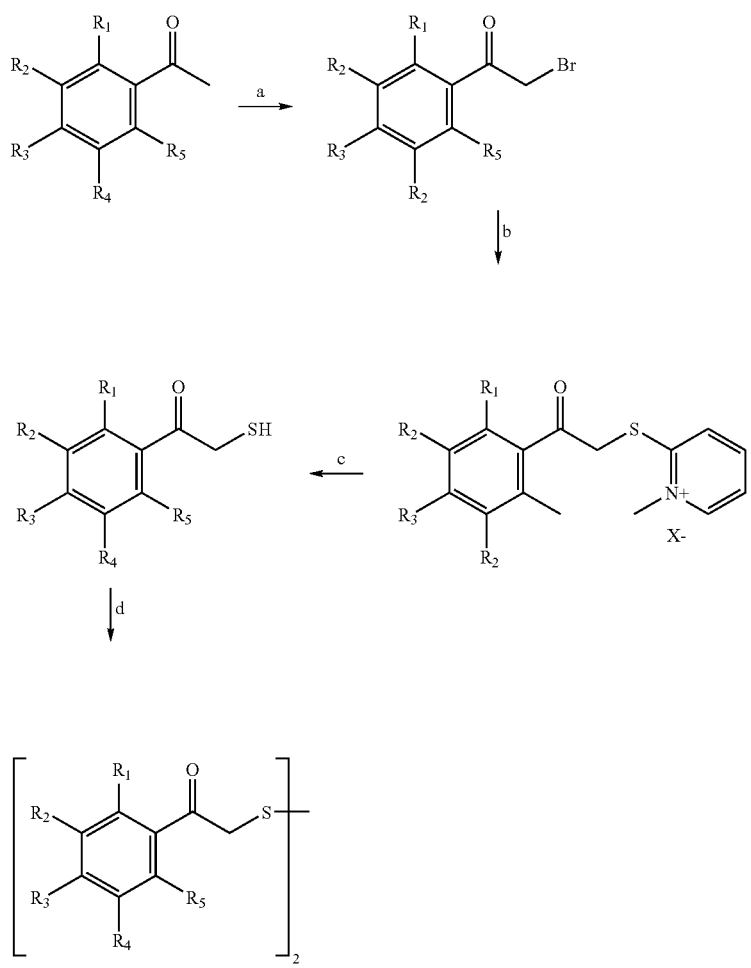

Reagents: (a) PTT, THF; (b) N-methyl 2-thiopyridone, EtOH; (c) NaOH, water; (d) MeOH, water.

EXAMPLES

The examples below are non-limiting and are merely representative of various aspects of the invention.

Example 1

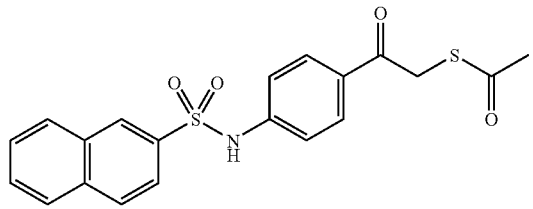

Thioacetic acid S-{2-[4-(naphthalene-2-sulfonylamino)-phenyl]-2-oxo-ethyl} ester The compound thioacetic acid S-{2-[4-(naphthalene-2-sulfonylamino)-phenyl]-2-oxo-ethyl} ester was synthesized according to Scheme I.

Step 1

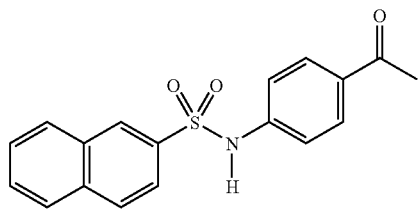

Naphthalene-2-sulfonic acid (4-acetyl-phenyl)-amide

4'-Amino acetophenone (1.20 g, 5.29 mmol) was dissolved in THF (8 ml) before pyridine (1.28 ml, 15.8 mmol) was added, leaving a yellow solution. The naphthalenesulfonylchloride (0.715 g, 5.29 mmol) was then added dropwise with stirring. After stirring for 5 hours, THF and pyridine were removed in vacuo. The desired sulfonamide (1.074 g, 3.30 mmol, 62%) was recrystallized from ethyl acetate and hexanes. It had LC-MS (ES+): 326 [MH]$^+$ m/e Step 2

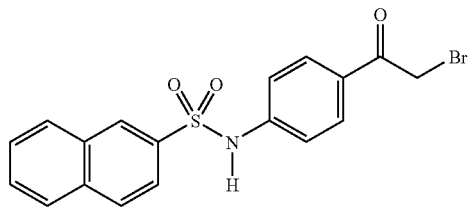

Naphthalene-2-sulfonic acid [4-(2-bromo-acetyl)-phenyl]-amide

The ketone from step 1 (1.074 g, 3.30 mmol mmol) was dissolved in THF (8 ml), and phenyltrimethylammonium tribromide (PTT) (1.24 g, 3.30 mmol) was added as a solid leaving an orange solution which began to deposit a white solid immediately. Stirring for 1.5 hours leaves a colorless mixture to which water (5 ml) was added. THF was then evaporated and the resulting aqueous mixture was extracted with ethyl acetate. Drying over $Na_2SO_4$ and evaporation leaves a white crystalline solid (85% desired mono-brominated material by LC-MS, 5% starting material, 10% dibrominated) suitable for the next step. LC-MS (ES+): 405, 403 m/e.

Step 3

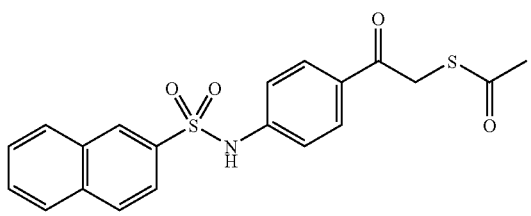

Thioacetic acid S-{2-[4-(naphthalene-2-sulfonylamino)-phenyl]-2-oxo-ethyl} ester The mono-brominated sulfonamide from step 2 (0.717 g, 1.77 mmol) was dissolved in methanol (4 ml) before potassium thioacetate (0.223 g, 1.94 mmol) was added as a solid. LC-MS of the resulting yellow solution shows the reaction is complete in minutes. Evaporation of the volatiles leaves a tan residue which was taken up into dichloromethane (4 ml), during which the disulfide of the thioacetic acid was deposited and filtered. The desired thioester could then be recrystallized from dichloromethane/hexanes (0.200 g, 0.501 mmol, 29%). $^1$H-NMR (DMSO): 11.10 (s, 1H), 8.62 (s, 1H), 8.22 (d, 1H), 8.15 (d, 1H), 8.05 (d,1H), 7.90 (m, 3H), 7.70 (q, 2H), 7.30 (d, 2H), 4.42 (d, 2H), 2.37 (s, 3H). LC-MS (ES+): 400 [MH]$^+$ m/e.

Example 2

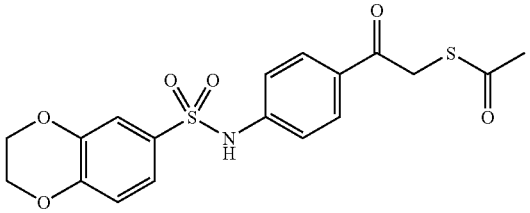

Thioacetic acid S-{2-[4-(2,3-dihydro-benzo[1,4]dioxine-6-sulfonylamino)-phenyl]-2-oxo-ethyl} ester The compound thioacetic acid S-{2-[4-(2,3-dihydro-benzo[1,4]dioxine-6-sulfonylamino)-phenyl]-2-oxo-ethyl} ester was synthesized according to the procedure described in the preparation of Example 1 using 2,3-dihydro-benzo[1,4]dioxine-6-sulfonyl chloride and potassium thioacetate. $^1$H-NMR (DMSO): 10.86 (s, 1H), 7.92 (d, 2H), 7.30 (q, 2H), 7.24 (d, 2H), 7.05 (d, 1H), 4.43 (s, 2H), 4.29 (t, 4H), 2.37 (s, 3H); LC-MS (ES+): 408 [MH]$^+$ m/e.

Example 3

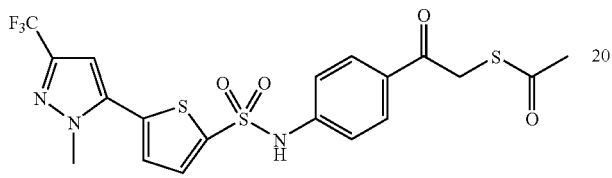

Thioacetic acid S-(2-{4-[5-(2-methyl-5-trifluoromethyl-2H-pyrazol-3-yl)-thiophene-2-sulfonylamino]-phenyl}-2-oxo-ethyl) ester The compound thioacetic acid S-(2-{4-[5-(2-methyl-5-trifluoromethyl-2H-pyrazol-3-yl)-thiophene-2-sulfonylamino]-phenyl}-2-oxo-ethyl) ester was synthesized according to the procedure described in the preparation of Example 1 using 5-(2-methyl-5-trifluoromethyl-2H-pyrazol-3-yl)-thiophene-2-sulfonyl chloride and potassium thioacetate. $^1$H-NMR (DMSO): 11.40 (s, 1H), 7.98 (d, 2H), 7.81 (s, 1H), 7.57 (s, 1H), 7.36 (d, 2H), 7.20 (s, 1H), 4.45 (s, 2H), 4.02 (s, 3H), 2.37 (s, 3H). LC-MS (ES+): 504 [MH]$^+$ m/e.

Example 4

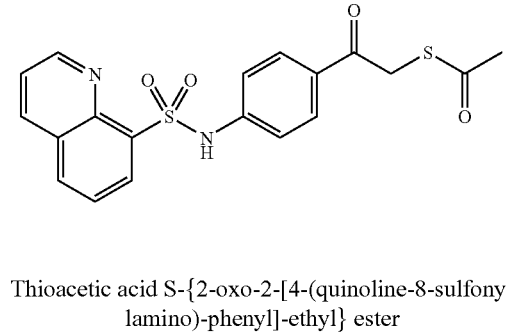

Thioacetic acid S-{2-oxo-2-[4-(quinoline-8-sulfonylamino)-phenyl]-ethyl} ester The compound thioacetic acid S-{2-oxo-2-[4-(quinoline-8-sulfonylamino)-phenyl]-ethyl} ester was synthesized according to the procedure described in the preparation of Example 1 using 8-quinolinesulfonyl chloride and potassium thioacetate. $^1$H-NMR (CDCl$_3$): 9.15 (d, 1H), 8.42 (d, 1H), 8.30 (d, 1H), 8.06 (d, 1H), 7.76 (d, 2H), 7.62 (m, 2H), 7.15 (d, 2H), 4.22 (s, 2H), 2.35 (s, 3H); LC-MS (ES+): 401 [MH]$^+$ m/e.

Example 5

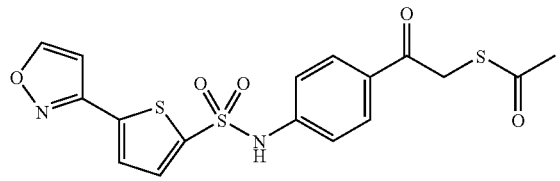

Thioacetic acid S-{2-[4-(5-isoxazol-3-yl-thiophene-2-sulfonylamino)-phenyl]-2-oxo-ethyl} ester The compound thioacetic acid S-{2-[4-(5-isoxazol-3-yl-thiophene-2-sulfonylamino)-phenyl]-2-oxo-ethyl} ester was synthesized according to the procedure described in the preparation of Example 1 using 5-isoxazol-3-yl-thiophene-2-sulfonyl chloride and potassium thioacetate. $^1$H-NMR (CDCl$_3$): 9.15 (d, 1H), 8.42 (d, 1H), 8.30 (d, 1H), 8.06 (d, 1H), 7.76 (d, 2H), 7.62 (m, 2H), 7.15 (d, 2H), 4.22 (s, 2H), 2.35 (s, 3H); LC-MS (ES+): 401 [MH]$^+$ m/e.

Example 6

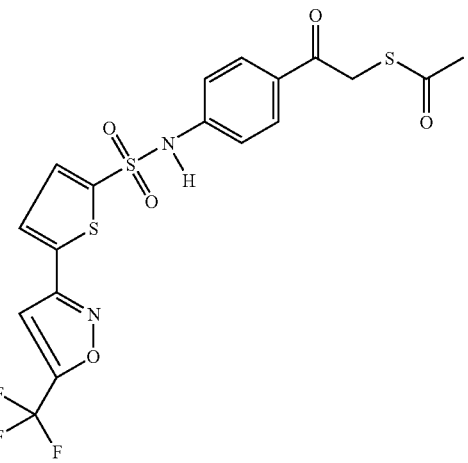

N-[4-(2-Mercapto-acetyl)-phenyl]-4-(5-[(Trifluoromethyl)isoxazole-3-yl]thiophene-sulfonanide The compound N-[4-(2-Mercapto-acetyl)-phenyl]-4-(5-[(Trifluoromethyl)isoxazole-3-yl]thiophene-sulfonamide was synthesized according to the procedure described in the preparation of Example 1 using 5-[5-(trifluoromethyl)isoxazol-3-yl)thiophene-2-sulfonyl chloride and potassium thioacetate. $^1$H-NMR: (CDCl$_3$) 8.0 (d, 2H), 7.64 (d, 1H), 7.42 (d, 1H), 7.29 (d, 2H), 6.98 (s, 1H), 4.38 (s, 2H), 2.43 (s, 3H); LC-MS (ES+): 490.6 [MH]+ m/e.

Example 7

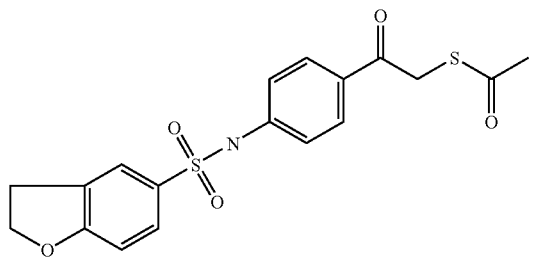

N-[4-(2-Mercapto-acetyl)-phenyl]-5-(2,3-Dihydrobenzo(b)furan-sulfonamide

The compound N-[4-(2-mercapto-acetyl)-phenyl]-5-(2,3-dihydrobenzo(b)furan-sulfonamide was synthesized according to the procedure described in the preparation of Example 1 using 2,3-dihydrobenzo(b)furan-5-sulfonyl chloride and potassium thioacetate. $^1$H-NMR: (CDCl$_3$) 7.82 (d, 2H), 7.70 (s, 1H), 7.32 (dd, 1H), 7.22 (d, 2H), 6.79 (dd, 1H), 4.38 (s, 2H), 3.21 (t, 2H), 3.20 (t, 2H), 2.41 (s, 3H); LC-MS (ES+): 391.7 [MH]+ m/e.

Example 8

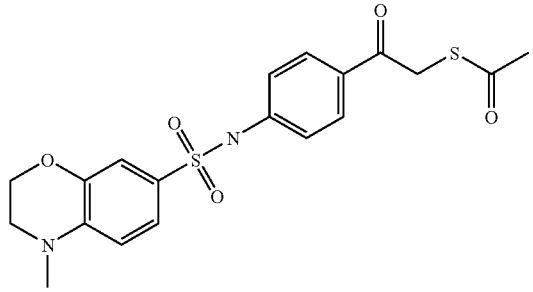

N-[4-(2-Mercapto-acetyl)-phenyl]-7-(4-Methyl-3,4-Dihydro-2H-1,4-Benzoxazine)-sulfonamide The compound N-[4-(2-mercapto-acetyl)-phenyl]-7-(4-Methyl-3,4-Dihydro-2H-1,4-Benzoxazine)-sulfonamide was synthesized according to the procedure described in the preparation of Example 1 using 4-methyl-3,4-dihydro-2H-1,4-benzoxazine-7-sulfonyl chloride and potassium thioacetate. $^1$H-NMR: (CDCl$_3$) 7.90 (d, 2H), 7.24 (d, 2H), 7.20 (d, 2H), 7.16 (s, 1H), 6.80 (d, 1H), 4.38 (t, 2H), 4.36 (s, 2H), 3.31 (t, 2H), 2.88 (s, 3H), 2.41 (s, 3H); LC-MS (ES+): 420.2 [MH]+ m/e.

Example 9

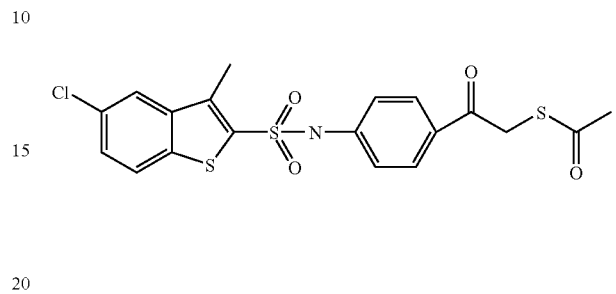

N-[4-(2-Mercapto-acetyl)-phenyl]-2-(5-Chloro-3-Methylbenzo(b)-thiophene)-sulfonamide The compound N-[4-(2-mercapto-acetyl)-phenyl]-2-(5-Chloro-3-Methylbenzo(b)-thiophene)-sulfonamide was synthesized according to the procedure described in the preparation of Example 1 using 5-Chloro-3-Methylbenzo(b)-thiophene-2-sulfonyl chloride and potassium thioacetate. $^1$H-NMR: (CDCl$_3$) 7.96 (d, 2H), 7.79 (d, 1H), 7.49 (d, 1H), 7.25 (d, 2H), 7.24(s, 1H), 4.38 (s, 2H), 2.60 (s, 3H), 2.42 (s, 3H); LC-MS (ES+): 454.3 [MH]+ m/e.

Example 10

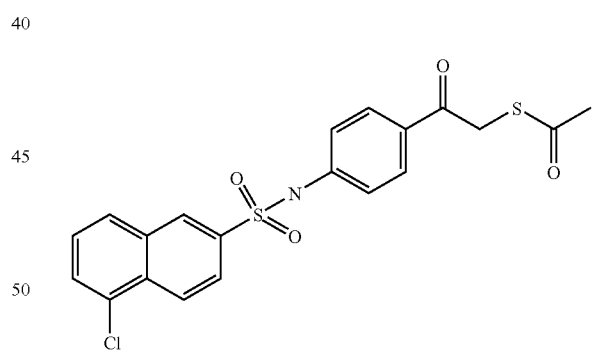

N-[4-(2-Mercapto-acetyl)-phenyl]-2-(6-Chloronaphthalene)-sulfonamide

The compound N-[4-(2-mercapto-acetyl)-phenyl]-2-(5-Chloro-3-Methylbenzo(b)-thiophene)-sulfonamide was synthesized according to the procedure described in the preparation of Example 1 using 5-Chloro-3-Methylbenzo(b)-thiophene-2-sulfonyl chloride and potassium thioacetate. $^1$H-NMR: (DMSO) 10.98 (s, 1H), 8.71 (s, 1H), 8.40 (d, 1H), 8.23 (d, 1H), 8.01 (d, 1H), 7.91 (d, 1H), 7.89 (d, 2H), 7.69 (d, 1H), 7.30 (d, 2H), 4.40 (s, 2H), 2.40 (s, 3H); LC-MS (ES+): 434 [MH]+ m/e.

Example 11

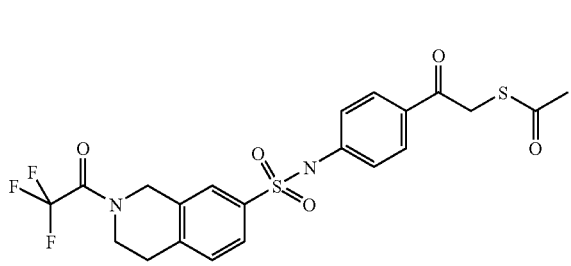

N-[4-(2-Mercapto-acetyl)-phenyl]-7-[1,2;3,4-Tetrahydro-2-(Trifluoroacetyl)-isoquinoline]-sulfonamide The compound N-[4-(2-Mercapto-acetyl)-phenyl]-7-[1,2,3,4-Tetrahydro-2-(Trifluoroacetyl)-isoquinoline]-sulfonamide was synthesized according to the procedure described in the preparation of Example 1 using 1,2,3,4-Tetrahydro-2-(Trifluoroacetyl)-isoquinoline-7-sulfonyl chloride and potassium thioacetate. $^1$H-NMR: (CDCl$_3$) 7.92 (d, 2H), 7.77 (s, 1H), 7.75 (d, 1H), 7.34 (d, 1H), 7.21 (d, 2H), 4.83 (s, 2H), 4.38 (s, 2H), 3.91 (t, 2H), 3.04 (t, 2H), 2.41 (s, 3H); LC-MS (ES+): 500.6 [MH]+ m/e.

Example 12

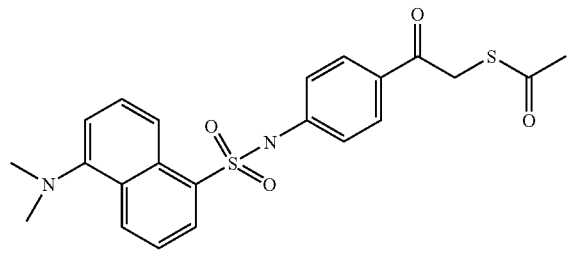

N-[4-(2-Mercapto-acetyl)-phenyl]-1-Dansyl-sulfonamide

The compound N-[4-(2-mercapto-acetyl)-phenyl]-1-dansyl-sulfonamide was synthesized according to Scheme I using dansyl chloride and potassium thioacetate. $^1$H-NMR: (CDCl$_3$) 8.61 (d, 1H), 8.50 (d, 1H), 8.38 (d, 1H), 7.84 (d, 2H), 7.70 (dd, 1H), 7.65 (dd, 1H), 7.41 (d, 1H), 7.11 (d, 2H), 4.25 (s, 2H), 3.12 (s, 6H), 2.40 (s, 3H); LC-MS (ES+): 442.6 [MH]+ m/e.

Example 13

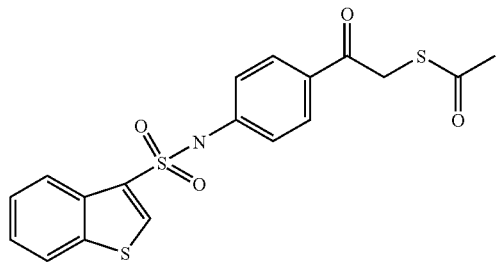

N-[4-(2-Mercapto-acetyl)-phenyl]-3-(1-Benzothiophene)-sulfonamide

The compound N-[4-(2-mercapto-acetyl)-phenyl]-3-(1-Benzothiophene)-sulfonamide was synthesized according to the procedure described in the preparation of Example 1 using 1-Benzothiophene-3-sulfonyl chloride and potassium thioacetate. $^1$H-NMR: (CDCl$_3$) 8.33 (s, 1H), 8.20 (d, 1H), 7.90 (d, 2H), 7.88 (d, 1H), 7.57 (dd, 1H), 7.54 (dd, 1H), 7.19 (d, 2H), 4.32 (s, 2H), 2.41 (s, 3H); LC-MS (ES+): 405.2 [MH]+ m/e.

Example 14

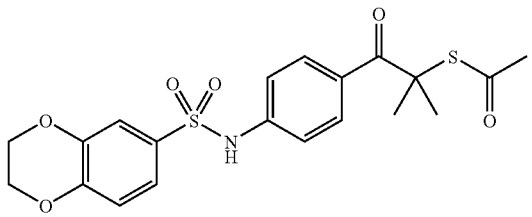

Thioacetic acid-S-{2-[4-(2,3-dihydro-benzo[1,4]dioxine-6sulfonylamino)-phenyl]-1,1-dimethyl-2-oxo-ethyl} ester The compound thioacetic acid-S-{2-[4-(2,3-dihydrobenzo[1,4]dioxine-6-sulfonylamino)-phenyl]-1,1-dimethyl-2-oxo-ethyl} ester was synthesized according to Scheme II.

Step 1

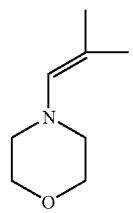

1-Morpholino-isobutene

Morpholine (21.78 g, 0.25 mol) and isobutyraldehyde (18.02 g, 0.25 mol) were heated to reflux as a neat mixture, in a 100 ml round bottom flask with a Dean Stark Trap attached. After the mixture was refluxed overnight, the reaction mixture was purified by vacuum distillation. The pure enamine product (15.01 g, 0.10 mol, 42%) had a $^1$H-NMR (CDCl$_3$): 5.32 (s, 1H), 3.72 (t, 4H), 2.87 (t, 4H), 1.81 (s, 3H), 1.68 (s, 3H) It had LC-MS (ES+): 142 [MH]$^+$ m/e.

Step 2

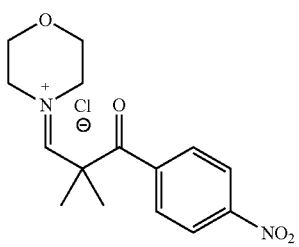

4-[2,2-Dimethyl-3-(4-nitro-phenyl)-3-oxo-propylidene]-morpholin-4-ium chloride:

The enamine from step 1 (10.1 g, 0.0715 mol) was dissolved in p-dioxane (25 ml). The resulting solution was then added to a stirred solution of p-nitrobenzoyl chloride (13.27 g, 0.0715 mol) in 25 ml of p-dioxane in a dropwise manner. When the evolution of heat subsided the mixture was refluxed for 1 hr. The reaction was then removed from heat and allowed to stand overnight at room temp. The desired immonium salt precipitated. The precipitate was washed with ether and dried under vacuum to yield 21.06 g (0.064 mol, 92%) of crude material that was carried forward.

Step 3

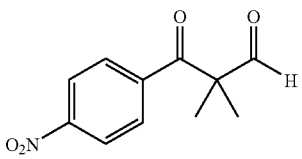

α-(p-Nitrobenzoyl)isobutyraldehyde

The immonium salt from step 2 (21.06 g, 0.064 mol) was stirred in 60 ml of a 50/50 mixture of H$_2$O and diethyl ether overnight at room temperature. The organic layer was then separated from the aqueous layer and dried over Na$_2$SO$_4$. Evaporation of the organic layer leaves the desired aldehyde as a crude liquid (14.01 g, 0.063 mol, 98%) with $^1$H-NMR (DMSO): 9.83 (s, 1H), 8.31 (d, 2H), 7.90 (d, 2H), 1.42 (s, 6H)

Step 4

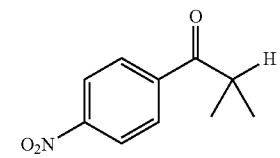

p-Nitroisobutyrophenone

The aldehyde from step 3 (14.0 g, 0.063 mol), used as a crude, was dissolved in 35 ml of diethyl ether. 15 ml of concentrated HCl is then added dropwise to the organic layer with rapid stirring. The reaction is allowed to stir overnight at room temperature. The organic layer was washed with H$_2$O and dried over Na$_2$SO$_4$. Removal of volatiles left a crude oil that was purified by column chromatography using a mobile phase of 50/50 ethylacetate in hexanes. The desired p-Nitroisobutyrophenone was a yellow solid (2.72 g, 0.014 mol, 22%) with a $^1$H-NMR (DMSO): 8.30 (d, 2H), 8.18 (d, 2H), 3.70 (m, 1H), 1.17 (s, 6H)

Step 5

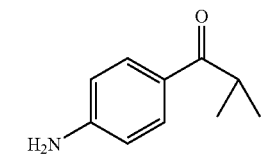

1-(4-Amino-phenyl)-2-methyl-propan-1-one p-Nitroisobutyrophenone from step 4 (1.0 g, 0.0058 mol), was dissolved in DMF (5 ml). SnCl$_2$.2H$_2$O (4.67 g, 0.0207 mol) is added and the reaction is stirred at room temperature. After 4 hours the reaction was poured into 100 ml of ethyl acetate. Excess Et$_3$N (4 ml) was added and a white, solid precipitate formed. The suspension was filtered through celite. Evaporation of the filtrate left a yellow solid which was purified by column chromatography. The resulting crystalline solid (0.700 g, 4.2 mmol, 82%) had a $^1$H-NMR (DMSO): 7.71 (d, 2H), 6.58 (d, 2H), 6.03 (s, 2H), 3.45 (m, 1H), 1.06 (s, 6H)

Step 6

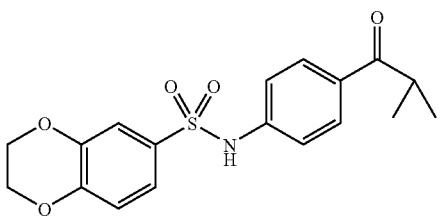

6

2,3-Dihydro-benzo[1,4]dioxine-6-sulfonic acid (4-isobutyryl-phenyl)-amide

The aniline (0.774 g, 4.75 mmol) was dissolved in THF (10 ml) and pyridine (1.15 ml, 0.014 mol). The dioxane (1.171 g, 4.99 mmol) was added to the solution and the reaction was stirred overnight at room temperature. After removal of the THF and pyridine the desired sulfonamide (6) was recrystallized from ethyl acetate and hexanes. The sulfonamide (1.33 g, 3.67 mmol, 75%) had a LC-MS (ES+): 362 [MH]$^+$ m/e.

Step 7

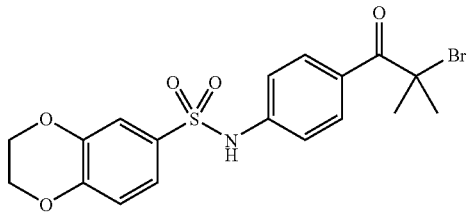

2,3-Dihydro-benzo[1,4]dioxine-6-sulfonic acid [4-(2-bromo-2-methyl-propionyl)-phenyl]-amide Sulfonamide from step 6 (1.33 g, 3.67 mmol) was dissolved in THF (8 ml), and phenyltrimethylammonium tribromide (PTT) (1.37 g, 3.67 mmol) was added as a solid leaving an orange solution which began to deposit a white solid immediately. Stirring for 1.5 hours leaves a colorless mixture to which water (5 ml) was added. THF was then evaporated and the resulting aqueous mixture was extracted with ethyl acetate. Drying over Na$_2$SO$_4$ and evaporation leaves a white crystalline solid (100% desired mono-brominated material by LC-MS) suitable for the next step. It had LC-MS (ES+): 439, 441 [MH]$^+$ m/e.

Step 8

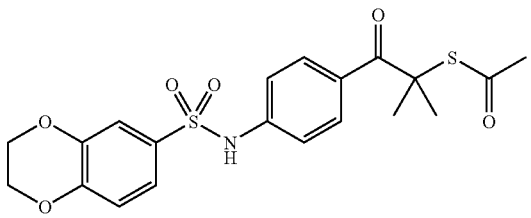

Thioacetic acid-S-{2-[4-(2,3-dihydro-benzo[1,4]dioxine-6-sulfonylamino)-phenyl]-1,1-dimethyl-2-oxo-ethyl} ester The mono-brominated sulfonamide from step 7 (0.140 g, 0.318 mmol) was reacted with thioacetate (0.039 g, 0.350 mmol) as previously described. The reaction was purified by column chromatography to yield a white crystalline solid (0.050 g, 0.114 mmol, 36%) that had a $^1$H-NMR (CDCl$_3$): 8.00 (d, 2H), 7.38 (m, 2H), 7.08 (d, 2H), 6.92 (d, 1H), 6.79 (s, 1H), 4.31 (m, 4H), 2.15 (s, 3H), 1.70 (s, 6H). It had LC-MS (ES+): 436 [MH]$^+$ m/e

Example 15

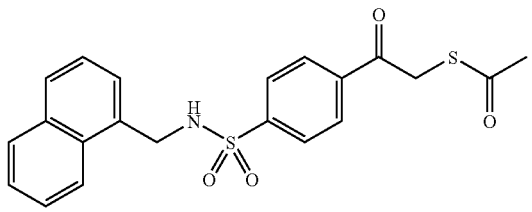

Thioacetic acid S-(2-{4-[(naphthalen-1-ylmethyl)-sulfamoyl]-phenyl}-2-oxo-ethyl) ester The compound thioacetic acid S-(2-{4-[(naphthalen-1-yl-methyl)-sulfamoyl]-phenyl}-2-oxo-ethyl) ester was synthesized according to Scheme III.

Step 1

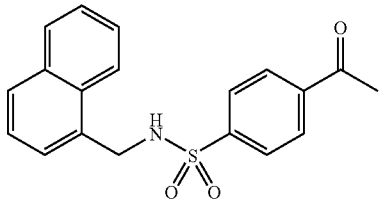

4-Acetyl-N-naphthalen-1-ylmethyl-benzenesulfonamide

1-Napthalene-methylamine (1.118 g, 7.11 mmol) was dissolved in THF before pyridine (1.725 ml, 21.3 mmol) was added. 4-Acetyl-benzenesulfonyl chloride (1.554 g, 7.11 mmol) was then added as a solid, and the resulting dark solution was stirred for 10 minutes. The volatiles were then removed, and the resulting residue was suspended in THF. Excess Et$_3$N was then added, and the mixture was stirred for several minutes before the solids were filtered. The mother liquor was then evaporated to a solid which was recrystalized in ethylacetate and hexanes to yield 0.5697 g (0.00167 mol, 23%) of desired compound that was pure enough for the next step. LC-MS (ES+): 340 [MH]$^+$ m/e.

Step 2

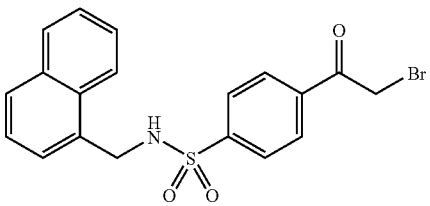

105

4-(2-Bromo-acetyl)-N-naphthalen-1-ylmethyl-benzenesulfonamide

The ketone (0.569 g, 1.67 mmol) from step 1 was dissolved in THF (4 ml), and phenyltrimethylammonium tribromide (PTT) (0.630 g, 1.67 mmol) was added as a solid leaving an orange solution which began to deposit a white solid immediately. Stirring for 1.5 hours leaves a colorless mixture to which water (5 ml) was added. THF was then evaporated and the resulting aqueous mixture was extracted with ethyl acetate. Drying over $Na_2SO_4$ and evaporation leaves a white crystalline solid (80% desired mono-brominated material by LC-MS, 5% starting material, 15% dibrominated) suitable for the next step. LC-MS (ES−): 416, 418 m/e.

Step 3

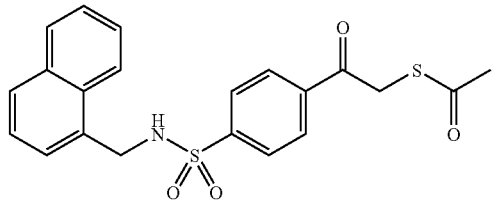

Thioacetic acid S-(2-{4-[(naphthalen-1-ylmethyl)-sulfamoyl]-phenyl}-2-oxo-ethyl) ester The mono-brominated reverse sulfonamide from step 2 was reacted with thioacetic acid as previously described the preparation of Example 14 Step 8 to yield the desired final product. $^1$H-NMR (DMSO): 8.44 (t, 1H), 8.16 (d, 2H), 8.05 (d, 1H), 7.97 (m, 3H), 7.90 (t, 1H), 7.55 (m, 2H), 7.43 (d, 2H), 4.59 (s, 2H), 4.48 (d, 2H), 2.43 (s, 3H) LC-MS (ES+): 414 [MH]$^+$ m/e.

Example 17

106

Thioacetic acid S-(2-{4-[[2-(3a,7a-dihydro-1H-indol-3-yl)-ethyl]-(3-hydroxy-propyl)-sulfamoyl]-phenyl}-2-oxo-ethyl) ester The compound Thioacetic acid S-(2-{4-[[2-(3a,7a-dihydro-1H-indol-3-yl)-ethyl]-(3-hydroxy-propyl)-sulfamoyl]-phenyl}-2-oxo-ethyl) ester was synthesized according to Scheme IV.

Example 18

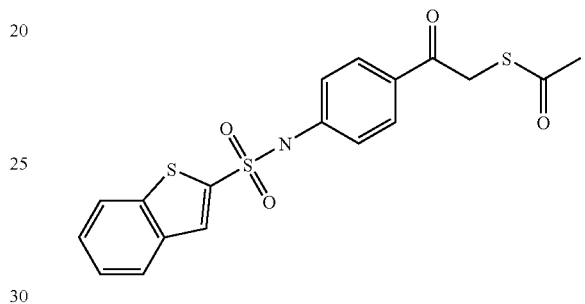

N-[4-(2-Mercapto-acetyl)-phenyl]-2-(1-Benzothiophene)-sulfonamide

The compound N-[4-(2-Mercapto-acetyl)-phenyl]-2-(1-Benzothiophene)-sulfonamide was synthesized according to the method described in the preparation of Example 1. $^1$H-NMR: (CDCl$_3$) 8.11 (s, 1H), 7.92 (d, 2H), 7.89 (dd, 1H), 7.82 (dd, 1H), 7.53 (d, 1H), 7.45 (d, 1H), 7.31 (d, 2H), 4.37 (s, 2H), 2.42 (s, 3H); MS: (405.2)

Example 19

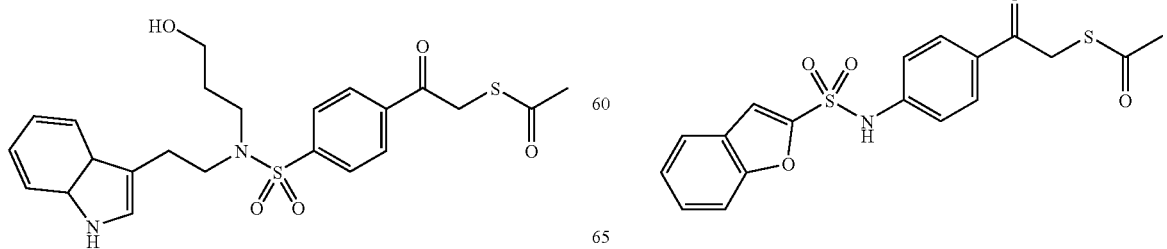

Thioacetic acid S-{2-[4-(benzofuran-2-sulfonylamino)-phenyl]-2-oxo-ethyl} ester

The compound thioacetic acid S-{2-[4-(benzofuran-2-sulfonylamino)-phenyl]-2-oxo-ethyl} ester was synthesized according to the method described in the preparation of Example 1. $^1$H-NMR (DMSO): 11.6, (s, 1H), 7.96 (d, 2H), 7.86 (s, 1H), 7.80 (d, 1H), 7.2 (d, 1H), 7.57 (t, 1H), 7.40 (t, 1H) 7.34 (d, 2H), 4.43 (s, 2H), 2.37 (s, 3H). LC-MS (ES+): 390 [MH]$^+$ m/e.

Example 20

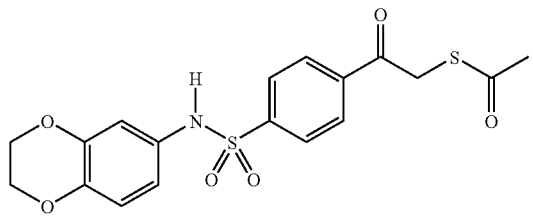

Thioacetic acid S-{2-[4-(2,3-dihydro-benzol[1,4] dioxin-6-ylsulfamoyl)-phenyl]-2-oxo-ethyl} ester The compound thioacetic acid S-{2-[4-(2,3-dihydro-benzo[1,4]dioxin-6-ylsulfamoyl)-phenyl]-2-oxo-ethyl}ester was synthesized according to the method described in the preparation of Example 15. $^1$H-NMR (DMSO): 10.20 (s, 1H), 8.08 (d, 2H), 7.81 (d, 2H), 6.71 (d, 1H), 6.60 (s, 1H), 6.51 (s, 1H), 4.55 (s, 2H), 4.08 (s, 4H), 2.40 (s, 3H); LC-MS (ES+): 408 [M]$^+$ m/e.

Example 21

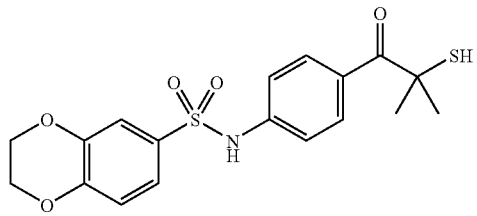

2,3-Dihydro-benzo[1,4]dioxine-6-sulfonic acid [4-(2-mercapto-2-methyl-propionyl)-phenyl]-amide The compound of Example 14 (60 mg, 0.14 mmol) was dissolved in methanol (2 ml) before 5 M NaOH was added (150 µl). The resulting yellow solution was allowed to stir at room temperature for 30 minutes. The desired compound was isolated by prep-HPLC as a white solid. $^1$H-NMR (DMSO):
10.73 (s, 1H), 7.93 (d, 2H), 7.31 (m, 2H), 7.17 (d, 2H), 7.02 (d, 1H), 4.28 (q, 4H), 3.78 (s, 1H), 1.57 (s, 6H). LC-MS (ES+): 394 [MH]$^+$ m/e.

Example 22

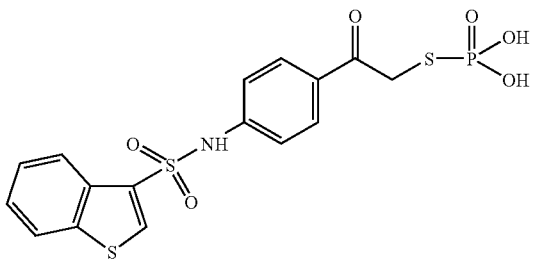

Thiophosphoric acid S-{2-[4-(benzo[b]thiophene-3-sulfonylamino)-phenyl]-2-oxo-ethyl}ester A solution of the compound from Example 13, step 2 (100 mg, 0.244 mmol) in DMF (0.5 mL) was transferred to an 8 mL septa sealed vial equipped with stir bar and stirred at room temperature for 5 min. Trisodium thiophosphate (88 mg, 0.49 mmol) as a suspension in H$_2$O (2 mL) was then added and the reaction stirred at room temperature overnight (pH was checked by litmus after 5 hr and determined to be neutral). The light brown mixture was added to 5 mL of H$_2$O and the pH (slightly basic) neutralized with 1N HCl. Upon extraction of the aqueous layer with DCM, the product as a beige solid crashed out of solution. The solids were filtered off and triturated with EtOAc, then CH$_2$Cl$_2$. Volatiles were removed in vacuo to afford the desired product (66 mg) as a beige powder. $^1$H-NMR: (CDCl$_3$) 8.33 (d, 1H), 8.24 (s, 1H), 7.81 (d, 2H), 7.71 (d, 1H), 7.42 (dd, 1H), 7.40 (dd, 1H), 7.06 (d, 2H), 4.10 (d, 2H), 1.89 (s, 2H) ppm. MS: (442.97)

Example 23

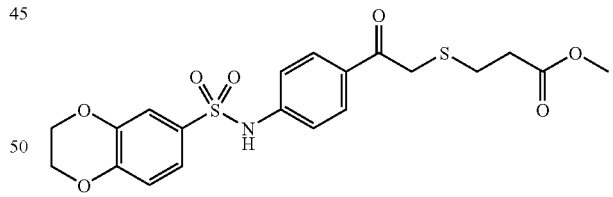

3-{2-[4-(2,3-Dihydro-benzo[1,4]dioxine-6-sulfonylamino)-phenyl]-2-oxo-ethylsulfanyl}-propionic acid methyl ester Thioacetic acid S-{2-oxo-2-[4-(2,3-dihydro-benzo[1,4]dioxine-6-sulfonylamino)-phenyl]-ethyl}ester (200 mg, 0.46 mmol) was dissolved in methanol (3 ml) before 5 M NaOH was added (300 µl), leaving a yellow solution of the liberated thiol. Methyl acrylate (100 µl, 1.11 mmol) was then added, and the reaction was quenched with 6 M HCl after stirring for 15 min. The desired product was purified by prep-HPLC, and isolated as a white, crystalline solid. $^1$H-NMR (DMSO): 10.81 (s, 1H), 7.87 (d, 2H), 7.31 (m, 2H), 7.20 (d, 2H), 7.02 (d, 1H), 4.28 (m, 4H), 3.94 (s, 2H), 3.57 (s, 3H), 2.64 (m, 4H). LC-MS (ES+): 452 [MH]+ m/e.
The following compounds can be made using the methods as described above and when made should have similar activity as those made above.
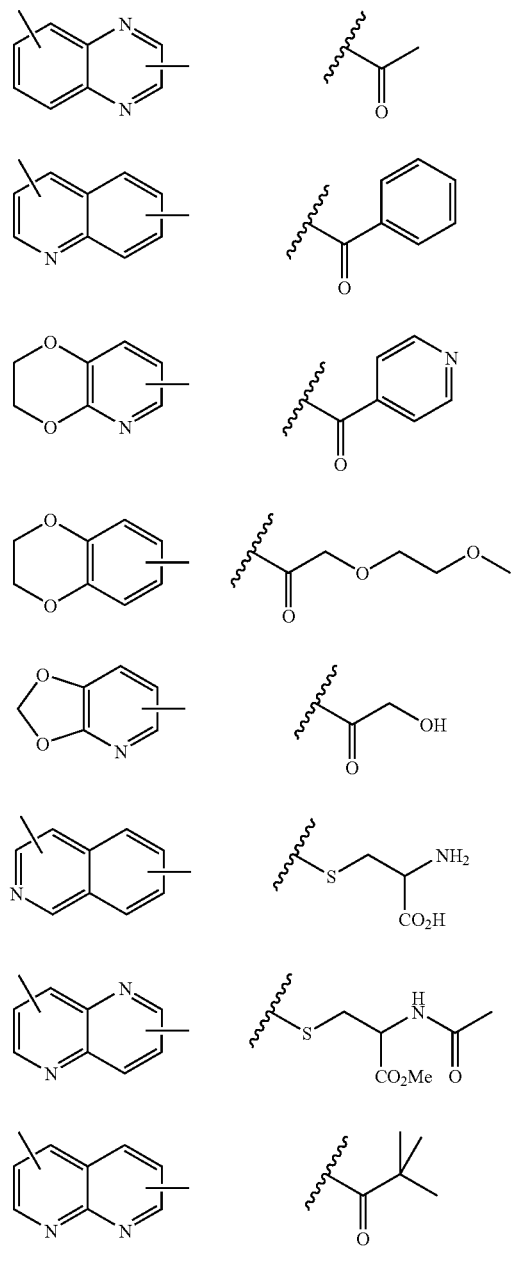
| Prophetic bicyclic tails "Q" | Prophetic pro-drug components "T" |
-continued
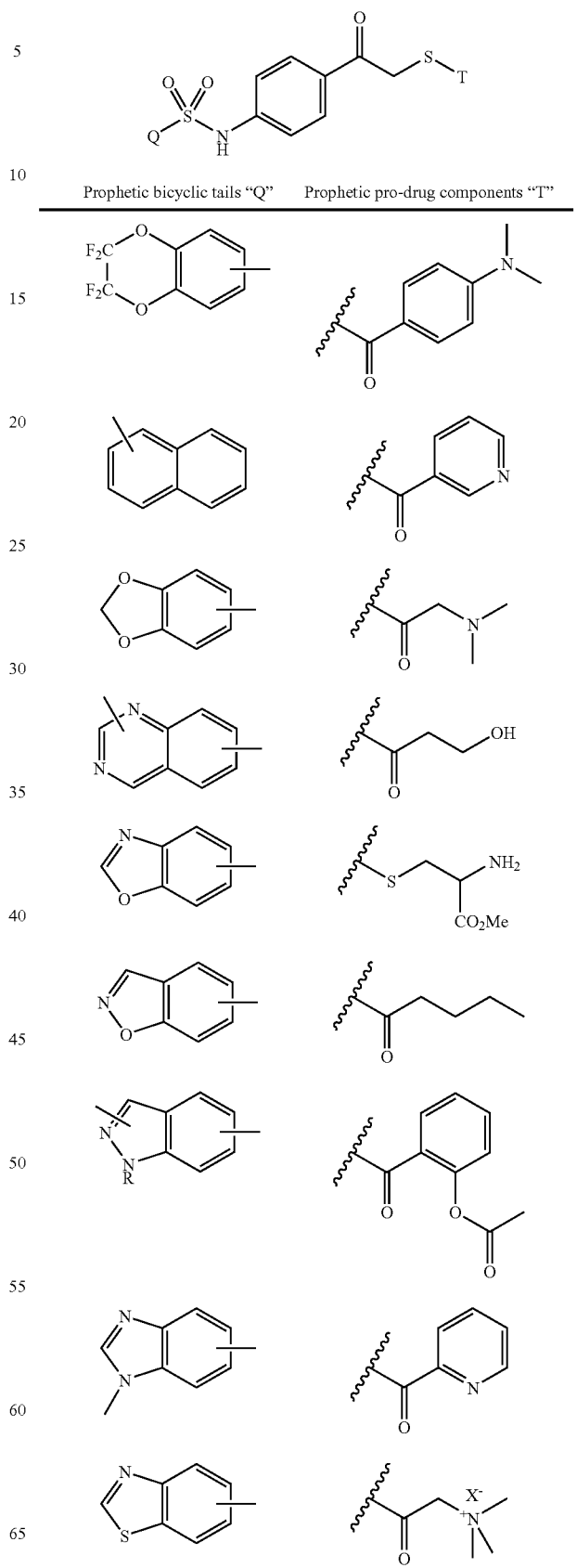
| Prophetic bicyclic tails "Q" | Prophetic pro-drug components "T" |

-continued

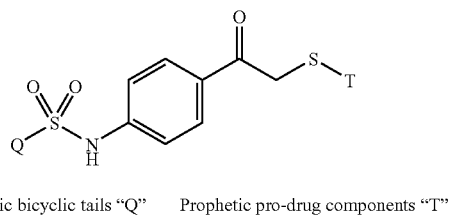

Prophetic bicyclic tails "Q"   Prophetic pro-drug components "T"

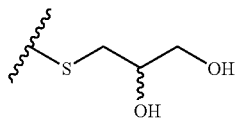

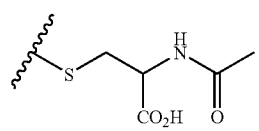

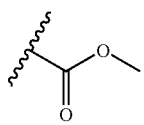

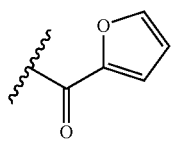

—P(O)(OH)$_2$

The above mentioned prophetic compounds can be optionally substituted as disclosed above. The connectivity of the bicyclic tails to the molecule can be to either ring.

The activity of the above mentioned compounds as HDAC inhibitors has generally been shown by the following assays. The other compounds listed above, which may not yet been made or tested, are predicted to generally have activity in these assays as well.

Inhibition Assays

In vitro HDAC-Inhibition Assay:

This assay measures a compound's ability to inhibit acetyl-lysine deacetylation in vitro and was used as both a primary screening method as well as for $IC_{50}$ determinations of confirmed inhibitors. The assay is performed in vitro using an HDAC enzyme source (e.g. partially purified nuclear extract or immunopurified HDAC complexes) and a proprietary fluorescent substrate/developer system (HDAC Quantizyme Fluor de Lys Fluorescent Activity Assay, BIOMOL). The assay is run in 1,536-well Greiner white-bottom plates using the following volumes and order of addition:

Step 1: Enzyme (2.5 ul) source added to plate (from refrigerated container)

Step 2: Compounds (50 nl) added with pin transfer device

Step 3: Fluor de Lys (2.5 ul) substrate added, incubate at RT, 30 minutes

Step 4: Developer (5 ul) solution is added (containing TSA), to stop reaction

Step 5: Plate Reader—data collection

The deacetylated fluorophore is excited with 360 nm light and the emitted light (460 nm) is detected on an automated fluorometric plate reader (Aquest, Molecular Devices).

Cellular Histone Hyperacetylation Assays:

These two secondary assays evaluates a compound's ability to inhibit HDAC in cells by measuring cellular histone acetylation levels. The cytoblot facilitates quantitative $EC_{50}$ information for cellular HDAC inhibition. Transformed cell lines (e.g. HeLa, A549, MCF-7) are cultured under standard media and culture conditions prior to plating.

For Cytoblot:

Cells (approx. 2,500/well) are allowed to adhere 10-24 hours-to wells of a 384-well Greiner PS assay plate in media containing 1-5% serum. Cells are treated with appropriate compound and specific concentrations for 0 to 24 hours. Cells are washed once with PBS (60 ul) and then fixed (95% ethanol, 5% acetic acid or 2% PFA) for 1 minute at RT (30 ul). Cells are blocked with 1% BSA for 1 hour and washed and stained with antibody (e.g. anti-Acetylated Histone H3, Upstate Biotechnology), followed by washing and incubation with an appropriate secondary antibody conjugated to HRP or fluorophore. For luminescence assays, signal is generated using Luminol substrate (Santa Cruz Biotechnology) and detected using an Aquest plate reader (Molecular Devices).

For Immunoblot:

Cells ($4 \times 10^5$/well) are plated into Corning 6-well dish and allowed to adhere overnight. Cells are treated with compound at appropriate concentration for 12-18 hours at 37 degrees. Cells are washed with PBS on ice. Cells are dislodged with rubber policeman and lysed in buffer containing 25 mM Tris, pH7.6; 150 mM NaCl, 25 mM $MgCl_2$, 1% Tween-20, and nuclei collected by centriguation (7500 g). Nuclei are washed once in 25 mM Tris, pH7.6; 10 mM EDTA, collected by centrifugation (7500 g). Supernatant is removed and histones are extracted using 0.4 M HCl. Samples are centrifuged at 14000 g and supernatants are precipitated in 1 ml cold acetone. The histone pellet is dissolved in water and histones are separated and analyzed by SDS-PAGE Coomassie and immunobloting (anti-acetylated histone antibodies, Upstate Biotechnology) using standard techniques.

Differential Cytotoxicity Assay:

HDAC inhibitors display differential cytotoxicity toward certain transformed cell lines. Cells are cultured according to standard ATCC recommended conditions that are appropriate to each cell type. Compounds were tested for their ability to kill different cell types (normal and transformed) using the ATPlite luminescence ATP detection assay system (Perkin Elmer). Assays are run in either 384-well or 1536-well Greiner PS plates. Cells (30 ul or 5 ul, respectively) are dispensed using either multichannel pipette for 384-well plates, or proprietary Kalypsys bulk liquid dispenser for 1536-well plates. Compounds added using proprietary pin-transfer device (500 nL or 5 nL) and incubated 5 to 30 hours prior to analysis. Luminescence is measured using Aquest plate reader (Molecular Devices).

The activity of some of the compounds of the invention are shown in Table 1, below.

TABLE 1

| Example No. | COMPOUND | In vitro IC$_{50}$ (μM) | Cellular IC$_{50}$ (μM) |
|---|---|---|---|
| 01 | | <1 | <10 |
| 02 | | <1 | <10 |
| 03 | | <1 | <10 |
| 04 | | <1 | <10 |
| 05 | | <1 | <1 |
| 06 | | <1 | <10 |

TABLE 1-continued
| Example No. | COMPOUND | In vitro IC$_{50}$ (µM) | Cellular IC$_{50}$ (µM) |
|---|---|---|---|
| 07 | 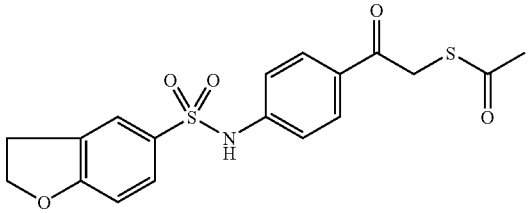 | <1 | <1 |
| 08 | 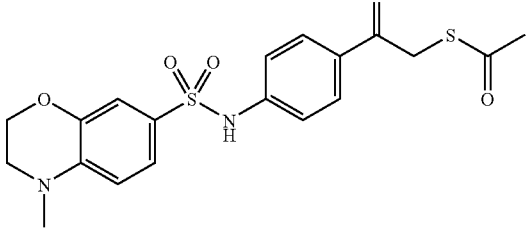 | <1 | <10 |
| 09 | 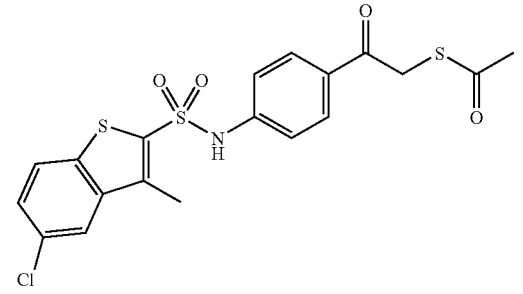 | <1 | <10 |
| 10 | 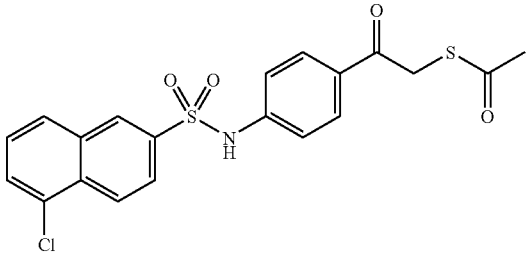 | <1 | <1 |
| 11 | 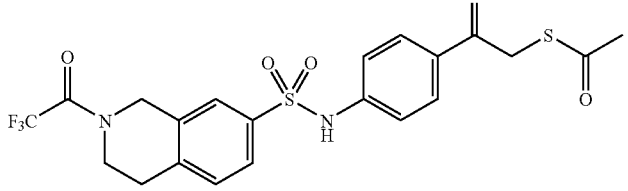 | <1 | <10 |
| 12 | 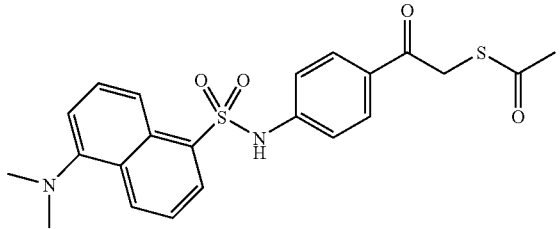 | <1 | <10 |

TABLE 1-continued

| Example No. | COMPOUND | In vitro IC$_{50}$ (μM) | Cellular IC$_{50}$ (μM) |
| --- | --- | --- | --- |
| 13 | | <1 | <10 |
| 14 | | >50 | >50 |
| 15 | | <1 | <1 |
| 17 | | <1 | <10 |
| 18 | | <1 | <10 |
| 19 | | <1 | <10 |

TABLE 1-continued

| Example No. | COMPOUND | In vitro IC$_{50}$ (μM) | Cellular IC$_{50}$ (μM) |
|---|---|---|---|
| 20 | | <1 | <10 |
| 21 | | >1 | |
| 22 | | <1 | <1 |
| 23 | | | |

In vivo Effects of HDAC Inhibitors

Evaluation of Efficacy of HDAC Inhibitors for Their Anti-Tumor Activity in vivo

A xenograft tumor assay was carried out to measure the efficacy of HDAC inhibitors as tumor inhibitors in vivo. Immunocompromised mice (female, athymic, nu/nu or SCID 4-6 weeks age; Jackson Laboratories, Bar Harbor, Me.) were housed 5 mice per cage in a specially designed containment facility to support optimum survival of immunocompromised animals. Animals had free access to sterilized food and water throughout the study and were on light-dark cycles of 12 hr duration. All animal procedures were conducted as per institutionally approved protocols. After 5-7 days of acclimation to the vivarium, mice were inoculated subcutaneously with 2-5×10$^6$ human tumor cells (HCT-116 tumor cell line) suspended in 50% matrigel over flank or bilateral inguinal regions (0.1 mL/mouse). One to two weeks after implantation, when the tumor weight reached 100-250 mg, animals were randomized to receive drug (test compound) or vehicle treatment. Each treatment group had 12-15 mice (n-12-15). Test compounds soluble in aqueous vehicles were dosed as solutions, while those with less than optimal solubility were dosed as fine suspensions in 0.5% methylcellulose with 0.05% Tween-20 either once per day or twice per day. All drugs were given by intraperitoneal injections at a volume of 10 mL/kg body weight. The control group of animals received appropriate treatments with vehicle only. Tumor length and width, and body weights were measured twice to thrice per week, and tumor weight was determined by caliper measurement and calculated according to the following formula: tumor weight (mg)=(tumor length (mm)×tumor width$^2$ (mm ))/2. In addition to tumor measurements, a daily health check was conducted. Results are shown in FIG. 1, where symbols represent mean±SEM for n=12-15 mice per treatment group.

FIG. 1 shows the effects of HDAC inhibitors Compound A (used as a comparative cstandard) (at two different doses) and Compound B (used as a comparative cstandard) on the growth of HCT-116 (human colon cancer cell line) in female athymic nude mice. After three weeks, mice treated test compounds Compound B or Compound A at 50 mg/kg showed significant reduction in tumor weight. In mice treated with vehicle alone (control), the xenograft tumor continued to increase in weight. In mice treated with Compound A at 25 mg/kg, the test compound did not significantly inhibit tumor growth. The present results demonstrate that HDAC inhibitors are capable of having anti-tumor activity in vivo, when administered in a therapeutically effective amount.

Measurement of Histone Hyperacetylation in Cells Following Treatment with HDAC Inhibitors.

Cells were exposed to 100 mM solutions of HDAC inhibitors Compound B or Compound 02, the synthesis of which is described in Example 2 above. Thirty micrograms (30 μg) of total cellular protein was separated by electrophoresis on a 4-20% gradient Tris-Glycine gel, and subsequently blotted onto a nitrocellulose membrane. Levels of acetylated H3 and H4 histones were detected as described above. Briefly, protein-containing nitrocellulose membranes were separately incubated with a 1:1000 dilution of antibodies against acetylated H3 or a 1:1000 dilution of antibodies against acetylated H4 (Anti-Acetylated Histone H3, Anti-Acetyled Histone H4, Upstate Biotechnology). After incubation with primary antibodies, the nitrocellulose membranes were washed using standard wash protocols, incubated with labelled secondary antibodies, and visualized by chemiluminescence.

Figure 2A:
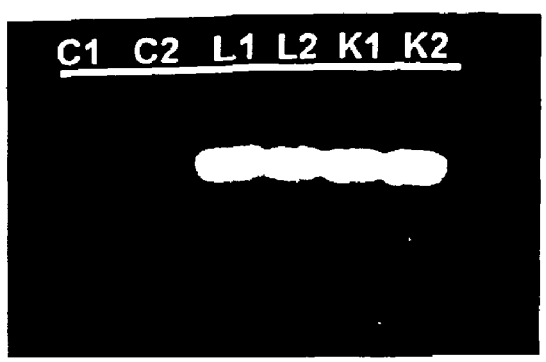
FIG. 2A shows a Western blot of 30 μg total cellular protein probed for acetylated histone H3 levels.
Figure 2B:
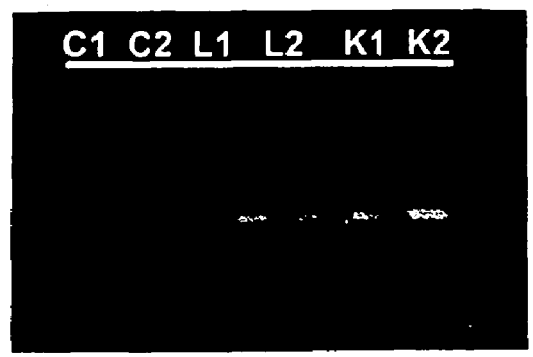
FIG. 2B shows a Western blot of 30 μg total cellular protein probed for acetylated H4 histone; lanes C1 and C2 are from control cells (no HDAC inhibitor), lanes L1 and L2 are from cells treated with 100 nM Compound B, and lanes K1 and K2 are from cells treated with 100 nM Compound 02, the synthesis of which is described in Example 2 herein.

Results for Western blot analysis of acetylated H3 histone are shown in FIG. 2A. Results for Western blot analysis of acetylated H4 histone are shown in FIG. 2B. In FIGS. 2A and 2B, lanes C1 and C2 are from control cells (no HDAC inhibitor), lanes L1 and L2 are from cells treated with 100 nM Compound B, and lanes K1 and K2 are from cells treated with 100 nM Compound 02.

Dose-Dependent in vivo Induction of Histone Hyperacetylation by HDAC Inhibitors.

Mice were treated with various doses of HDAC inhibitor Compound 02 (the synthesis of which is described in Example 2, above), and the degree of H3 histone acetylation in peripheral blood mononuclear cells (PMN)was determined by Western blot analysis.

Briefly, CD-1 mice were administered a suspension of Compound 02 in 0.5% methylcellulose with 0.05% Tween-2 at a dose of 25 mg/kg/day, 50 mg/kg/day or 100 mg/kg/day, for 5 days. Three (3) mice were used for each dose group. Blood was drawn from each mouse 3-4 hrs after the last dose. Red blood cells were lysed and the remaining peripheral blood mononuclear cells (PMNs) were collected by centrifugation. The collected PMNs were lysed and 30 μg of total cell protein (PMN lysate) was separated by electrophoresis on a 4-20% gradient Tris-Glycine gel, and subsequently blotted onto a nitrocellulose membrane. Protein-containing nitrocellulose membranes were separately incubated with a 1:1000 dilution of antibodies against acetylated H3 (Anti-Acetylated Histone H3, Upstate Biotechnology). After incubation with primary antibodies, the nitrocellulose membranes were washed using standard wash protocols, incubated with labelled secondary antibodies, and visualized by chemiluminescence.

Figure 3:
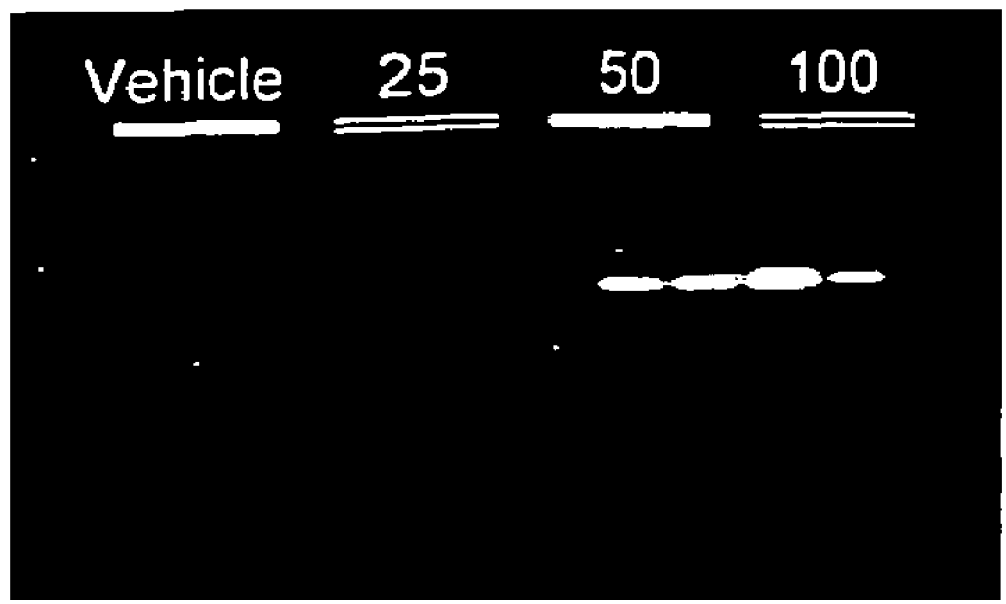
FIG. 3 shows dose-dependent induction of histone hyperacetylation in mouse epripheral blood mononuclear cells following administration of varying doses of HDAC inhibitor Compound 02.

Results for Western blot analysis of histone H3 acetylation is shown in FIG. 3. Lanes marked "Vehicle" correspond to PMN lysates from mice treated with vehicle only (control). Lanes marked "25" correspond to PMN lysates from mice treated with 25 mg/kg/day of Compound 02. Lanes marked "50" correspond to PMN lysates from mice treated with 50 mg/kg/day of Compound 02. Lanes marked "100" correspond to PMN lysates from mice treated with 25 mg/kg/day of Compound 02.

As shown in FIG. 3, PMNs from control mice, and from mice treated with 25 mg/kg/day of Compound 02 do not show detectable histone H3 acetylation. In contrast, histone H3 hyperacetylation is seen in PMNs from mice treated with 50 mg/kg/day or 100 mg/kg/day of Compound 02. These results indicate that the HDAC inhibitor Compound 02 is capable of inducing histone hyperacetylation in vivo in a dose-dependent manner.

Surrogate Marker for HDAC Activity in Rat Peripheral Blood Mononuclear Cells (PMN) Following Intravenous Infusion of HDAC Inhibitors The following HDAC inhibitors were used as test compounds to monitor plasma drug levels and a surrogate marker for HDAC activity: Compound 02 (the synthesis of which is described in Example 2 above); Compound 08 (the synthesis of which is described in Example 8, above), Compound A, and Compound C (used as a comparative standard). Test compounds were first dissolved in DMSO and diluted into 5-20% w/v hydroxypropylcyclodextrin in water with gentle warming and/or sonication. Male rats were infused intravenously with test compounds at varying doses (mg/kg) for approximately 2 hours. Blood samples (~1 mL) were withdrawn into a anticoagulant mixture, and an aliquot was collected into tubes containing lithium heparin anticoagulant and approximately 2.5 mg of sodium fluoride esterase inhibitor. Blood samples were centrifuged at 4° C. for 4 minutes at 14,7000×g and plasma samples were stored at −70 C until analysis.

Drug levels in plasma were quantified using HPLC/MS/MS. A 10-50 μL aliquot was drawn from each sample, and protein was precipitated using 200 μL acetonitrile and centrifugation. A standard curve and blanks (samples from untreated rats) were prepared using a 50 μL of Compound 296732 at 200 ng/mL as the stock internal standard solution. Following centrifugation, the supernatant was analyzed in multiple reaction monitoring (MRM) mode with negative ionization on AB/MDS Sciex API4000 triple quadrupole mass spectrometer using a 2 minute HPLC gradient (acetonitrile /water/0.1% formic acid) on a Synergi Polar-RP column (Phenomenex, Torrance, Calif.) An esterase inhibitor (2.5 mg of sodium fluoride per mL of plasma) was used in the standard curve.

Figure 4:
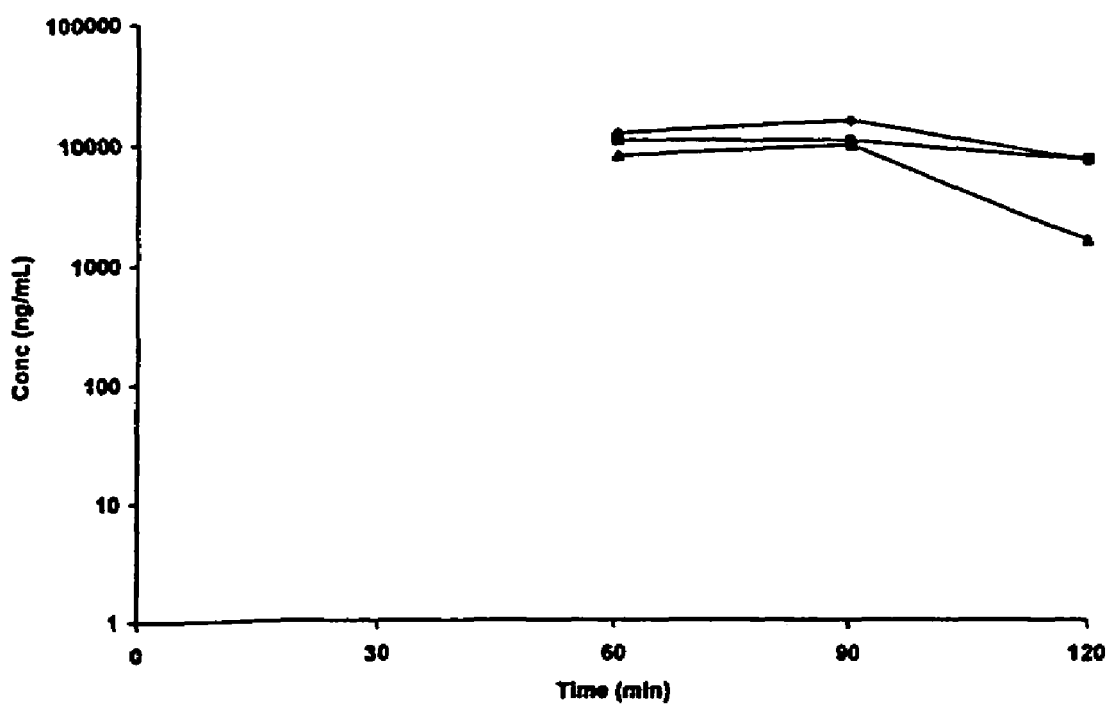
FIG. 4 shows plasma concentrations of Compound A in rates during and following a 2-hour intravenous infusion of Compound A at 7.4 mg/kg.

FIG. 4 shows the plasma concentrations of Compound A during and following a 2-hr infusion with Compound A at a dose of 7.4 mg/kg. Table 2 shows the plasma concentrations of various test compounds at times up to one hour after a 2-hr infusion with each test compound at the specified dose. Table 2 also shows measurements of a surrogate marker for PMN-associated HDAC activity levels at times up to one hour after a 2-hr infusion with each test compound at the specified dose.

TABLE 2

Parent drug levels and PMN-associated HDAC activity following 2 hr continuous IV dose

| Compound | Dose (mg/kg) | Parent Drug Levels (ng/mL) post-2 hr infusion | | | Surrogate Marker Inhibition (% Vehicle) | | |
|---|---|---|---|---|---|---|---|
| | | T1 0 min | T2 30 min | T3 60 min | T1 0 min | T2 30 min | T3 60 min |
| Compound 02 | 4.0 | 350 | 16 | 14 | 79 | 43 | 30 |
| Compound 08 | 4.1 | 662 | 406 | 418 | 61 | 60 | 38 |
| Compound A | 10.1 | N.T. | N.T. | N.T. | 92 | — | 31* |
| Compound C | 8.4 | N.T. | N.T. | N.T. | 88 | — | 56 |

*(time point @ 90 min)

Detection of Plasma Concentrations of Free Thiol and Test Compound Following Administration of Compound A Compound A was administered intraperitoneally to a group of 3 rats at a dose of 50 mg/kg, as a suspension in 0.5% methocellulose. Blood samples were collected into heparin-containing tubes on ice and then centrifuged at 4° C. for 4 minutes 14,7000×g to separate blood cells and plasma. Plasma samples were stored at −70 C until analysis.

Aliqutots of plasma samples (0.1 mL) were spiked with internal standards (50 ng/mL) and processed through solid phase extraction using Varian $C_{18}$ columns or Varian ENV (divinylbenzene co-polymer) columns for sample clean-up. Columns were eluted with methanol, and eluates were concentrated under a nitrogen stream. The dried samples were reconstituted with 100 μl of acetonitrile:water (50:50) containing 0.125 mg/mL of (+/−)-DL-dithiothreitol (DTT).

Figure 5A:
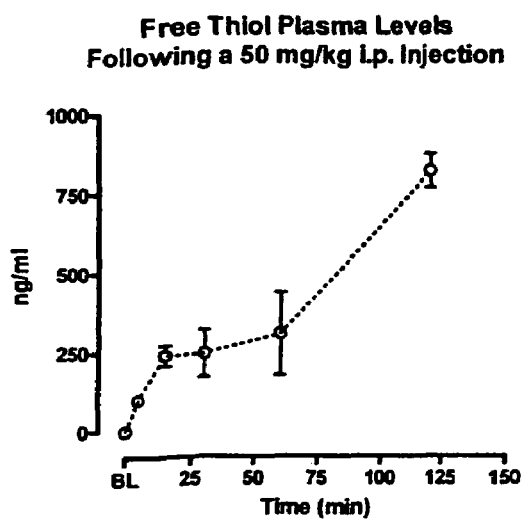
FIG. 5A shows levels of free thiol in plasma at various time points after intraperitoneal injection of 50 mg/kg of Compound A.
Figure 5B:
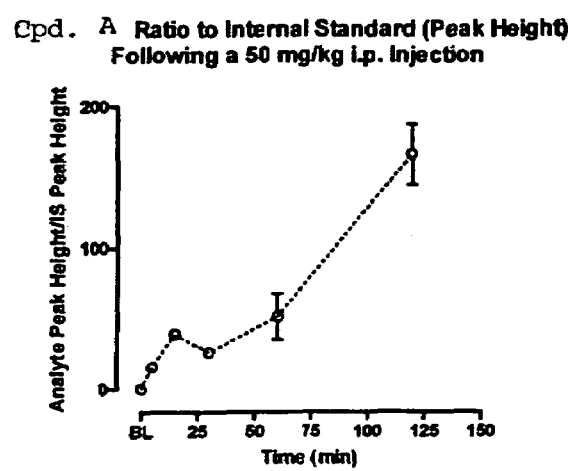
FIG. 5B shows the ratio of the levels of Compound A to the levels of internal standard, measured at various time points after intraperitoneal injection of 50 mg/kg of Compound A; symbols represent mean±SEM for three rats (n=3).

FIG. 5A shows levels of free thiol in plasma at various time points after intraperitoneal injection of 50 mg/kg of Compound A. FIG. 5B shows the ratio of the levels of Compound A to the levels of internal standard, measured at various time points after intraperitoneal injection of 50 mg/kg of Compound A. In the figures, symbols represent mean±SEM for three rats (n=3).

Compounds A and B refer to, respectively, the following structures:

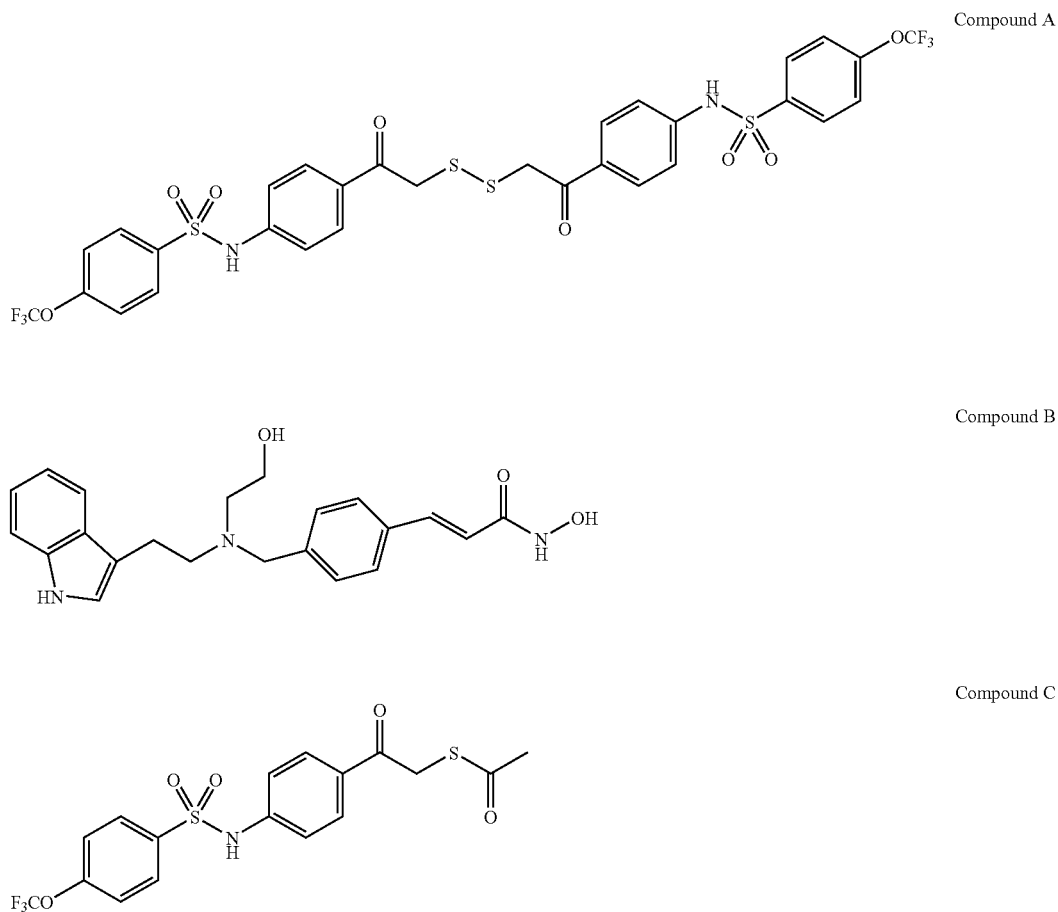

All references cited above are incorporated herein by reference in their entirety.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound having structural formula I,

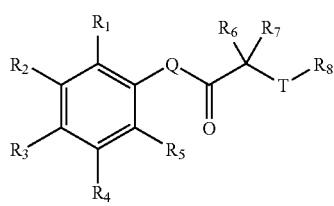

or a pharmaceutically acceptable salt, amide, ester, or prodrug thereof, wherein:
a) $R_8$ is selected from the group consisting of
  i) hydrogen; and
  vi) optionally substituted acyl of the formula —C(O)$R_E$, wherein $R_E$ is defined such that the compound having structural formula I may be hydrolyzed to yield a pharmaceutically acceptable acid HOC(O)$R_E$;
b) T is sulfur;
c) $R_6$ and $R_7$ are each independently selected from the group consisting of hydrogen and lower alkyl; or $R_6$ and $R_7$ taken together form an optionally substituted cycloalkyl;
d) Q is selected from the group consisting of a bond, —(CH$_2$)$_m$—, —(CH$_2$)$_n$NH—, —(CH$_2$)$_m$(CO)—, —(CH$_2$)$_m$NH(CO)—, and —(CH$_2$)$_m$C(O)NH—, wherein m is 0-2 and n is 1-2, wherein if Q is not symmetric, Q may be attached in either order;
e) $R_1$, $R_2$, $R_4$, and $R_5$ are each independently selected from the group consisting of
  i) hydrogen;
  ii) optionally substituted lower alkyl;
  iii) optionally substituted aryl, alkaryl, or cycloalkyl;
  iv) halogen or perhaloalkyl;
  v) an alkoxy of formula —(X$_1$)$_{n1}$—O—X$_2$, where
    $X_1$ is selected from the group consisting of lower alkylene, lower alkenylene, lower alkynylene, and aryl;
    $X_2$ is selected from the group consisting of hydrogen, optionally substituted lower alkyl, lower perfluoroalkyl, optionally substituted aryl, and optionally substituted cycloalkyl; and
    n1 is 0, 1, 2 or 3;
  vi) an acyl of formula —(X$_3$)$_{n1}$—C(O)—X$_4$, where
    $X_3$ is selected from the group consisting of lower alkylene, lower alkenylene, lower alkynylene, and aryl;
    $X_4$ is selected from the group consisting of optionally substituted lower alkyl, optionally substituted aryl, perfluoroalkyl, hydroxy, optionally substituted alkoxy, amino, and —NH—$X_5$,
    where $X_5$ is selected from the group consisting of hydrogen, optionally substituted alkyl, and optionally substituted aryl; and
    n1 is 0, 1, 2, or 3;
  vii) cyano;
  viii) an amino of formula —(X$_{15}$)$_{n15}$—NX$_{16}$X$_{17}$, where
    $X_{15}$ is selected from the group consisting of lower alkylene, lower alkenylene, lower alkynylene, and aryl;
    $X_{16}$ and $X_{17}$ are each independently selected from the group consisting of hydrogen, optionally substituted lower alkyl, optionally substituted aryl, and —C(O)$X_6$,
      where $X_6$ is selected from the group consisting of hydrogen, optionally substituted alkyl, and optionally substituted aryl; and
    $n_{15}$ is 0 or 1;
  x) a thioether or thiol of formula —(X$_{22}$)$_{n22}$—S—X$_{23}$, where
    $X_{22}$ is selected from the group consisting of lower alkylene, lower alkenylene, lower alkynylene, and aryl;
    $X_{23}$ is selected from the group consisting of hydrogen, optionally substituted lower alkyl, perflouralkyl, and optionally substituted aryl; and
    n22 is 0, 1, 2, or 3;
  xi)
(f) $R_3$ is selected from the group consisting of
  (i) an N-sulfonamido of structure

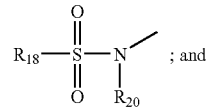
; and ii) an S-sulfonamide of formula

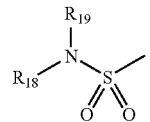

g) $R_{18}$ is $G_1$-$G_2$-,
  $G_2$ is selected from the group consisting of a bond and optionally substituted lower alkylene; and
  $G_1$ comprises at least two rings and is selected from the group consisting of optionally substituted fused polycyclic aryl, optionally substituted fused polycyclic aryl and cycloalkyl, optionally substituted fused polycyclic aryl and heterocycloalkyl, optionally substituted linked bi-aryl, optionally substituted linked aryl-heteroaryl, and optionally substituted linked aryl-heterocycloalkyl;
h) $R_{19}$ is selected from the group consisting of hydrogen, optionally substituted lower alkyl, and optionally substituted aralkyl; and
(i) $R_{20}$ is selected from the group consisting of hydrogen, optionally substituted lower alkyl, and optionally substituted lower aralkyl.

2. The compound of claim 1, wherein Q is a bond.

3. The compound of claim 2 wherein R6 and R7 are both hydrogen or are both methyl.

4. The compound of claim 3 wherein $R_1$, $R_2$, $R_4$, and $R_5$ are hydrogen.

5. The compound of claim 4 wherein G2 is selected from the group consisting of a bond, methylene, and ethylene.

6. The compound of claim 2 wherein G1 is an optionally substituted fused polycyclic aryl.

7. The compound of claim 6 wherein G1 is napththyl.

8. The compound of claim 7 wherein G1 is optionally singly or multiply substituted with substituents independently chosen from the group consisting of hydrogen, perhaloaryloxy, alkanoylalkyl, N-aryl-N-alkylamino, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamide, N-arylcarboxamidoalkoxy, cycloalkylcarbonyl, cyanoalkoxy, carboxy, cycloalkylamino, acylalkyl, acylalkoxy, aroylalkoxy, aralkylaryl, aralkyl, aralkenyl, aralkynyl, haloalkylthio, alkanoyloxy, alkoxy, alkoxyalkyl, cycloalkoxy, cycloalkylalkoxy, hydroxyl, amino, thio, nitro, alkylamino, alkylthio, arylamino, aralkylamino, arylthio, arylthioalkyl, alkylsulfonyl, arylsulphonyl alkanoyl, alkenoyl, aroyl, aralkanoyl, haloalkanoyl, alkyl, alkenyl, alkynyl, alkenyloxy, alkylenedioxy, haloalkylenedioxy, cycloalkyl, cycloalkylalkanoyl, halo, haloalkyl, haloalkoxy, hydroxyhaloalkyl, hydroxyhaloalkoxy, hydroxyalkyl, aryl, aryloxy, aralkoxy, arylalkenyl, carboalkoxy, alkoxycarboxamido, alkylamidocarboylamido, arylamidocarboylamido, carboalkoxyalkyl, carboalkoxyalkenyl, carboamido, carboxamidoalkyl, cyanocycloalkylalkyl, cycloalkenyl, alkoxycarbonyl, aralkylthio, alkylthio, alkylsulfinyl, arylsulfinyl, dialkylamino, aminoalkyl, dialkylaminoalkyl, aminoaryl, alkylaminoaryl, acylamino, aminocarbonylalkoxy, aminocarbonylamino, aminothiocarbonylamino, and aminothiocarbonylaminoalkyl.

9. The compound of claim 8 wherein Q is a bond.

10. The compound of claim 9 wherein $R_1$, $R_2$, $R_4$, and $R_5$ are hydrogen.

11. The compound of claim 10 wherein G2 is a bond, methylene, or ethylene.

12. The compound according to claim 11 wherein the compound has a structure selected from a group consisting of:

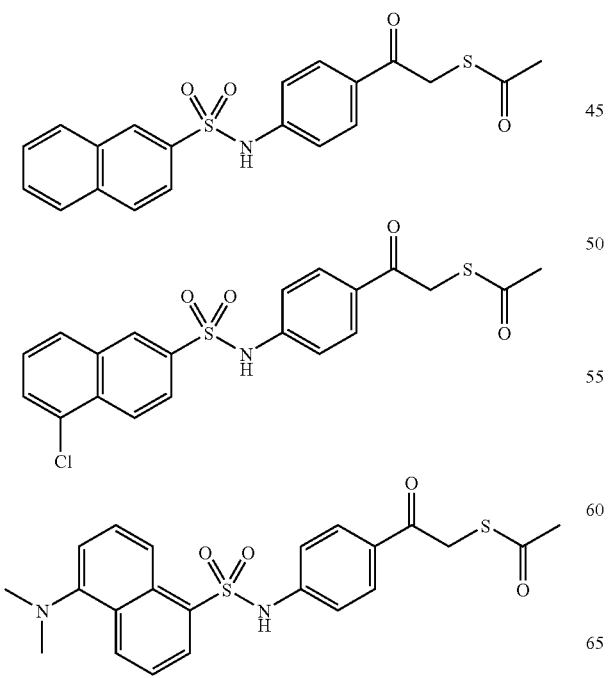

-continued

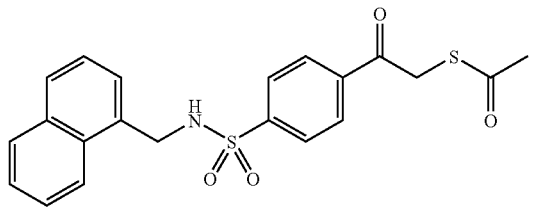

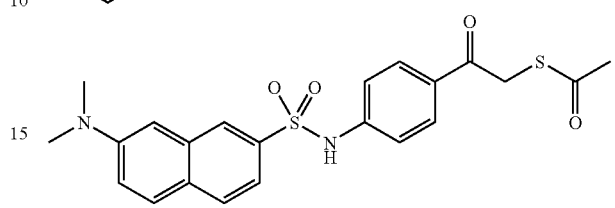

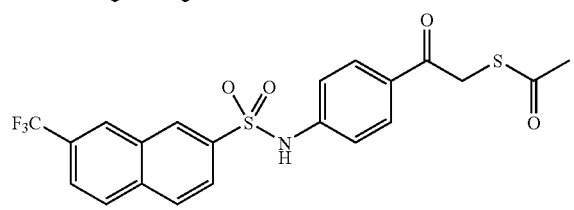

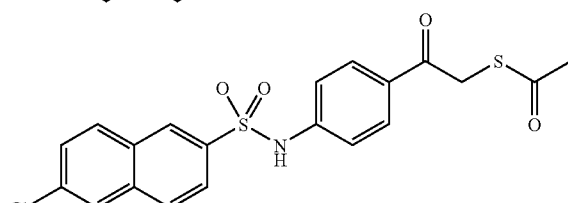

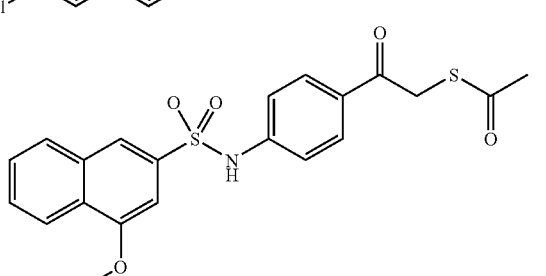

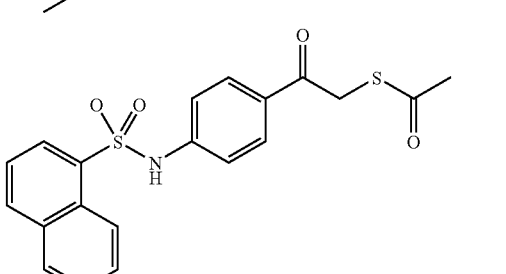

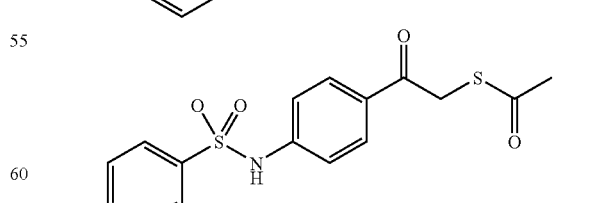

-continued
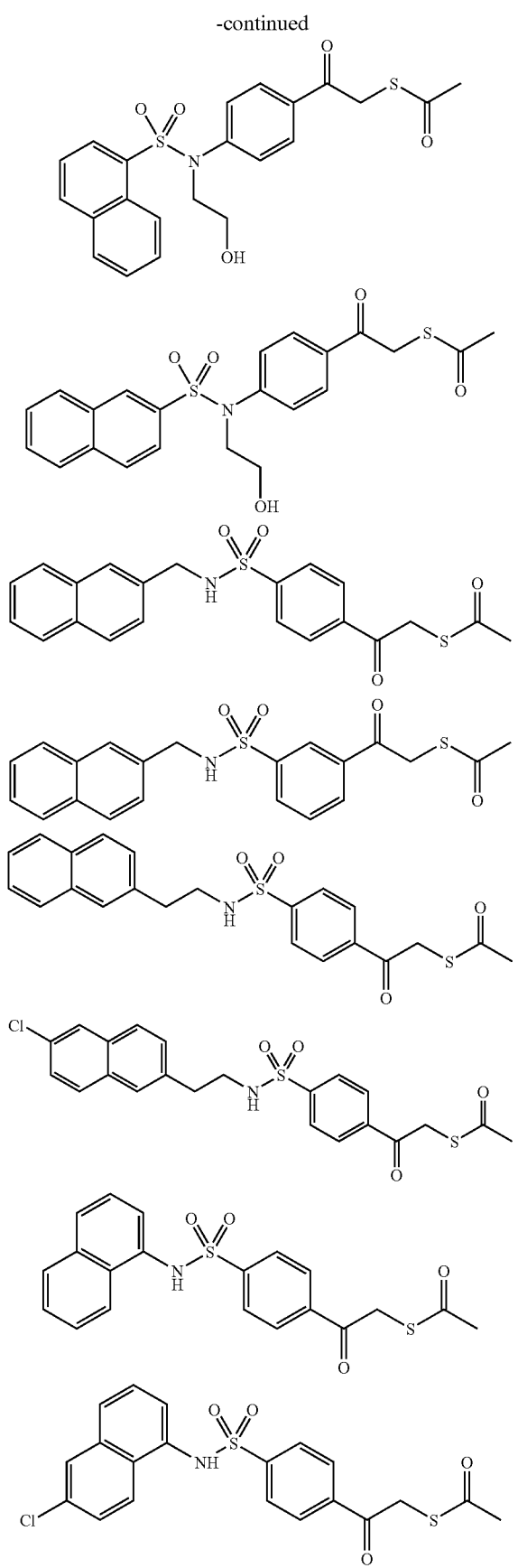
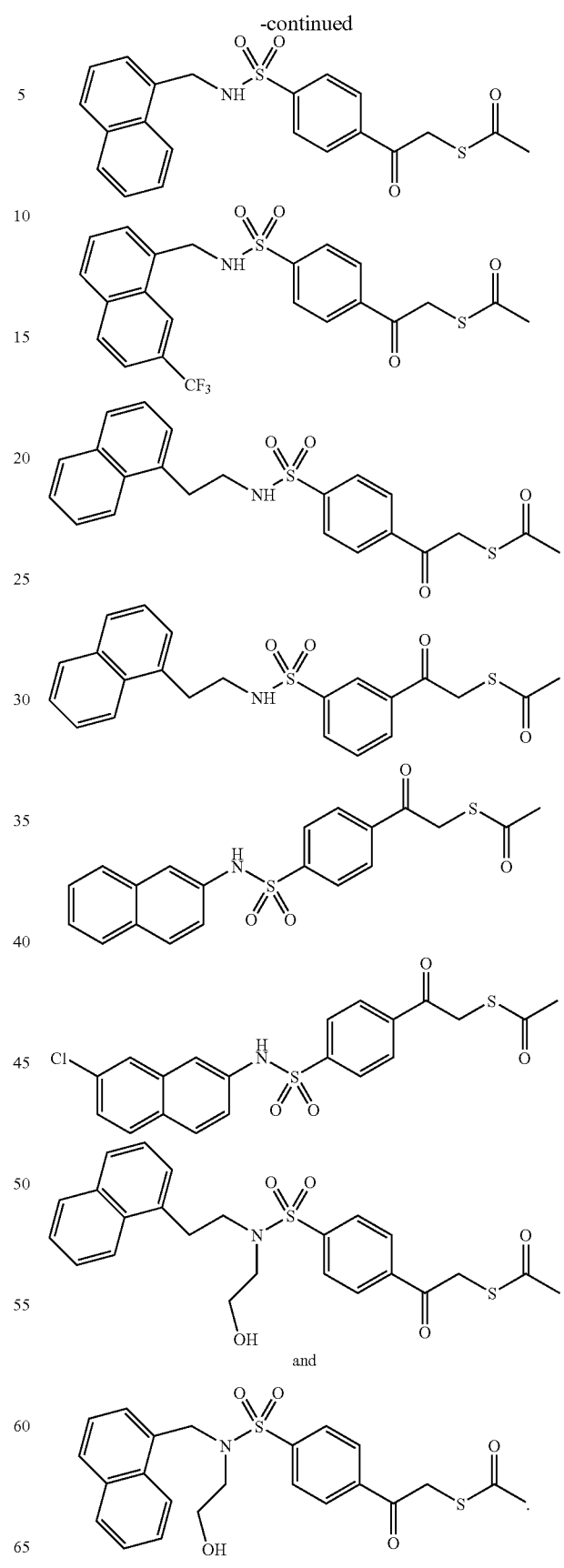

13. The compound of claim 1 wherein G1 is an optionally substituted fused mono- or polycyclic aryl and cycloalkyl ring.

14. The compound of claim 13 wherein G1 is selected from a group consisting of:

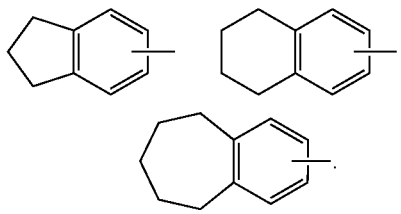

and

15. The compound of claim 14 wherein G1 is optionally singly or multiply substituted with substituents independently chosen from the group consisting of hydrogen, perhaloaryloxy, alkanoylalkyl, N-aryl-N-alkylamino, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamide, N-arylcarboxamidoalkoxy, cycloalkylcarbonyl, cyanoalkoxy, carboxy, cycloalkylamino, acylalkyl, acylalkoxy, aroylalkoxy, aralkylaryl, aralkyl, aralkenyl, aralkynyl, haloalkylthio, alkanoyloxy, alkoxy, alkoxyalkyl, cycloalkoxy, cycloalkylalkoxy, hydroxyl, amino, thio, nitro, alkylamino, alkylthio, arylamino, aralkylamino, arylthio, arylthioalkyl, alkylsulfonyl, arylsulphonyl, alkanoyl, alkenoyl, aroyl, aralkanoyl, haloalkanoyl, alkyl, alkenyl, alkynyl, alkenyloxy, alkylenedioxy, haloalkylenedioxy, cycloalkyl, cycloalkylalkanoyl, halo, haloalkyl, haloalkoxy, hydroxyhaloalkyl, hydroxyhaloalkoxy, hydroxyalkyl, aryl, aryloxy, aralkoxy, arylalkenyl, carboalkoxy, alkoxycarboxamido, alkylamidocarboylamido, arylamidocarboylamido, carboalkoxyalkyl, carboalkoxyalkenyl, carboamido, carboxamidoalkyl, cyanocycloalkylalkyl, cycloalkenyl, alkoxycarbonyl, aralkylthio, alkylthio, alkylsulfinyl, arylsulfinyl, dialkylamino, aminoalkyl, dialkylaminoalkyl, aminoaryl, alkylaminoaryl, acylamino, aminocarbonylalkoxy, aminocarbonylamino, aminothiocarbonylamino, and aminothiocarbonylaminoalkyl.

16. The compound of claim 15 wherein Q is a bond.

17. The compound of claim 16 wherein $R_1$, $R_2$ $R_4$, and $R_5$ are hydrogen.

18. The compound of claim 17 wherein G2 is a bond, methylene, or ethylene.

19. The compound according to claim 18 wherein the compound has the structure selected from the group consisting of:

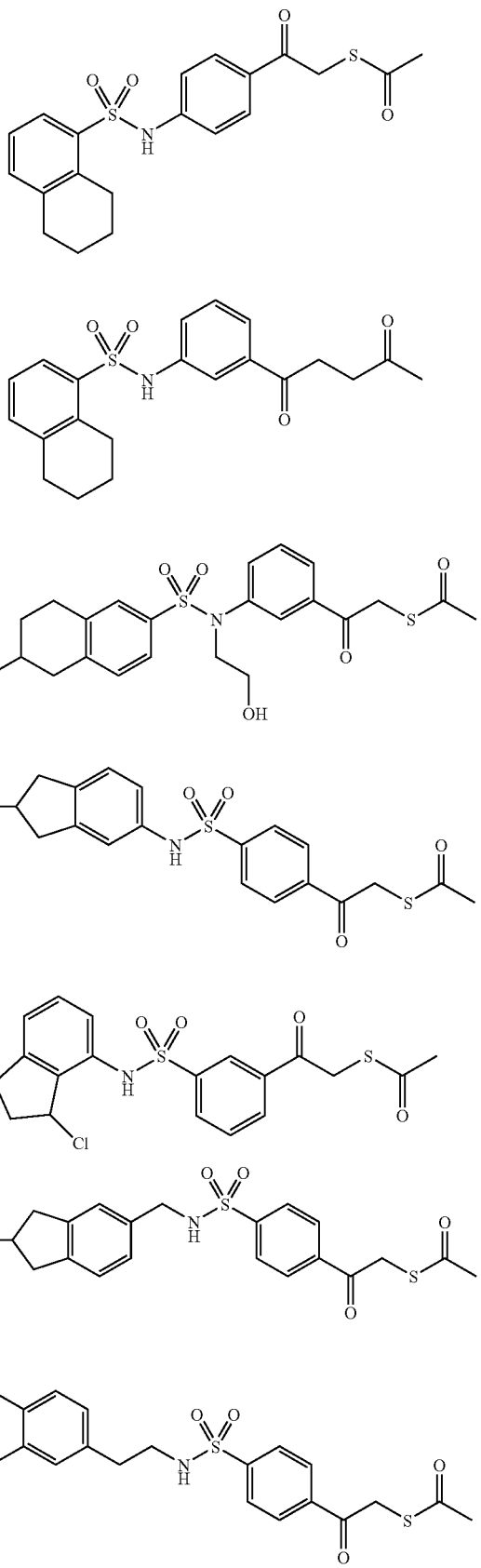

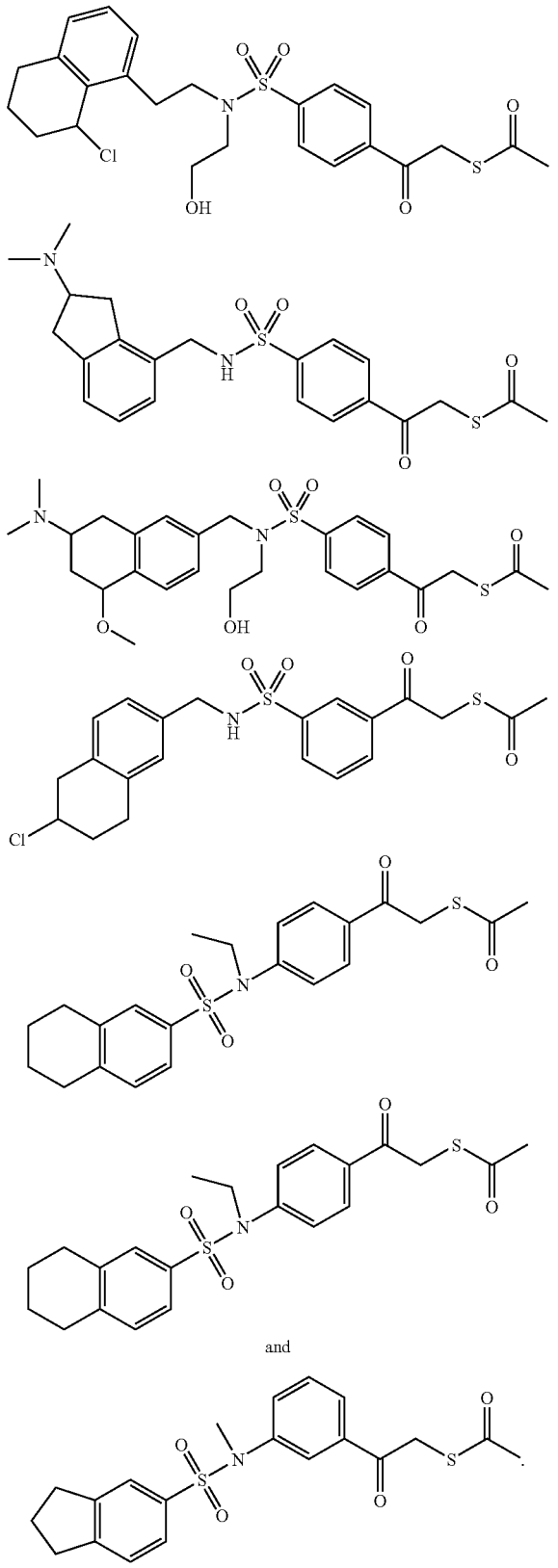

20. The compound of claim 2 wherein G1 is an optionally substituted fused aryl and heterocycloalkyl.

21. The compound of claim 20 wherein G1 is selected from a group consisting of:

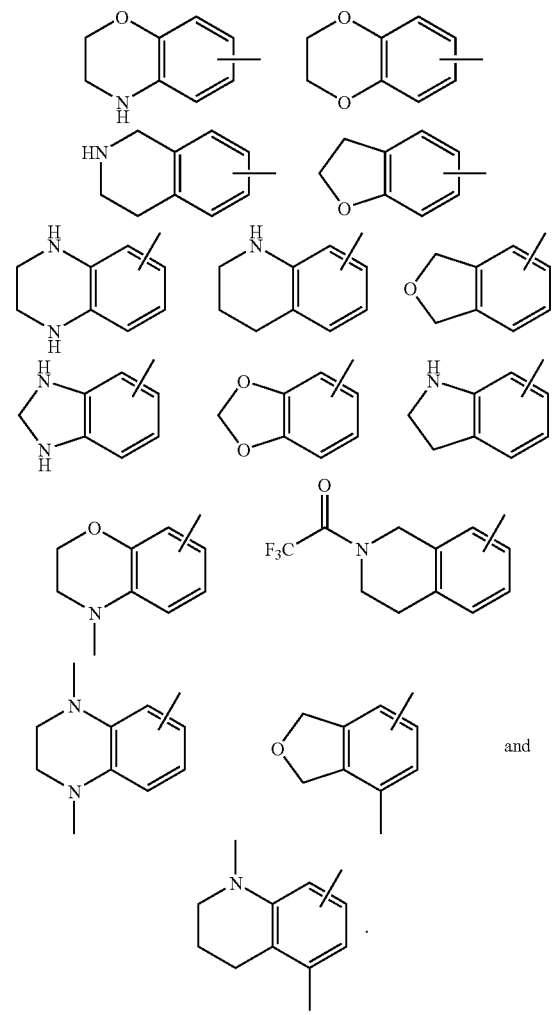

22. The compound of claim 21 wherein G1 is optionally singly or multiply substituted with substituents independently chosen from the group consisting of hydrogen, perhaloaryloxy, alkanoylalkyl, N-aryl-N-alkylamino, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamide, N-arylcarboxamidoalkoxy, cycloalkylcarbonyl, cyanoalkoxy, carboxy, cycloalkylamino, acylalkyl, acylalkoxy, aroylalkoxy, aralkylaryl, aralkyl, aralkenyl, aralkynyl, haloalkylthio, alkanoyloxy, alkoxy, alkoxyalkyl, cycloalkoxy, cycloalkylalkoxy, hydroxyl, amino, thio, nitro, alkylamino, alkylthio, arylamino, aralkylamino, arylthio, arylthioalkyl, alkylsulfonyl, arylsulphonyl, alkanoyl, alkenoyl, aroyl, aralkanoyl, haloalkanoyl, alkyl, alkenyl, alkynyl, alkenyloxy, alkylenedioxy, haloalkylenedioxy, cycloalkyl, cycloalkylalkanoyl, halo, haloalkyl, haloalkoxy, hydroxyhaloalkyl, hydroxyhaloalkoxy, hydroxyalkyl, aryl, aryloxy, aralkoxy, arylalkenyl, carboalkoxy, alkoxycarboxamido, alkylamidocarboylamido, arylamidocarboylamido, carboalkoxyalkyl, carboalkoxyalkenyl, carboamido, carboxamidoalkyl, cyanocycloalkylalkyl, cycloalkenyl, alkoxycarbonyl, aralkylthio, alkylthio, alkylsulfinyl, arylsulfinyl, dialkylamino, aminoalkyl, , dialkylaminoalkyl, aminoaryl, alkylaminoaryl, acylamino, aminocarbonylalkoxy, aminocarbonylamino, aminothiocarbonylamino, and aminothiocarbonylaminoalkyl.

23. The compound of claim 22 wherein Q is a bond.

24. The compound of claim 23 wherein $R_1$, $R_2$, $R_4$, and $R_5$ are hydrogen.

25. The compound according to claim 24 wherein the compound has the structure selected from a group consisting of:

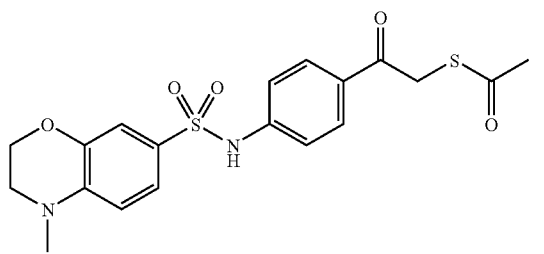

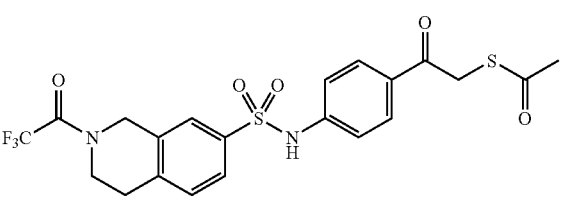

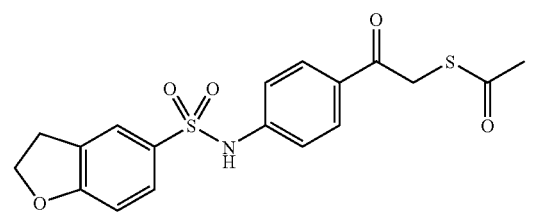

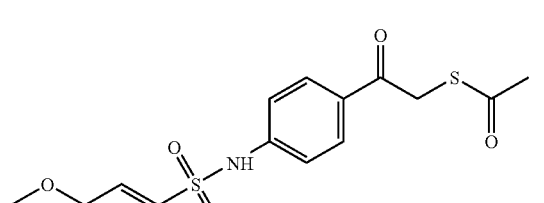

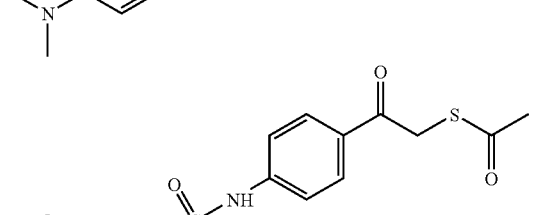

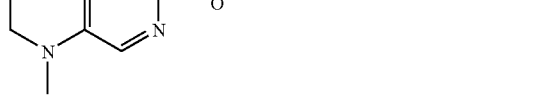

-continued

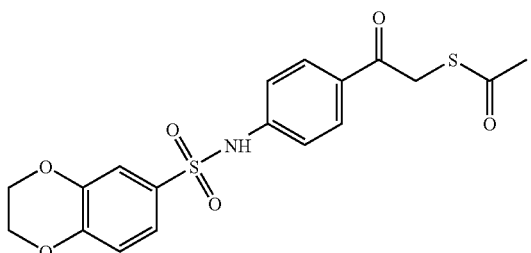

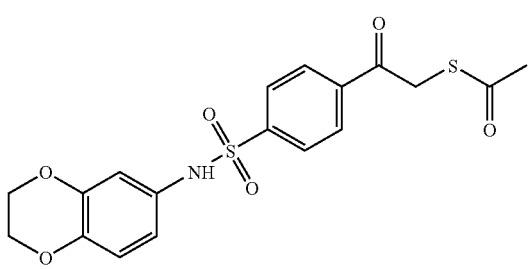

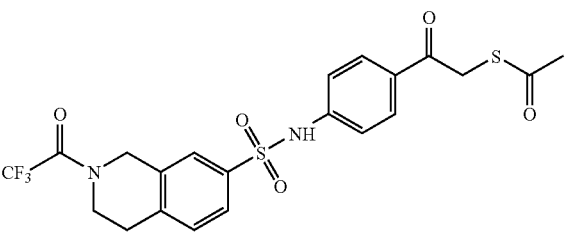

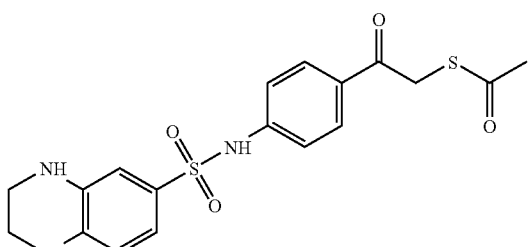

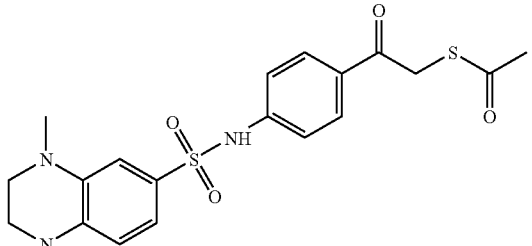

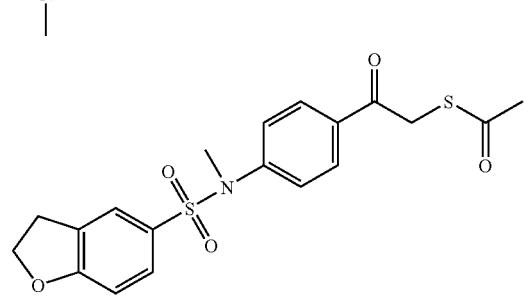

-continued

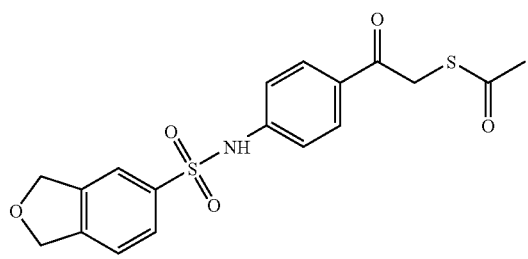

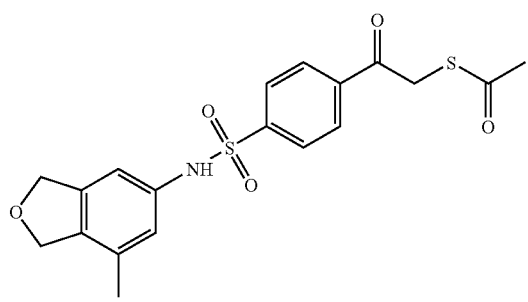

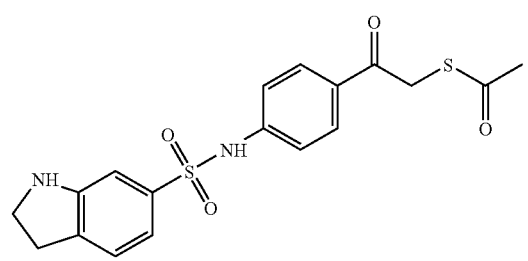

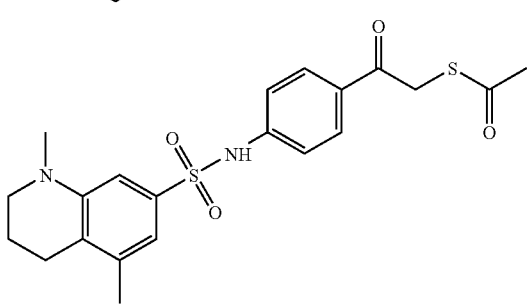

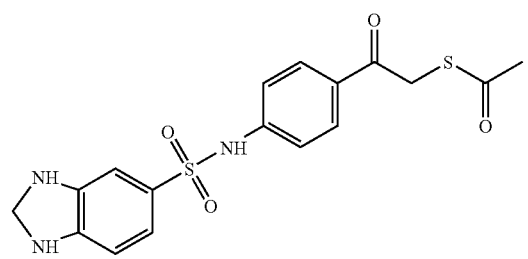

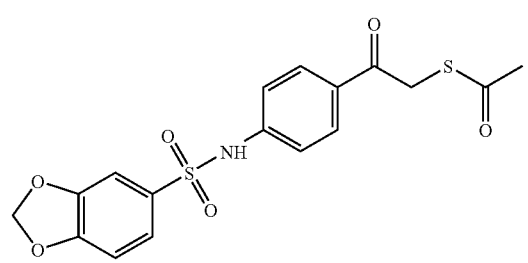

-continued

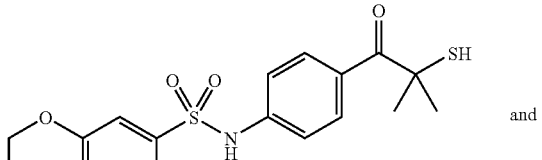

and

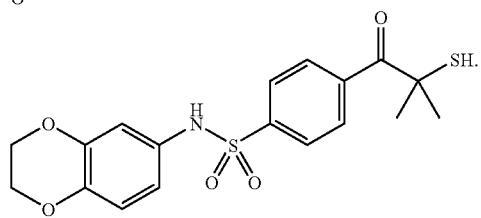

26. The compound according to claim 25 wherein the compound has the structure selected from a group consisting of:

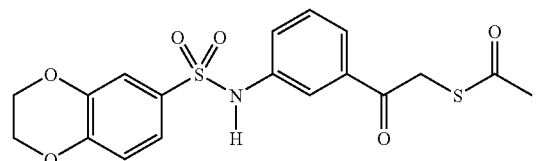

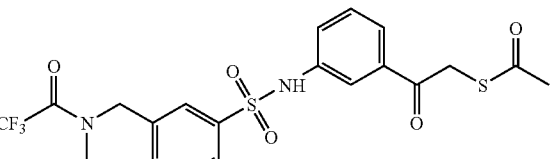

and

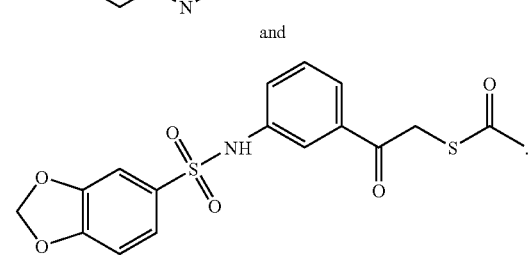

27. The compound of claim 1 wherein G1 is an optionally substituted linked biaryl.

28. The compound of claim 27 wherein G1 is

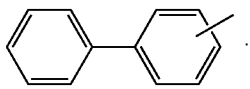

29. The compound of claim 28 wherein G1 is optionally singly or multiply substituted with substituents independently chosen from the group consisting of hydrogen, perhaloaryloxy, alkanoylalkyl, N-aryl-N-alkylamino, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamide, N-arylcarboxamidoalkoxy, cycloalkylcarbonyl, cyanoalkoxy, carboxy, cycloalkylamino, acylalkyl, acylalkoxy, aroylalkoxy, aralkylaryl, aralkyl, aralkenyl, aralkynyl, haloalkylthio, alkanoyloxy, alkoxy, alkoxyalkyl, cycloalkoxy, cycloalkylalkoxy, hydroxyl, amino, thio, nitro, alkylamino, alkylthio, arylamino, aralkylamino, arylthio, arylthioalkyl, alkylsulfonyl, arylsulphonyl, alkanoyl, alkenoyl, aroyl, aralkanoyl, haloalkanoyl, alkyl, alkenyl, alkynyl, alkenyloxy, alkylenedioxy, haloalkylenedioxy, cycloalkyl, cycloalkylalkanoyl, halo, haloalkyl, haloalkoxy, hydroxyhaloalkyl, hydroxyhaloalkoxy, hydroxyalkyl, aryl, aryloxy, aralkoxy, arylalkenyl, carboalkoxy, alkoxycarboxamido, alkylamidocarboylamido, arylamidocarboylamido, carboalkoxyalkyl, carboalkoxyalkenyl, carboamido, carboxamidoalkyl, cyanocycloalkylalkyl, cycloalkenyl, alkoxycarbonyl, aralkylthio, alkylthio, alkylsulfinyl, arylsulfinyl, dialkylamino, aminoalkyl, , dialkylaminoalkyl, aminoaryl, alkylaminoaryl, acylamino, aminocarbonylalkoxy, aminocarbonylamino, aminothiocarbonylamino, and aminothiocarbonylaminoalkyl.

30. The compound of claim 29 wherein Q is a bond.
31. The compound of claim 30 wherein $R_1$, $R_2$, $R_4$, and $R_5$ are hydrogen.
32. The compound of claim 31 wherein G2 is a bond, methylene, or ethylene.
33. The compound according to claim 32 wherein the compound has the structure selected from a group consisting of:

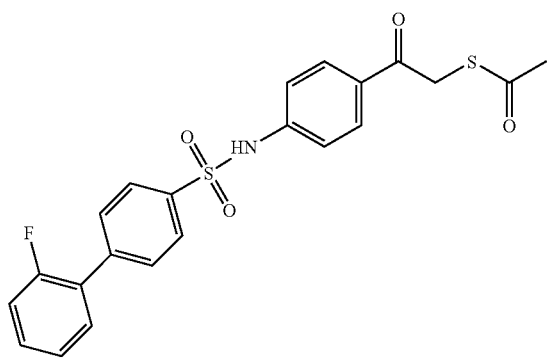

-continued

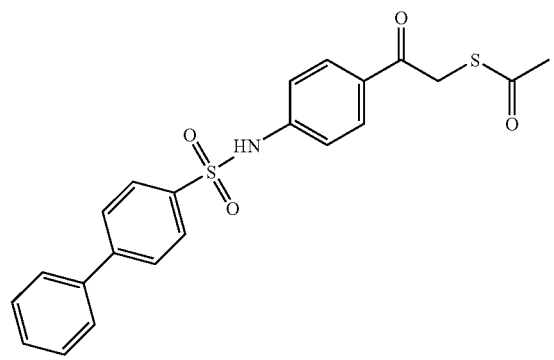

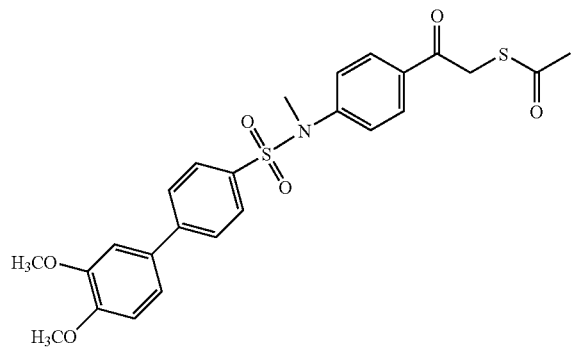

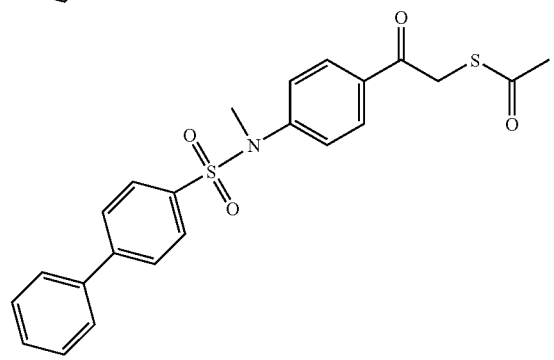

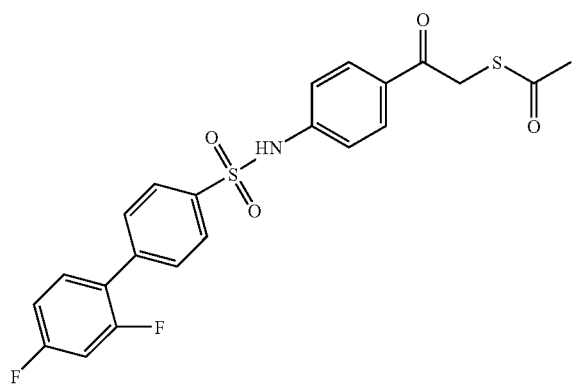

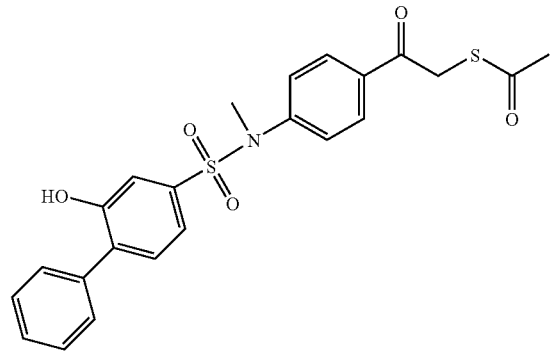

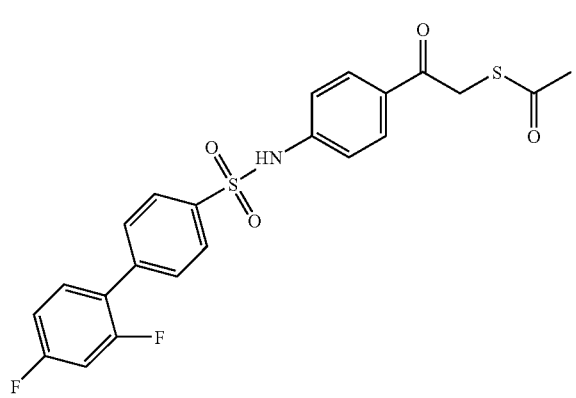

141
-continued
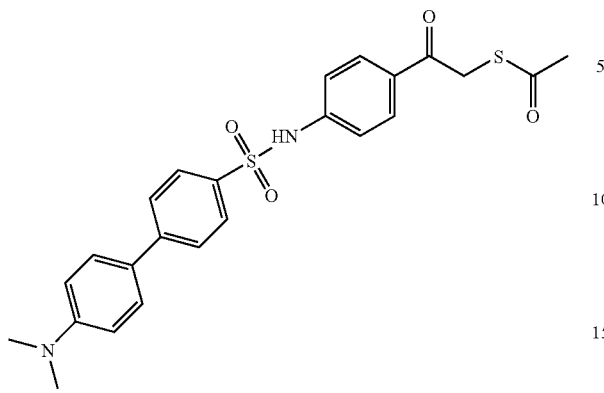
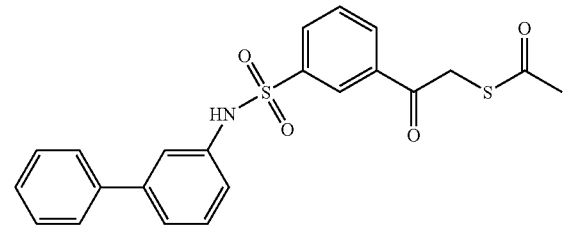
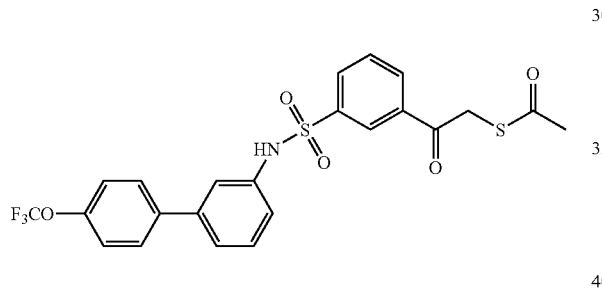
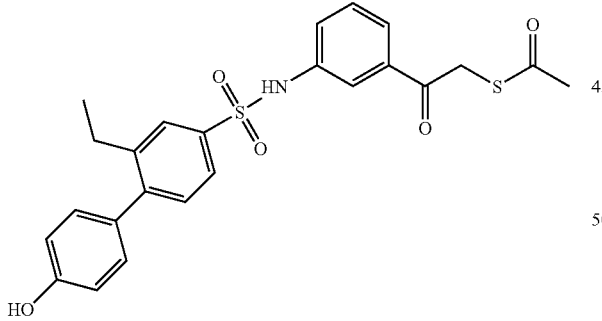
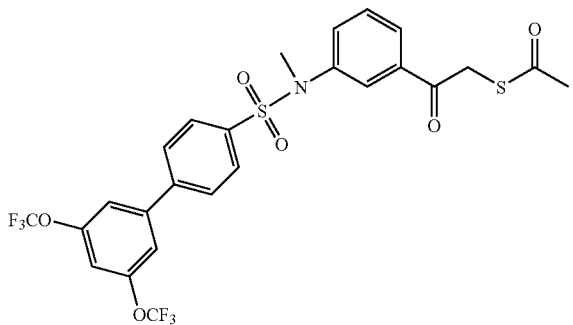
142
-continued
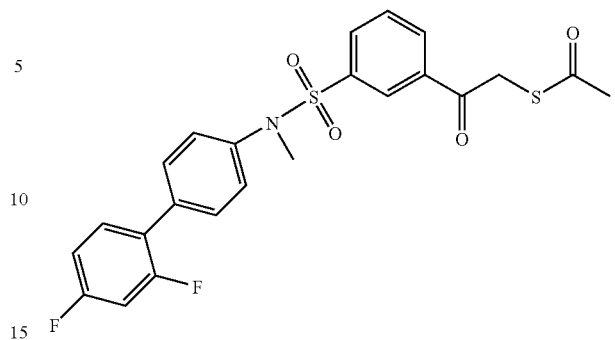
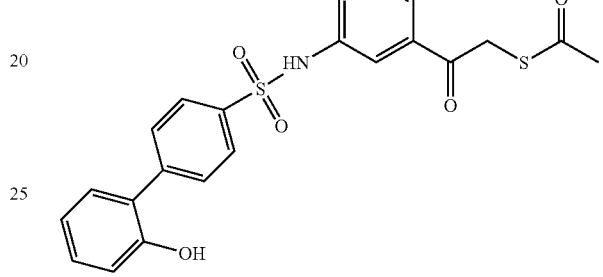
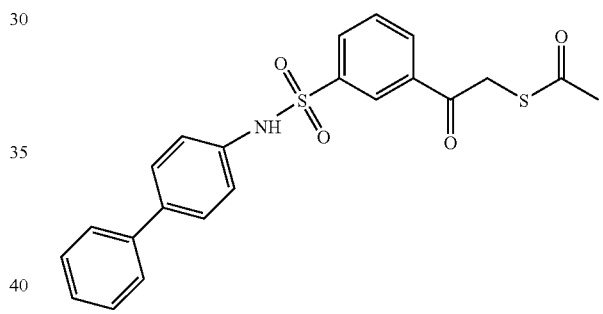
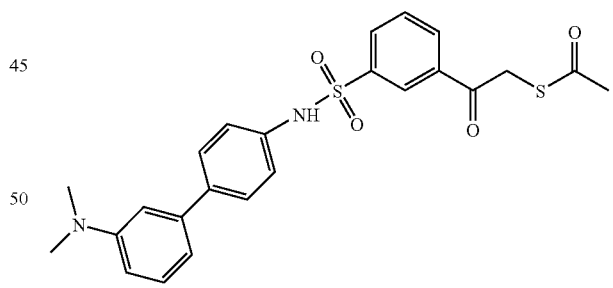
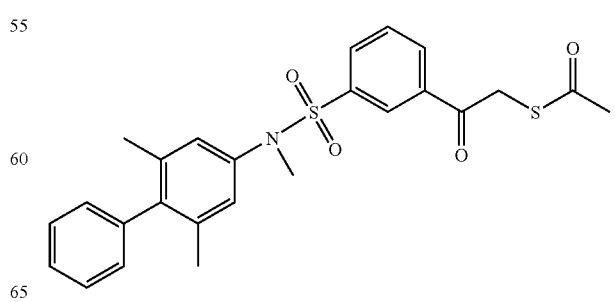

-continued and

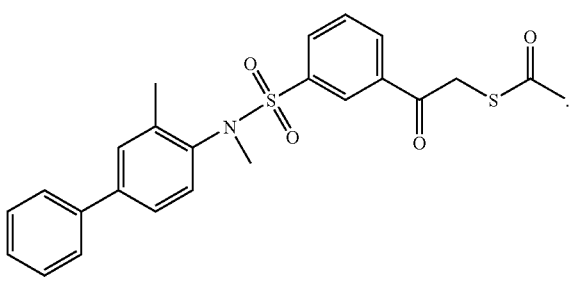

34. The compound of claim 1, selected from the group consisting of

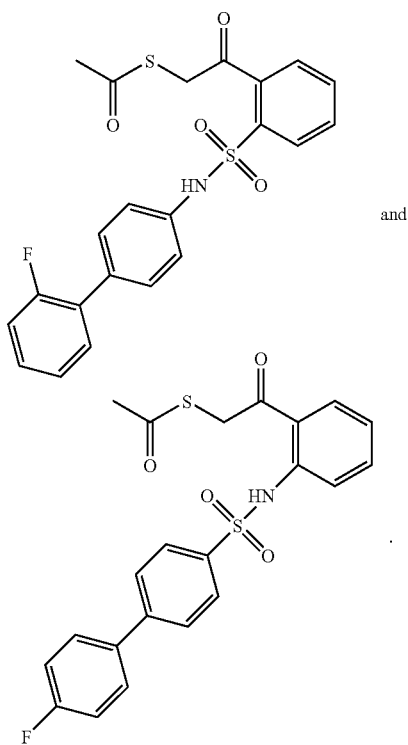

35. The compound of claim 1 wherein G1 is an optionally substituted linked aryl and heteroaryl ring.

36. The compound of claim 35 wherein G1 is selected from the group consisting of:

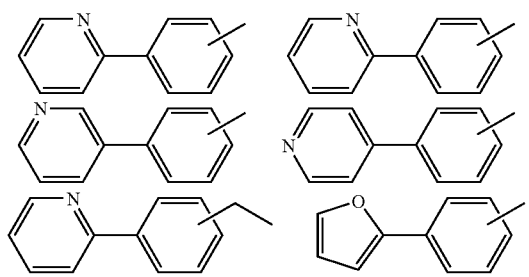

-continued

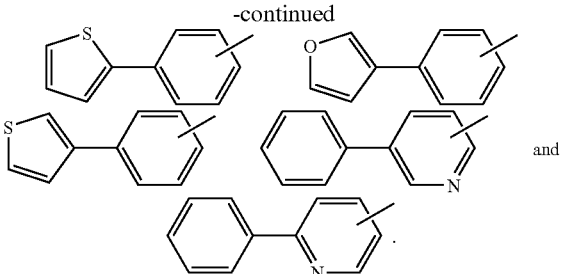

37. The compound of claim 36 wherein G1 is optionally singly or multiply substituted with substituents independently chosen from the group consisting of hydrogen, perhaloaryloxy, alkanoylalkyl, N-aryl-N-alkylamino, hydroxyalkoxy, carboxamidoalkoxy, alkoxycarbonylalkoxy, alkoxycarbonylalkenyloxy, aralkanoylalkoxy, aralkenoyl, N-alkylcarboxamido, N- haloalkylcarboxamido, N-cycloalkylcarboxamide, N-arylcarboxamidoalkoxy, cycloalkylcarbonyl, cyanoalkoxy, carboxy, cycloalkylamino, acylalkyl, acylalkoxy, aroylalkoxy, aralkylaryl, aralkyl, aralkenyl, aralkynyl, haloalkylthio, alkanoyloxy, alkoxy, alkoxyalkyl, cycloalkoxy, cycloalkylalkoxy, hydroxyl, amino, thio, nitro, alkylamino, alkylthio, arylamino, aralkylamino, arylthio, arylthioalkyl, alkylsulfonyl, arylsulphonyl, alkanoyl, alkenoyl, aroyl, aralkanoyl, haloalkanoyl, alkyl, alkenyl, alkynyl, alkenyloxy, alkylenedioxy, haloalkylenedioxy, cycloalkyl, cycloalkylalkanoyl, halo, haloalkyl, haloalkoxy, hydroxyhaloalkyl, hydroxyhaloalkoxy, hydroxyalkyl, aryl, aryloxy, aralkoxy, arylalkenyl, carboalkoxy, alkoxycarboxamido, alkylamidocarboylamido, arylamidocarboylamido, carboalkoxyalkyl, carboalkoxyalkenyl, carboamido, carboxamidoalkyl, cyanocycloalkylalkyl, cycloalkenyl, alkoxycarbonyl, aralkylthio, alkylthio, alkylsulfinyl, arylsulfinyl, dialkylamino, aminoalkyl, dialkylaminoalkyl, aminoaryl, alkylaminoaryl, acylamino, aminocarbonylalkoxy, aminocarbonylamino, aminothiocarbonylamino, and aminothiocarbonylaminoalkyl.

38. The compound of claim 37 wherein Q is a bond.

39. The compound of claim 38 wherein $R_1$, $R_2$, $R_4$, and $R_5$ are hydrogen.

40. The compound of claim 39 wherein G2 is a bond, methylene, or ethylene.

41. The compound according to claim 40 wherein the compound has the structure selected from the group consisting of:

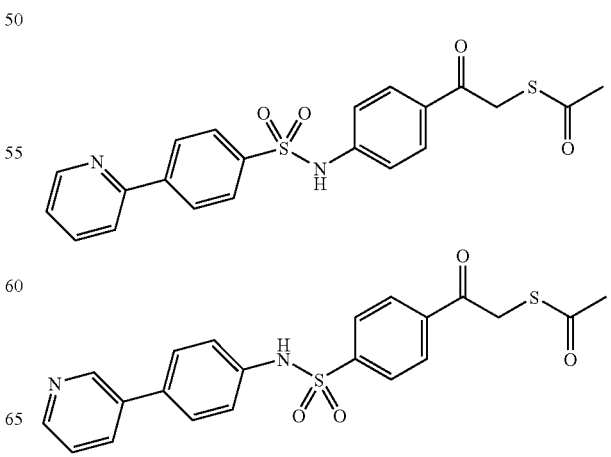

-continued
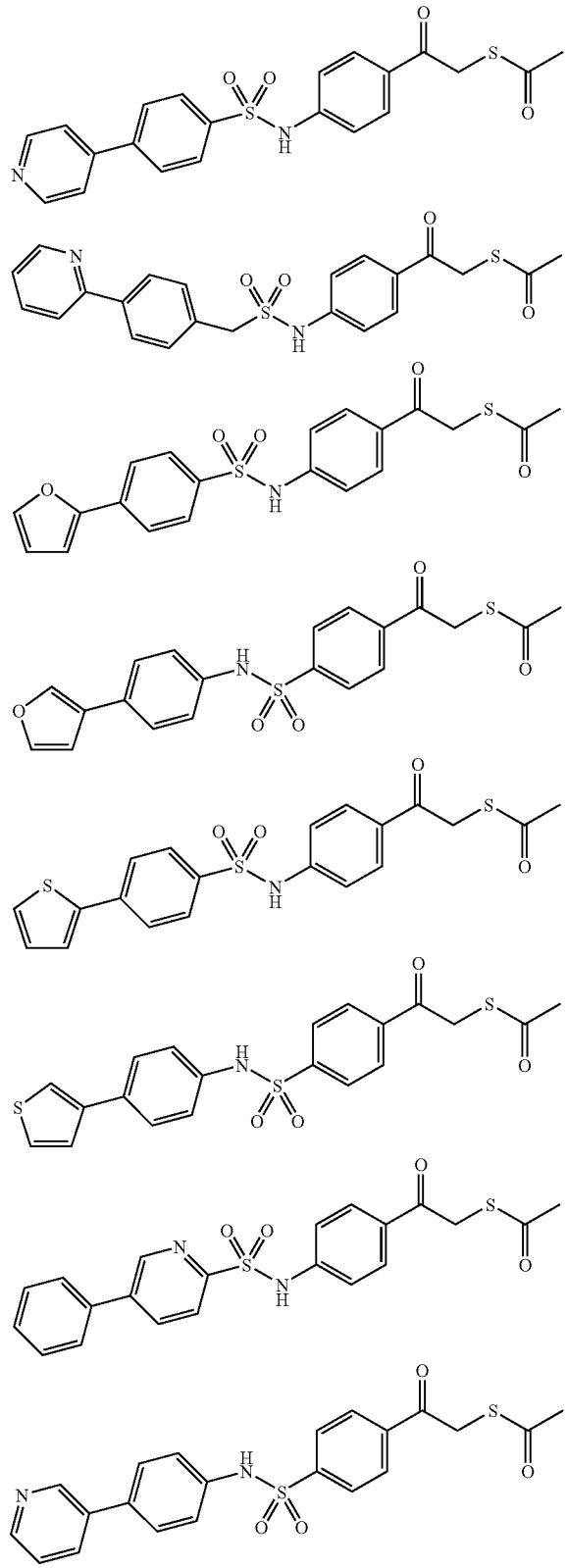
-continued
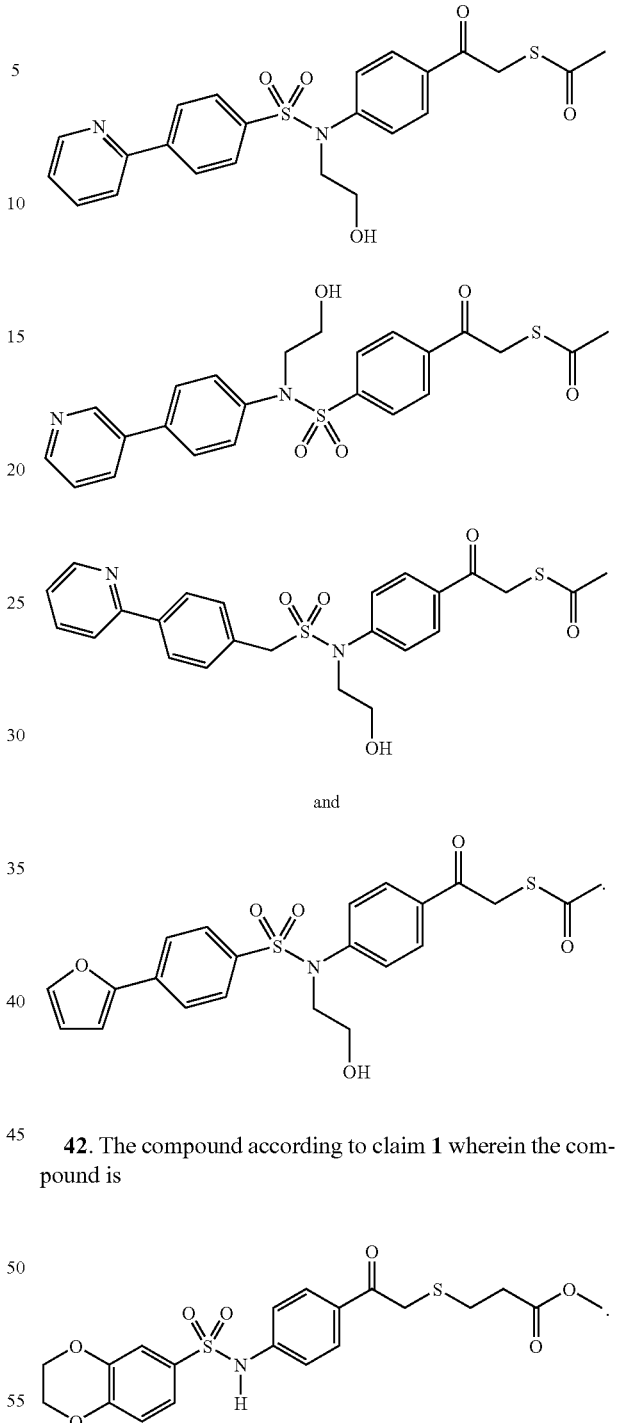
42. The compound according to claim 1 wherein the compound is
43. A pharmaceutical composition comprising the compound of claim 1 in a mixture with at least one carrier, diluent or excipient.
* * * * *